(12) United States Patent
Wu et al.

(10) Patent No.: US 11,038,123 B2
(45) Date of Patent: Jun. 15, 2021

(54) COMPOUND AND ORGANIC ELECTRONIC DEVICE USING THE SAME

(71) Applicant: NICHEM FINE TECHNOLOGY CO., LTD., Jhubei (TW)

(72) Inventors: Hui-Ling Wu, Jhubei (TW); Ming-Zer Lee, Jhubei (TW); Shwu-Ju Shieh, Jhubei (TW); Chi-Chung Chen, Jhubei (TW)

(73) Assignee: SHANGHAI NICHEM FINE CHEMICAL CO., LTD., Shanghai (CN)

( * ) Notice: Subject to any disclaimer, the term of this patent is extended or adjusted under 35 U.S.C. 154(b) by 431 days.

(21) Appl. No.: 15/934,943

(22) Filed: Mar. 23, 2018

(65) Prior Publication Data

US 2018/0277772 A1 Sep. 27, 2018

Related U.S. Application Data

(60) Provisional application No. 62/476,648, filed on Mar. 24, 2017.

(51) Int. Cl.
| | | |
|---|---|---|
| *H01L 51/00* | (2006.01) | |
| *H01L 51/50* | (2006.01) | |
| *H01L 51/52* | (2006.01) | |
| *H01L 51/56* | (2006.01) | |
| *C07D 307/91* | (2006.01) | |

(52) U.S. Cl.
CPC ...... *H01L 51/0073* (2013.01); *H01L 51/5012* (2013.01); *H01L 51/5064* (2013.01); *H01L 51/5072* (2013.01); *H01L 51/5092* (2013.01); *H01L 51/5096* (2013.01); *H01L 51/5206* (2013.01); *H01L 51/5221* (2013.01); *H01L 51/56* (2013.01); *C07D 307/91* (2013.01); *H01L 2251/5384* (2013.01)

(58) Field of Classification Search
CPC ............. H01L 51/0073; H01L 51/5012; H01L 51/5064; H01L 51/5072; H01L 51/5092; H01L 51/5221; H01L 51/5206; H01L 51/56; H01L 51/5096; H01L 51/0052; H01L 51/0058; H01L 51/50; H01L 2251/5384; C07D 307/91; C07D 407/14
See application file for complete search history.

(56) References Cited

U.S. PATENT DOCUMENTS

| | | | | |
|---|---|---|---|---|
| 2017/0018723 | A1* | 1/2017 | Cha | C07D 307/94 |
| 2018/0123055 | A1* | 5/2018 | Park | H01L 51/0073 |
| 2018/0182971 | A1* | 6/2018 | Park | H01L 51/0058 |
| 2018/0277771 | A1* | 9/2018 | Park | H01L 51/0073 |

FOREIGN PATENT DOCUMENTS

CN 106356468 A 1/2017

* cited by examiner

*Primary Examiner* — Robert S Jones, Jr.
(74) *Attorney, Agent, or Firm* — Pai Patent & Trademark Law Firm; Chao-Chang David Pai

(57) ABSTRACT

Provided are a novel compound and an organic electronic device using the same. The novel compound is represented by the following Formula (I):

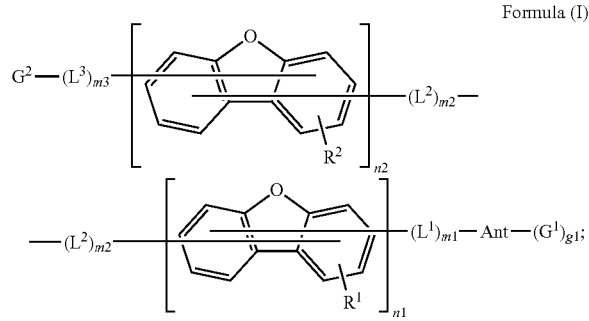

Formula (I)

wherein n1, n2, m1, m2, m3, and g1 are each independently an integral, and the sum of n1 and n2 is 2 or 3; Ant is

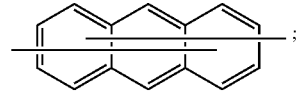

;

$L^1$, $L^2$ and $L^3$ are each independently an arylene group; $G^1$ and $G^2$ are each independently selected from the group consisting of: a hydrogen atom, a deuterium atom, an alkyl group, an alkenyl group, an alkynyl group, a cycloalkyl group, a heterocycloalkyl group, an aryl group, and a heteroaryl group; and $R^1$ and $R^2$ are each independently selected from the group consisting of: a hydrogen atom, a deuterium atom, an alkyl group, and an aryl group.

16 Claims, 22 Drawing Sheets

COMPOUND AND ORGANIC ELECTRONIC DEVICE USING THE SAME

CROSS-REFERENCE TO RELATED APPLICATION

Pursuant to 35 U.S.C. § 119(e), this application claims the benefits of the priority to U.S. Provisional Patent Application No. 62/476,648, filed Mar. 24, 2017. The contents of the prior application are incorporated herein by its entirety.

BACKGROUND OF THE INVENTION

1. Field of the Invention

The present invention relates to a novel compound and an organic electronic device using the same, more particularly to a novel compound as host materials for an emission layer and an organic electronic device using the same.

2. Description of the Prior Arts

With the advance of technology, various organic electronic devices that make use of organic materials have been energetically developed. Examples of the organic electronic devices include organic light emitting devices (OLEDs), organic phototransistors, organic photovoltaic cells, and organic photodetectors.

OLED was initially invented and proposed by Eastman Kodak Company through a vacuum evaporation method. Dr. Ching W. Tang and Steven VanSlyke of Kodak Company deposited an electron transport material such as tris(8-hydroxyquinoline)aluminum(III) (abbreviated as Alq$_3$) on a transparent indium tin oxide glass (abbreviated as ITO glass) formed with a hole transport layer of organic aromatic diamine thereon, and subsequently deposited a metal electrode onto an electron transport layer to complete the fabrication of the OLED. OLEDs have attracted lots of attention due to their numerous advantages, such as fast response speed, light weight, compactness, wide viewing angle, high brightness, higher contrast ratio, no need of backlight, and low power consumption. However, the OLEDs still have the problems such as low efficiency and short lifetime.

To overcome the problem of low efficiency, one of the approaches is to interpose some interlayers between the cathode and the anode. With reference to FIG. 1, a modified OLED 1 may have a structure of a substrate 11, an anode 12, a hole injection layer 13 (abbreviated as HIL), a hole transport layer 14 (abbreviated as HTL), an emission layer 15 (abbreviated as EL), an electron transport layer 16 (abbreviated as ETL), an electron injection layer 17 (abbreviated as EIL), and a cathode 18 stacked in sequence. When a voltage is applied between the anode 12 and the cathode 18, the holes injected from the anode 12 move to the EL via HIL and HTL and the electrons injected from the cathode 18 move to the EL via EIL and ETL. Recombination of the electrons and the holes occurs in the EL to generate excitons, thereby emitting a light when the excitons decay from excited state to ground state.

Another approach is to adopt a phenylanthracene derivative, such as 9,10-diphenylanthracene, 9,10-dinaphthylanthracene, 9-naphthyl-10-phenylanthracene, 9-(4-(naphthalen-1-yl)phenyl)-10-(naphthalen-2-yl) anthracene, 2-methyl-9,10-bis(naphthalen-2-yl)anthracene, or 2-phenyl-9,10-bis(naphthalen-2-yl)anthracene, as a host material of the EL. The phenylanthracene derivative is used as a blue host material of the EL for blue OLEDs. However, even using the foresaid host materials of the EL, the current efficiency and luminous efficacy of OLEDs still needs to be improved.

Therefore, the present invention provides a novel compound to mitigate or obviate the problems in the prior art.

SUMMARY OF THE INVENTION

An objective of the present invention is to provide a novel compound useful for an organic electronic device.

Another objective of the present invention is to provide an organic electronic device using the novel compound, so as to improve the efficiency of the organic electronic device.

To achieve the foresaid objectives, the present invention provides a novel compound represented by the following Formula (I):

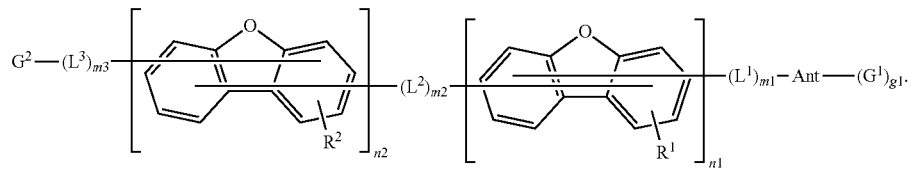

In Formula (I), Ant is

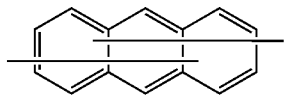

In Formula (I), n1 and n2 are each independently an integer from 0 to 3, and the sum of n1 and n2 is 2 or 3.

In Formula (I), m1, m2 and m3 are each independently an integer 0 or 1. That is, m1, m2 and m3 can be the same or different.

In Formula (I), g1 is an integer from 0 to 9.

In Formula (I), $R^1$ and $R^2$ are each independently selected from the group consisting of: a hydrogen atom, a deuterium atom, an alkyl group having 1 to 12 carbon atoms, and an aryl group having 6 to 30 ring carbon atoms, and $R^1$ and $R^2$ are the same or different.

In Formula (I), $L^1$, $L^2$ and $L^3$ are each independently an arylene group having 6 to 60 ring carbon atoms, and $L^1$, $L^2$ and $L^3$ are the same or different.

In Formula (I), $G^1$ and $G^2$ are each independently selected from the group consisting of: a hydrogen atom, a deuterium atom, an alkyl group having 1 to 40 carbon atoms, an alkenyl group having 2 to 40 carbon atoms, an alkynyl group having 2 to 40 carbon atoms, a cycloalkyl group having 3 to 60 ring carbon atoms, a heterocycloalkyl group having 3 to 60 ring carbon atoms, an aryl group having 6 to 60 ring carbon atoms, and a heteroaryl group having 3 to 60 ring carbon atoms.

In accordance with the present invention, the compound is represented by the following Formula (I'):

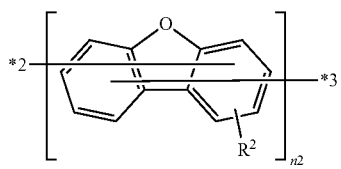

Formula (I')

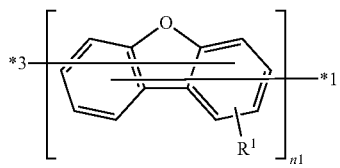

b*—(L³)_{m3}—G²  *4—(L²)_{m2}—*4  *a—(L¹)_{m1}—Ant—(G¹)_{g1};

wherein *1 is bonded to *a, *2 is bonded to *b, and two *3s are bonded to two *4s, respectively.

Preferably, the compound is represented by the following Formula (I"):

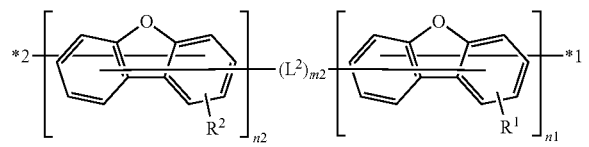

Formula (I")

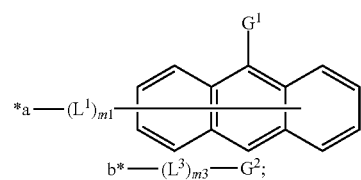

wherein *a is bonded to *1, and *b is bonded to *2.

In the case that both bonding groups of dibenzofuranyl are bonded on the same benzene ring, for example, the group of

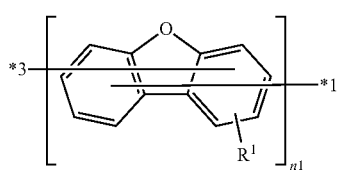

in Formula (I') may be represented by

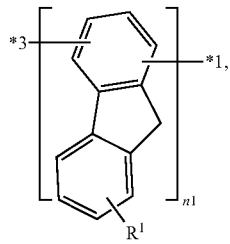

or the group of

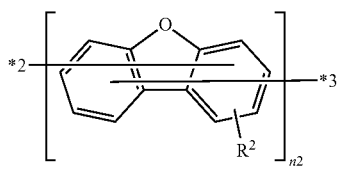

in Formula (I') may be represented by

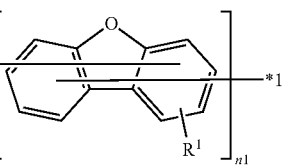

More specifically, the group of in Formula (I') may be represented by any one of the following formulae:

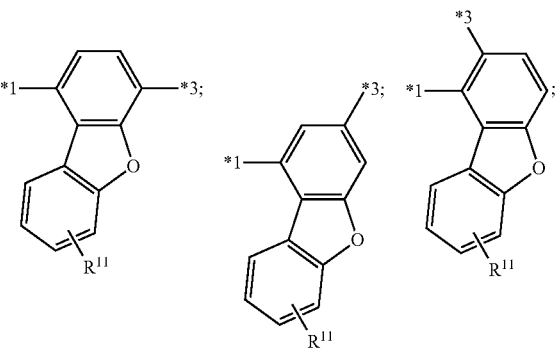

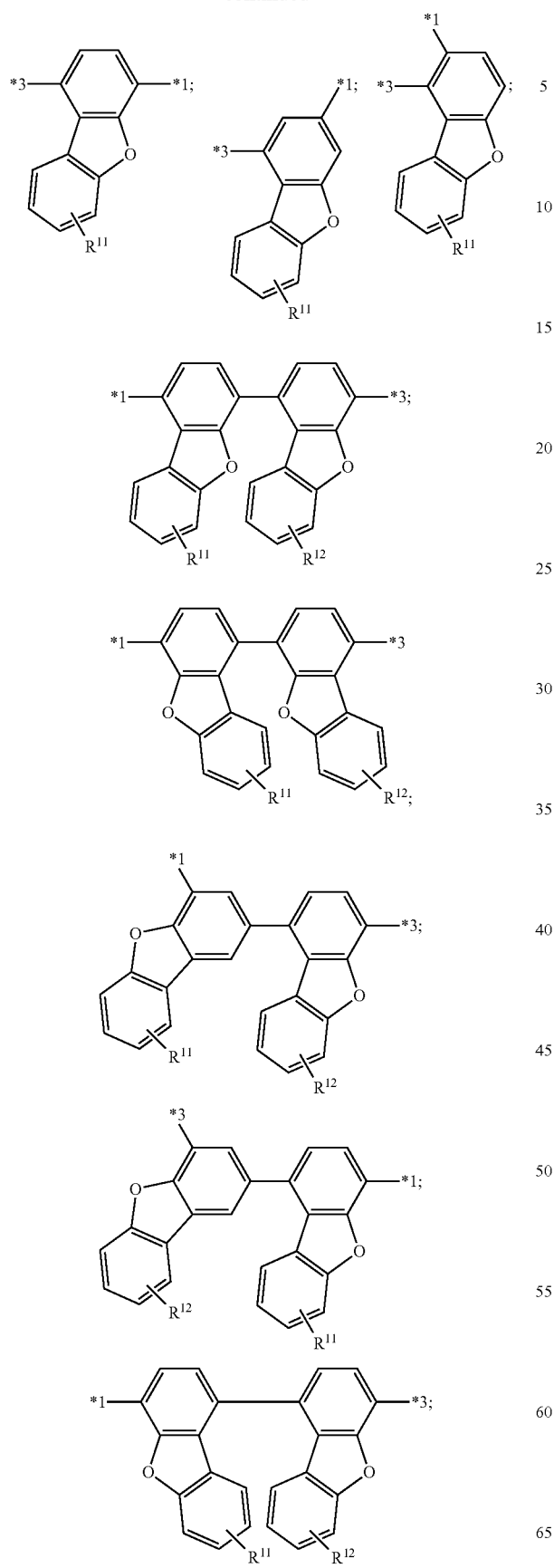
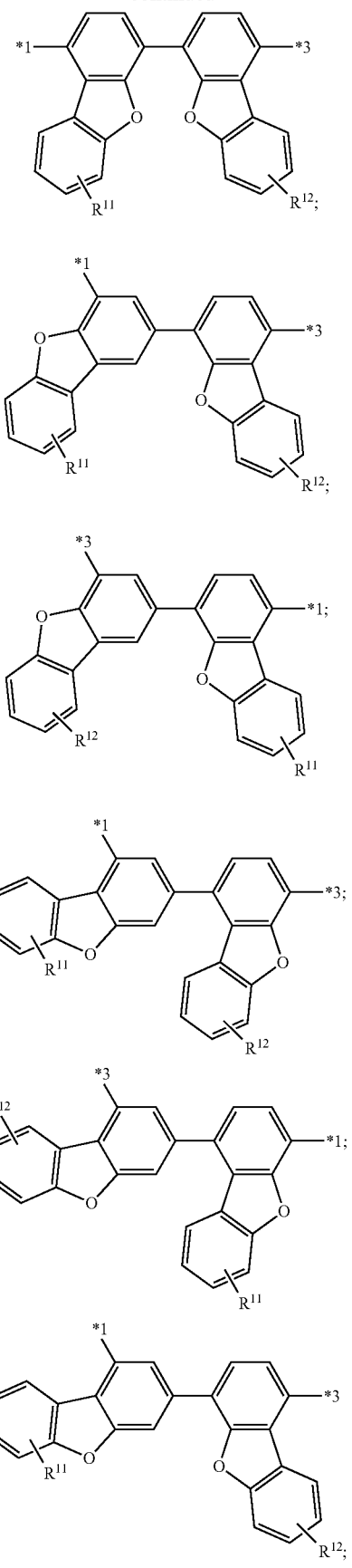

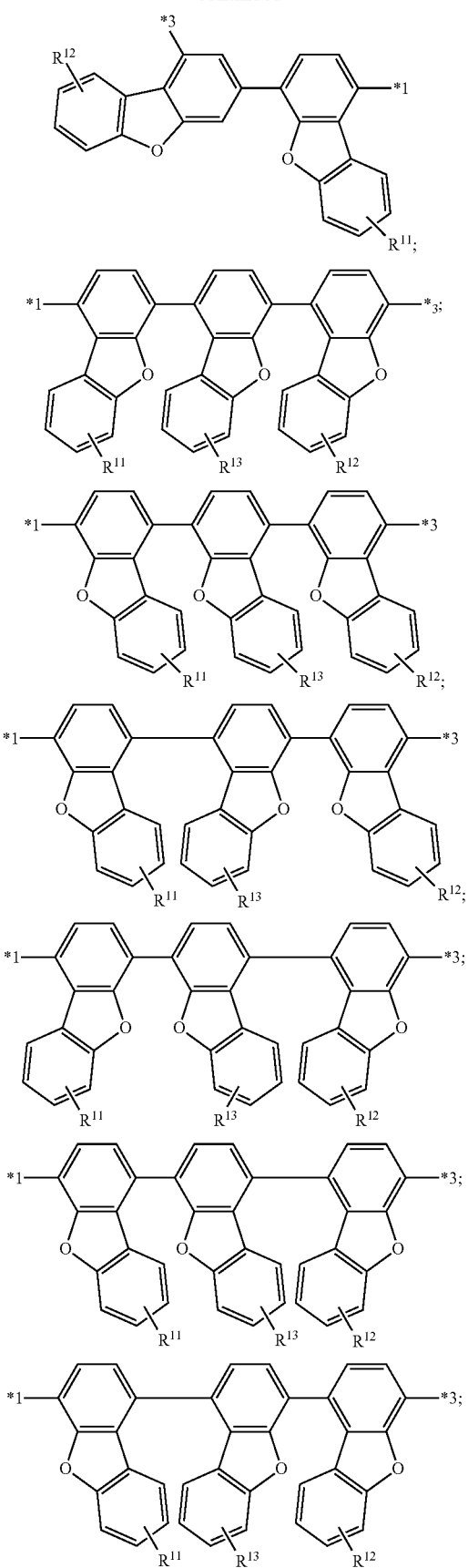

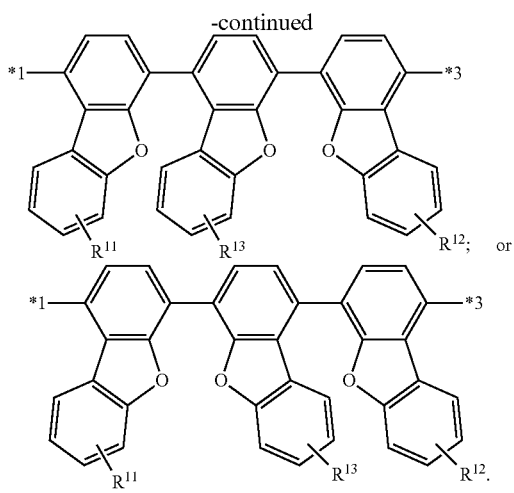

$R^1$ group in Formula (I) may be represented by $R^{11}$ to $R^{13}$. Herein, $R^{11}$ to $R^{13}$ are each independently selected from the group consisting of: a hydrogen atom, a deuterium atom, an alkyl group having 1 to 12 carbon atoms, and an aryl group having 6 to 30 ring carbon atoms, and $R^{11}$ to $R^{13}$ are the same or different.

More specifically, the group of

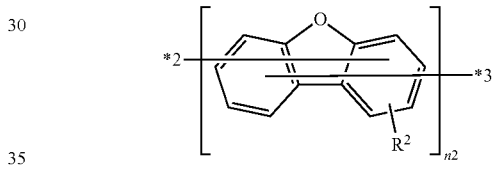

in Formula (I') may be represented by any one of the following formulae:

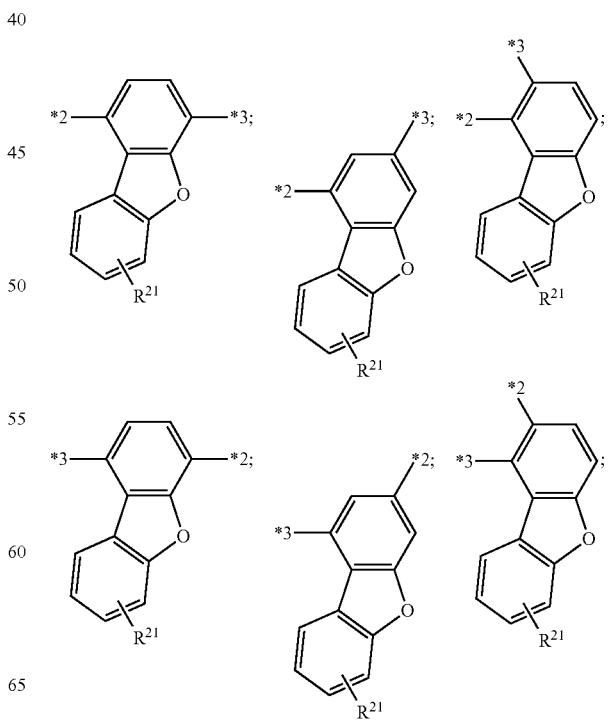

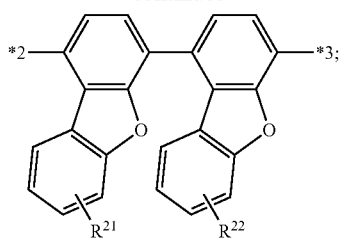
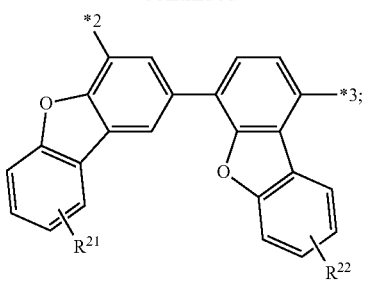
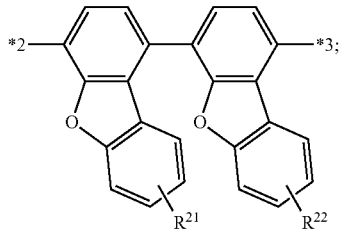
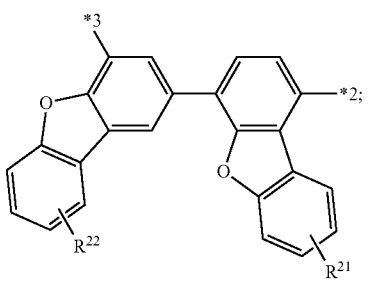
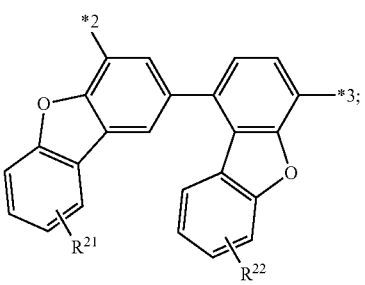
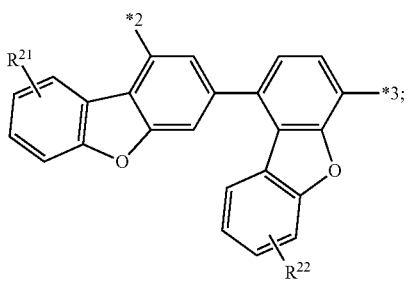
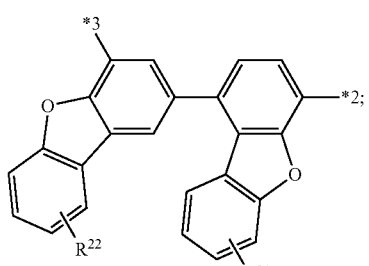
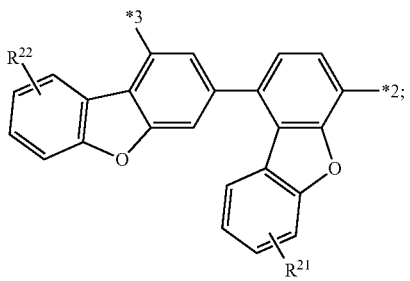
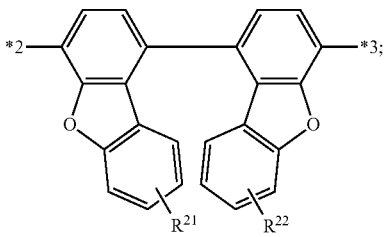
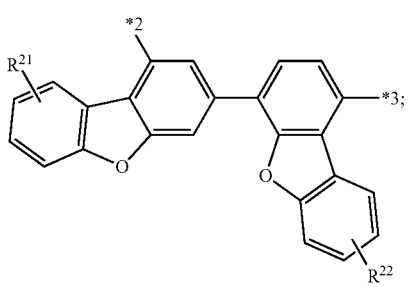
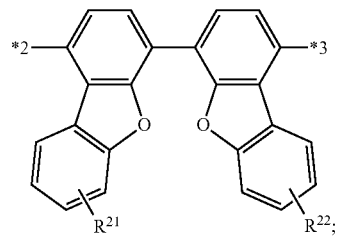
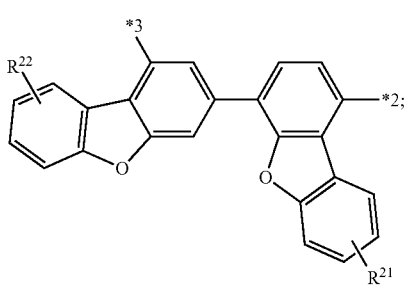

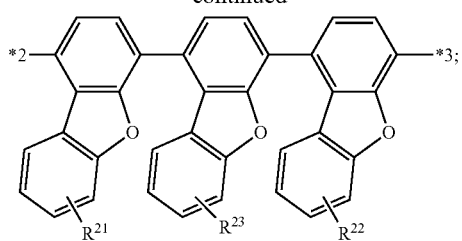

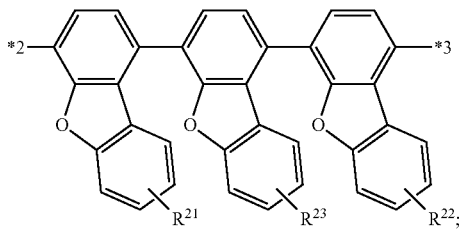

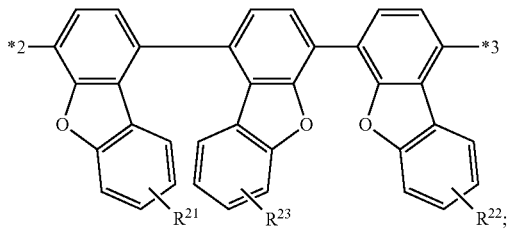

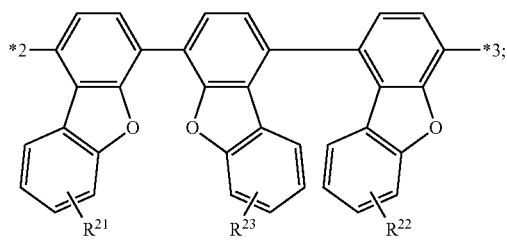

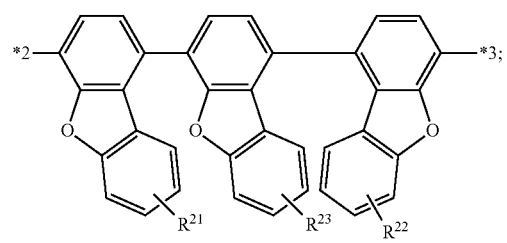

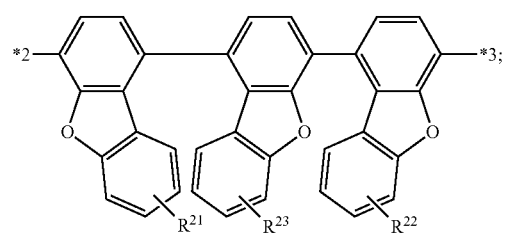

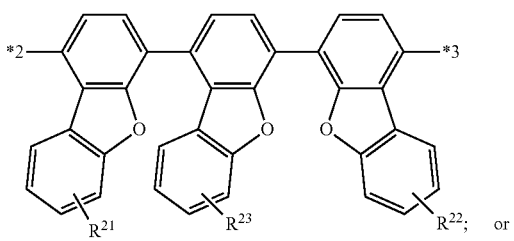 or

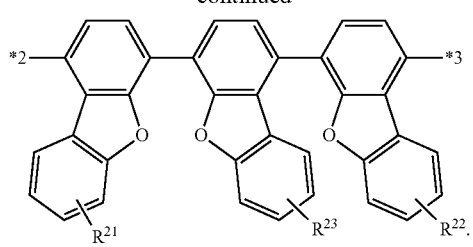

$R^2$ group in Formula (I) may be represented by $R^{21}$ to $R^{23}$. Herein, $R^{21}$ to $R^{23}$ are each independently selected from the group consisting of: a hydrogen atom, a deuterium atom, an alkyl group having 1 to 12 carbon atoms, and an aryl group having 6 to 30 ring carbon atoms, and $R^{21}$ to $R^{23}$ are the same or different.

More specifically, the groups of

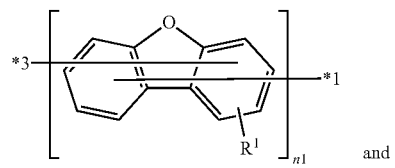 and

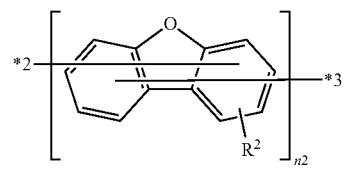

may be the same or different.

When n1 is 1, i.e., the group of

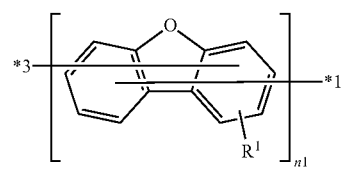

in Formula (I') is

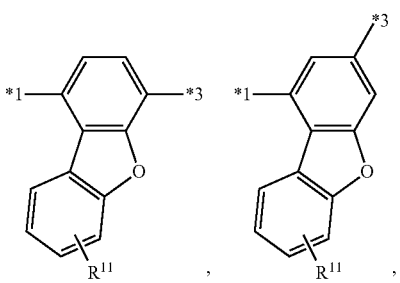

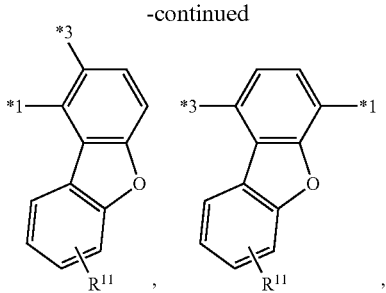

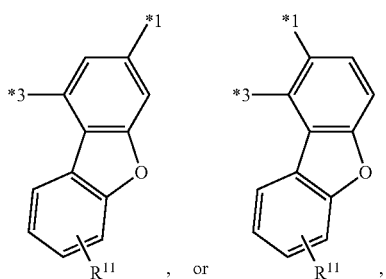

n2 is an integer 1 or 2.
Likely, when n2 is 1, i.e., the group of

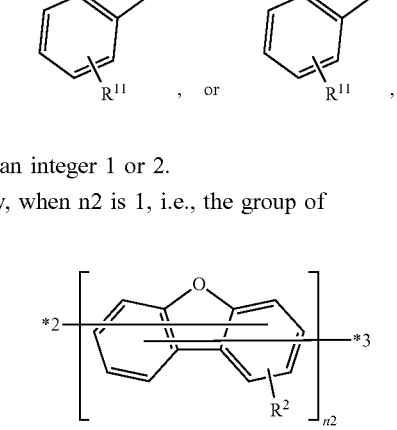

in Formula (I') is

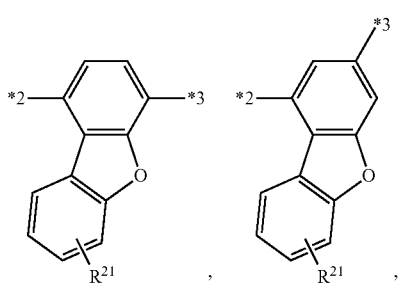

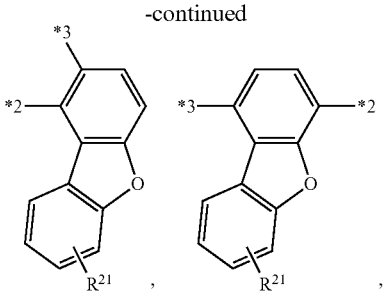

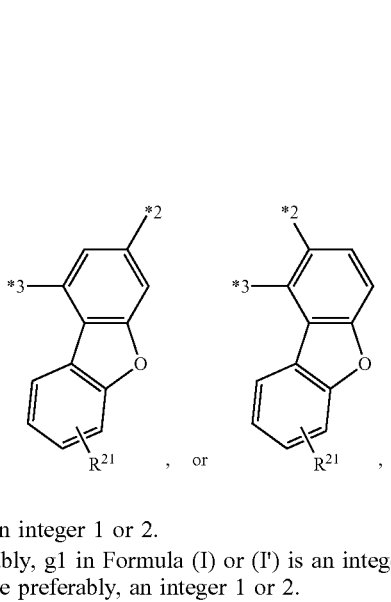

n1 is an integer 1 or 2.
Preferably, g1 in Formula (I) or (I') is an integer from 0 to 2; more preferably, an integer 1 or 2.

In the case that g1 is an integer integral of 1, $G^1$ may be represented by

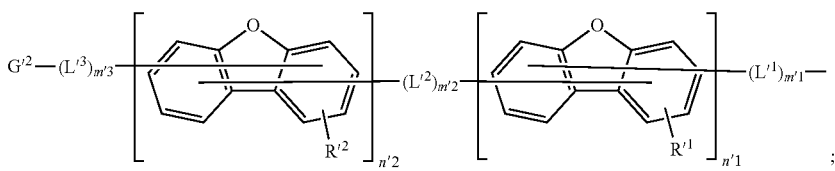

wherein n'1 and n'2 are each independently an integer from 0 to 3, and the sum of n'1 and n'2 is 2 or 3;

m'1, m'2 and m'3 are each independently an integer 0 or 1, and m'1, m'2 and m'3 are the same or different;

$R'^1$ and $R'^2$ are each independently selected from the group consisting of: a hydrogen atom, a deuterium atom, an alkyl group having 1 to 6 carbon atoms, and an aryl group having 6 to 18 ring carbon atoms, and $R'^1$ and $R'^2$ are the same or different;

$L'^1$, $L'^2$ and $L'^3$ are each independently an arylene group having 6 to 18 ring carbon atoms, and $L'^1$, $L'^2$ and $L'^3$ are the same or different;

$G'^2$ is selected from the group consisting of: a hydrogen atom, a deuterium atom, an alkyl group having 1 to 12 carbon atoms, an alkenyl group having 2 to 12 carbon atoms, an alkynyl group having 2 to 12 carbon atoms, a cycloalkyl group having 3 to 30 ring carbon atoms, a heterocycloalkyl group having 3 to 30 ring carbon atoms, an aryl group having 6 to 30 ring carbon atoms, and a heteroaryl group having 3 to 30 ring carbon atoms.

Preferably, n1 and n2 are respectively identical to n'1 and n'2; m1, m2, and m3 are respectively identical to m'1, m'2 and m'3; g1 is an integer 1; $R^1$ and $R^2$ are respectively identical to $R'^1$ and $R'^2$; $L^1$, $L^2$ and $L^3$ are respectively identical to $L'^1$, $L'^2$ and $L'^3$; and $G^1$ is identical to $G^2$; such that the compound is a symmetrical compound.

Preferably, the compound is represented by the following Formula (I'''):

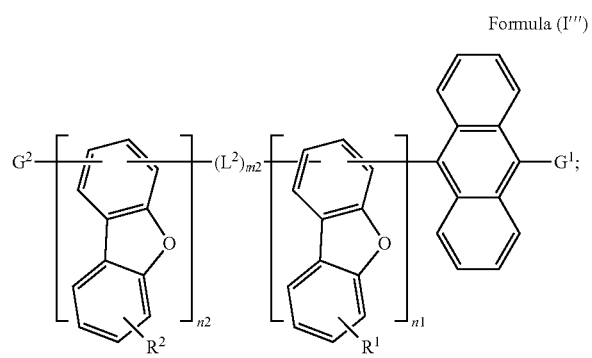

Formula (I''')

wherein $R^1$ and $R^2$ are each independently selected from the group consisting of: a hydrogen atom, a deuterium atom, an alkyl group having 1 to 12 carbon atoms, and an aryl group having 6 to 30 ring carbon atoms, and $R^1$ and $R^2$ are the same or different;

$G^1$ is selected from the group consisting of: the alkyl group having 1 to 40 carbon atoms, the alkenyl group having 2 to 40 carbon atoms, the alkynyl group having 2 to 40 carbon atoms, and the aryl group having 6 to 60 ring carbon atoms; and $G^2$ is selected from the group consisting of: the hydrogen atom, the deuterium atom, the alkyl group having 1 to 40 carbon atoms, the alkenyl group having 2 to 40 carbon atoms, the alkynyl group having 2 to 40 carbon atoms, and the aryl group having 6 to 60 ring carbon atoms.

Preferably, $R^1$ and $R^2$ in Formula (I'''), are each independently selected from the group consisting of: a hydrogen atom, a deuterium atom, an alkyl group having 1 to 6 carbon atoms, and an aryl group having 6 to 12 ring carbon atoms.

More preferably, $G^1$ is selected from the group consisting of: a phenyl group, a naphthyl group, and a biphenylyl group.

Preferably, in Formula (I'''), n1 and n2 are each independently an integer 1 or 2.

Preferably, in Formula (I'''), m2 is an integer 0 or 1, and $L^2$ is the arylene group as stated below, such as phenylene group. When m2 is an integer 0, $(L^2)_{m2}$ is a single bond.

Preferably, the heteroaryl group having 3 to 60 ring carbon atoms represented by $G^1$ and $G^2$ in Formulae (I) to (I'') are each independently selected from the group consisting of: a furyl group, a pyrrolyl group, a thiophenyl group; an imidazolyl group, a pyrazolyl group, a triazolyl group, a tetrazolyl group, an oxazolyl group, an isoxazolyl group, a thiazolyl group, an isothiazolyl group, an oxadiazolyl group, a thiadiazolyl group; a pyridyl group, a pyridazinyl group, a pyrimidinyl group, a pyrazinyl group, a triazinyl group; an indolyl group, an isoindolyl group, a benzofuranyl group, an isobenzofuranyl group, a benzothiophenyl group, an isobenzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group; an indazolyl group, a benzisoxazolyl group, a benzisothiazolyl group; a dibenzofuranyl group, a dibenzothiophenyl group, a carbazolyl group, a biscarbazolyl group, a coumarinyl group, a chromenyl group, a phenanthridinyl group, an acridinyl group, a phenanthrolinyl group, a phenazinyl group, a phenothiazinyl group, a phenoxazinyl group, an azatriphenylenyl group, a diazatriphenylenyl group, a xanthenyl group, an azacarbazolyl group, an azadibenzofuranyl group, an azadibenzothiophenyl group, a benzofuranobenzothiophenyl group, a benzothienobenzothiophenyl group, a dibenzofuranonaphthyl group, a dibenzothienonaphthyl group, a dinaphthothienothiophenyl group, a dinaphtho[2',3':2,3:2',3':6,7]carbazolyl group, a dibenzo[b,f]azepin group, a tribenzo[b,d,f]azepin group, a dibenzo[b,f]oxepin group, and a tribenzo[b,d,f]oxepin group.

More specifically, the heteroaryl group having 3 to 60 ring carbon atoms represented by $G^2$ in Formulae (I) to (I'') is represented by any one of the following formulae:

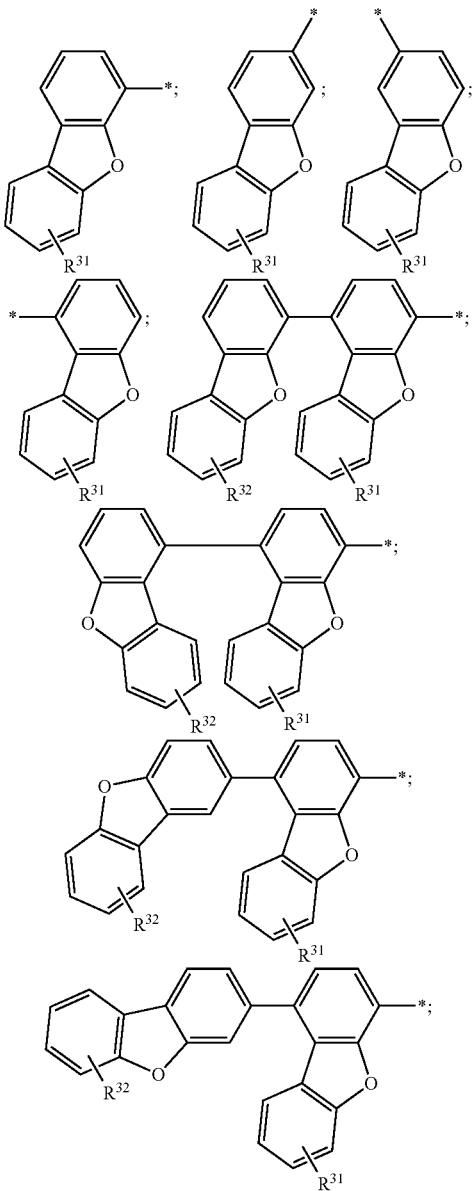

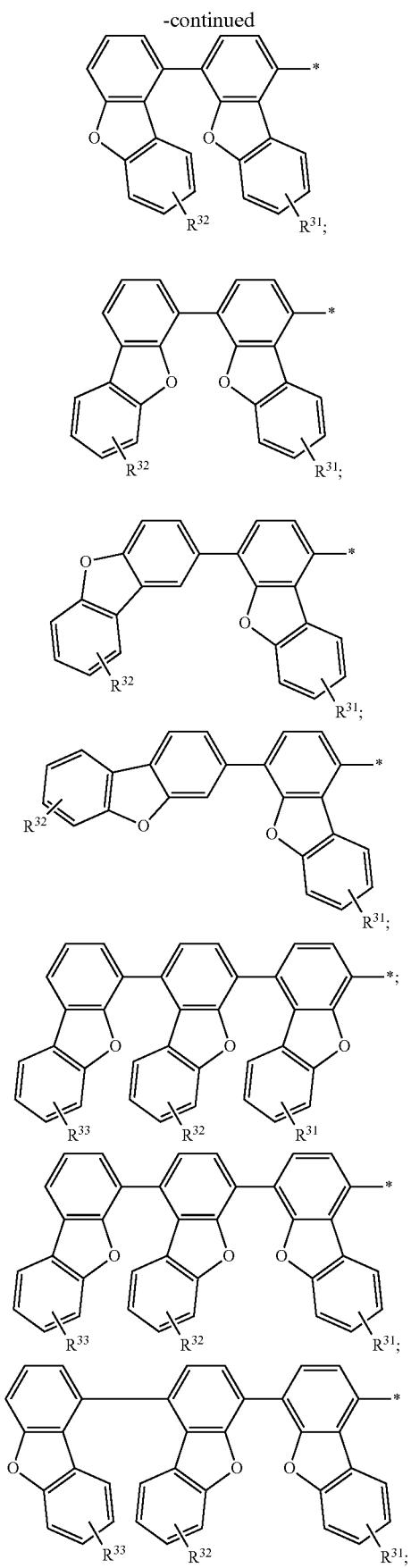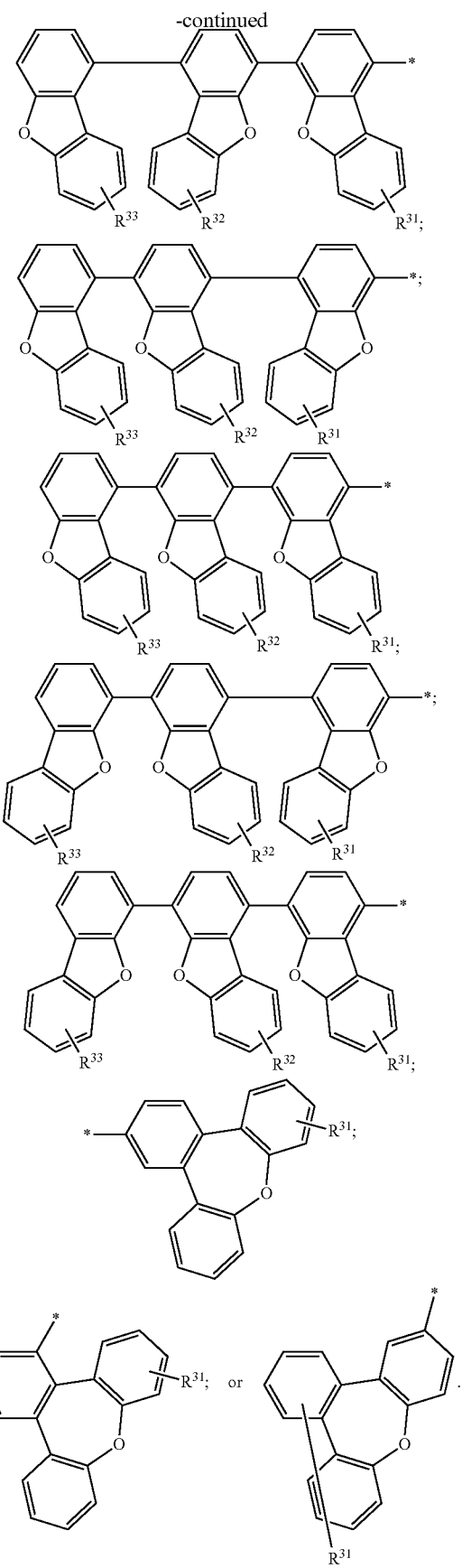

Herein, $R^{31}$ to $R^{33}$ are each independently selected from the group consisting of: a hydrogen atom, a deuterium atom, an alkyl group having 1 to 12 carbon atoms, and an aryl group having 6 to 30 ring carbon atoms, and $R^{31}$ to $R^{33}$ are the same or different.

Preferably, the aryl groups having 6 to 60 ring carbon atoms represented by $G^1$ and $G^2$ in Formulae (I) to (I''') are each independently selected from the group consisting of: a phenyl group, a biphenylyl group, a terphenylyl group, a quaterphenylyl group, a quinquephenylyl group, a naphthyl group, an acenaphthelenyl group, an anthryl group, a benzanthryl group, an aceanthryl group, a phenanthryl group, a benzophenanthryl group, a phenalenyl group, a fluorenyl group, a benzofluorenyl group, a dibenzofluorenyl group, a picenyl group, a pentacenyl group, a pyrenyl group, a benzopyrenyl group, a chrysenyl group, a benzochrysenyl group, a fluoranthenyl group, a benzofluoranthenyl group, a tetracenyl group, a perylenyl group, a coronyl group, a dibenzanthryl group, a naphthylphenyl group, an indacenyl group, a triphenylenyl group, or a benzotriphenylenyl group, and any isomeric group thereof.

More specifically, $G^1$ and $G^2$ in Formulae (I) to (I''') are each independently selected from the group consisting of:

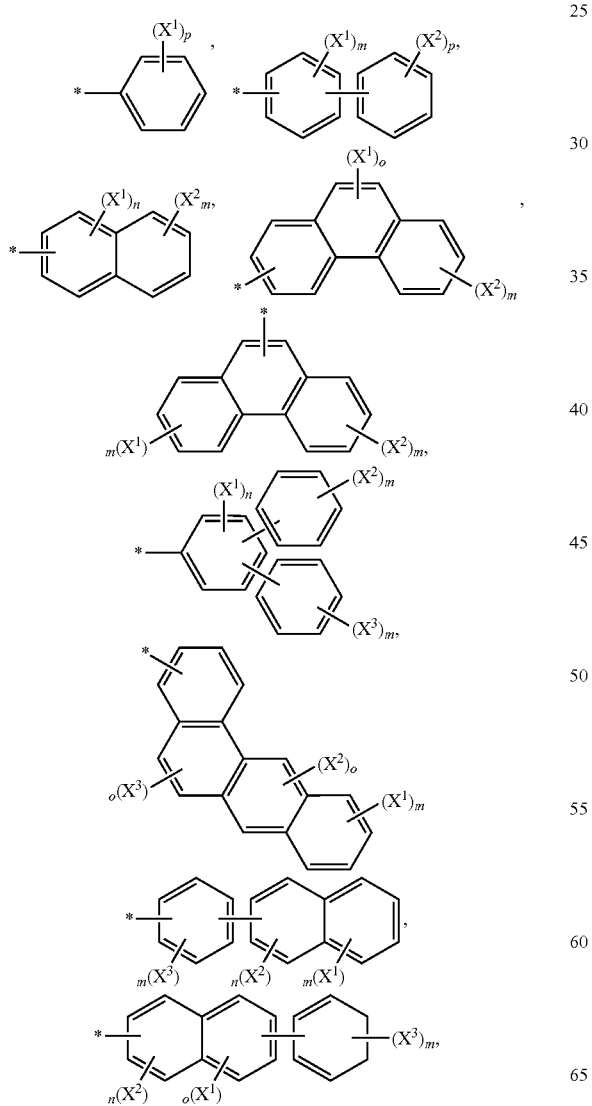

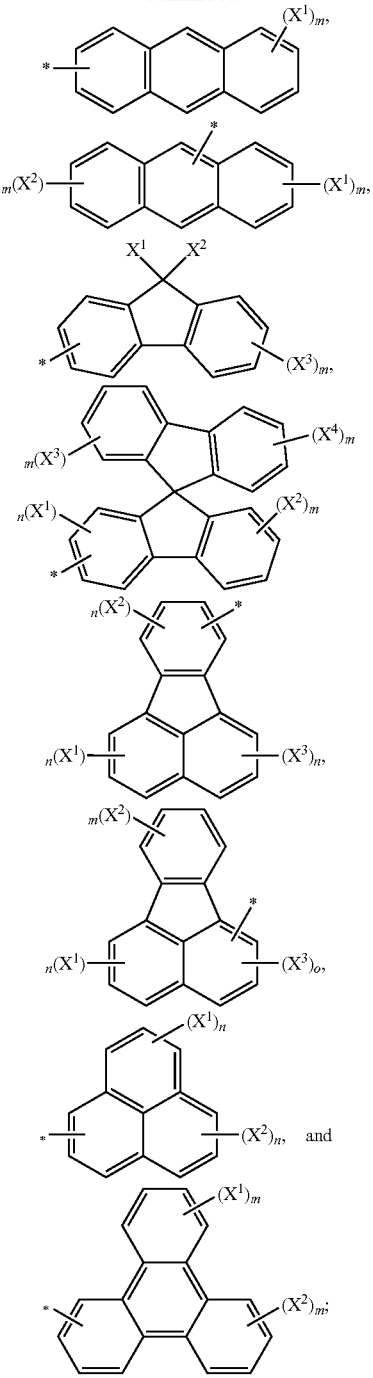

wherein m is an integer from 1 to 4, n is an integer from 1 to 3, o is an integer from 1 or 2, and p is an integer from 1 to 5;

$X^1$ to $X^4$ are each independently selected from the group consisting of: a hydrogen atom, a deuterium atom, a halo group, a cyano group, a nitro group, an alkyl group having 1 to 12 carbon atoms, an alkenyl group having 2 to 12 carbon atoms, an alkynyl group having 2 to 12 carbon atoms, an alkoxy group having 1 to 12 carbon atoms, an aryl group having 6 to 30 ring carbon atoms, a heteroaryl group having 3 to 30 ring carbon atoms, and an aryloxy group having 6 to 30 ring carbon atoms.

More specifically, the aryl groups having 6 to 60 ring carbon atoms represented by $G^1$ or $G^2$ may be selected from the group consisting of:

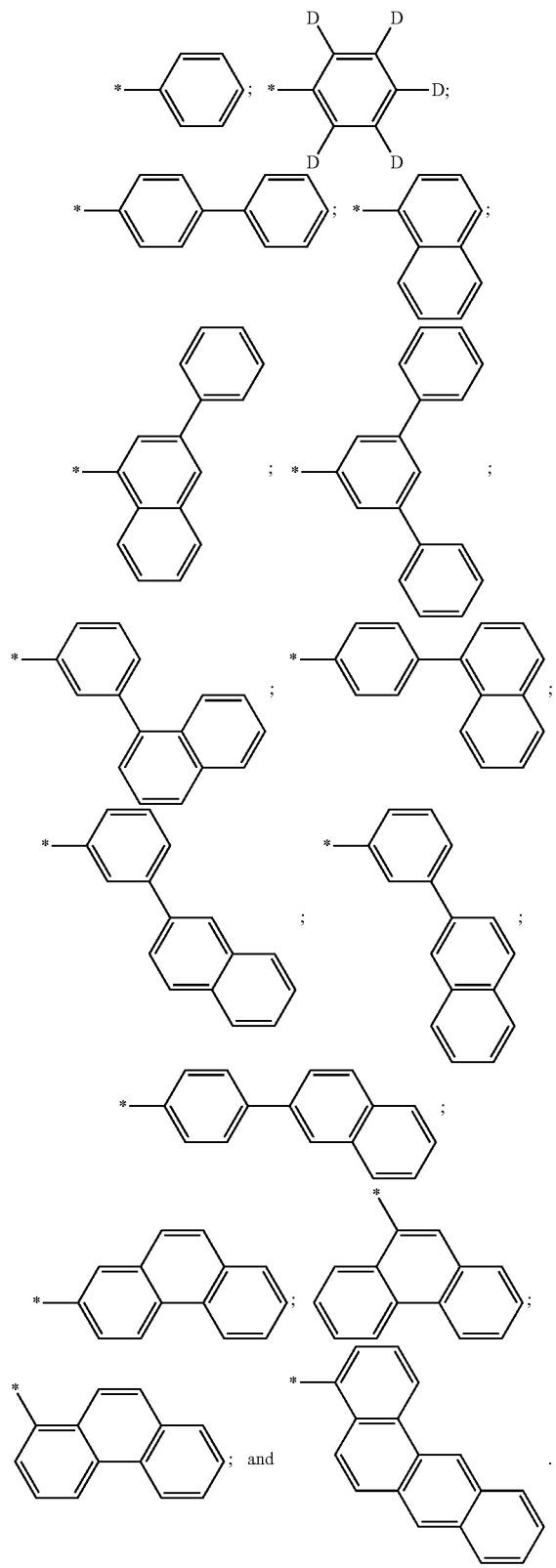

Preferably, the arylene groups having 6 to 60 ring carbon atoms represented by $L^1$, $L^2$ and $L^3$ in Formulae (I) to (I′′′) are each independently selected from the group consisting of:

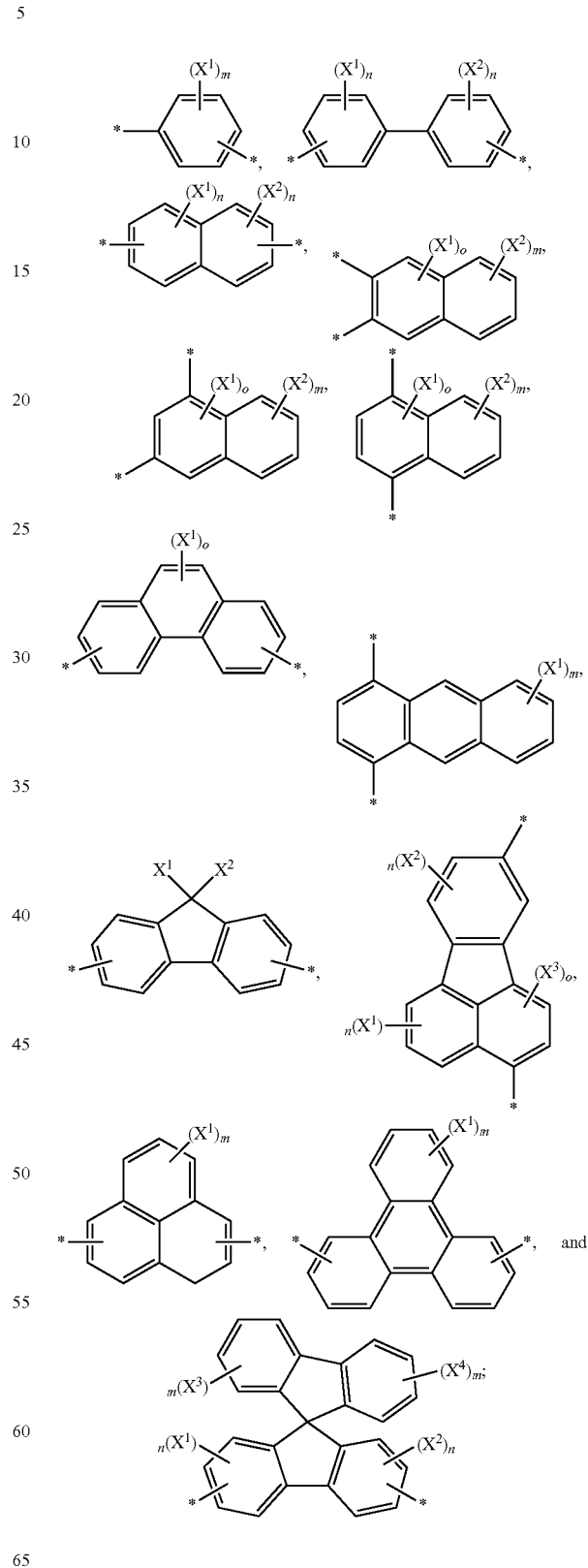

wherein m is an integer from 1 to 4, n is an integer from 1 to 3, and o is an integer 1 or 2;

$X^1$ to $X^4$ are each independently selected from the group consisting of: a hydrogen atom, a deuterium atom, a halo group, a cyano group, a nitro group, an alkyl group having 1 to 12 carbon atoms, an alkenyl group having 2 to 12 carbon atoms, an alkynyl group having 2 to 12 carbon atoms, an alkoxy group having 1 to 12 carbon atoms, an aryl group having 6 to 30 ring carbon atoms, a heteroaryl group having 3 to 30 ring carbon atoms, and an aryloxy group having 6 to 30 ring carbon atoms.

In this specification, said "arylene group having 6 to 60 ring carbon atoms" denoted by $L^1$, $L^2$, $L^3$, $L'^1$, $L'^2$, or $L'^3$ may be an unsubstituted arylene group having 6 to 60 ring carbon atoms or an arylene group having 6 to 60 ring carbon atoms substituted with a substituent. The substituent on the arylene group may be any one of $X^1$ to $X^4$ as stated above.

In this specification, said "aryl group" may be an unsubstituted aryl group or an aryl group substituted with a substituent, said "heteroaryl group" may be an unsubstituted heteroaryl group or a heteroaryl group substituted with a substituent. The substituent on the aryl group may be any one of $X^1$ to $X^4$ as stated above. The substituent on the heteroaryl group may be similar to any one of $X^1$ to $X^4$ as stated above.

In this specification, said "alkyl group" may be an unsubstituted alkyl group or an alkyl group substituted with a substituent, said "alkenyl group" may be an unsubstituted alkenyl group or an alkenyl group substituted with a substituent, and said "alkynyl group" may be an unsubstituted alkynyl group or an alkynyl group substituted with a substituent. The substituent on the alkyl group, alkenyl group, or alkynyl group may be, for example, but not limited to a deuterium atom.

In this specification, said "cycloalkyl group" may be an unsubstituted cycloalkyl group or a cycloalkyl group substituted with a substituent, and said "heterocycloalkyl group" may be an unsubstituted heterocycloalkyl group or a heterocycloalkyl group substituted with a substituent. The substituent on the cycloalkyl group or heterocycloalkyl group may be, for example, but not limited to a deuterium atom, an alkyl group having 1 to 12 carbon atoms, an alkenyl group having 2 to 12 carbon atoms, or an alkynyl group having 2 to 12 carbon atoms.

For example, the compound may be selected from the group consisting of:

Compound 1

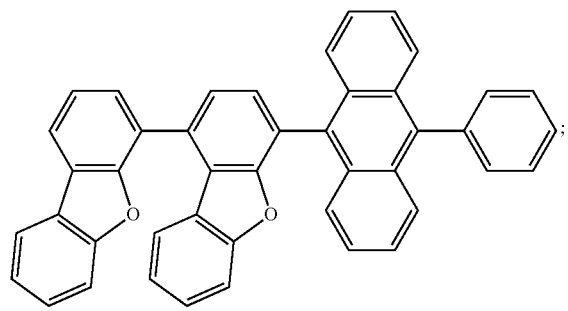

Compound 2

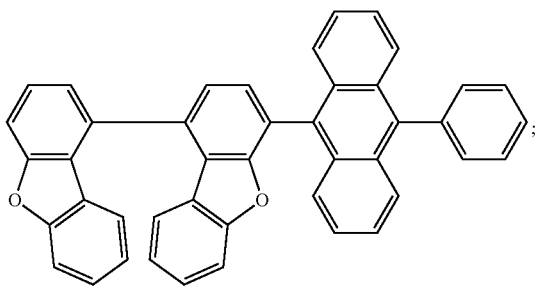

Compound 3

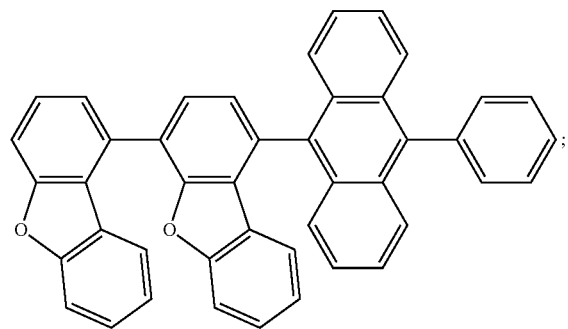

Compound 4

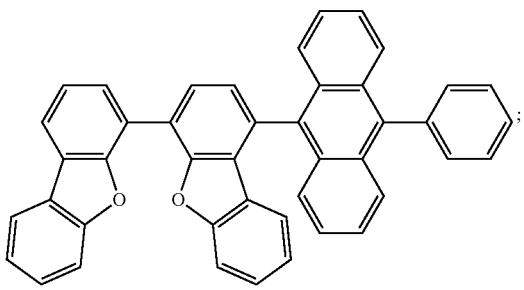

Compound 5

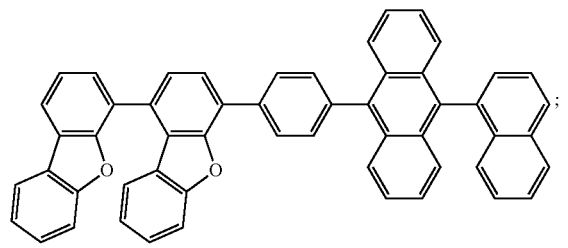

Compound 6

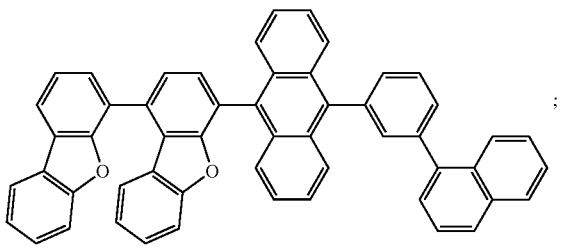

-continued
Compound 7
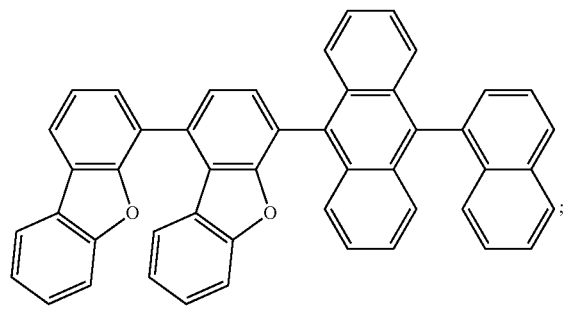
Compound 8
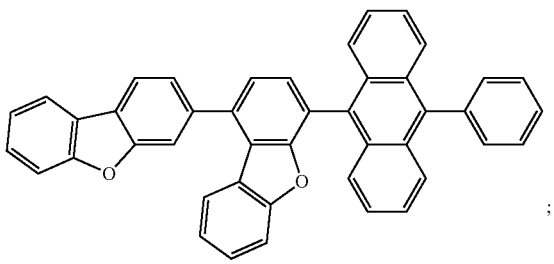
Compound 9
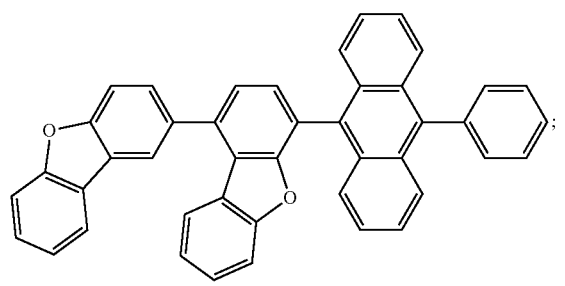
Compound 10
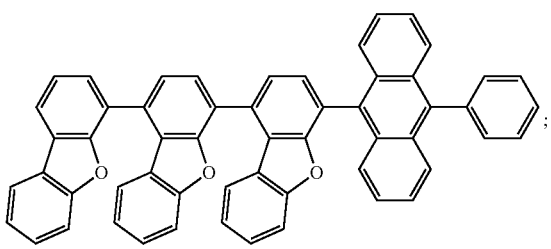
Compound 11
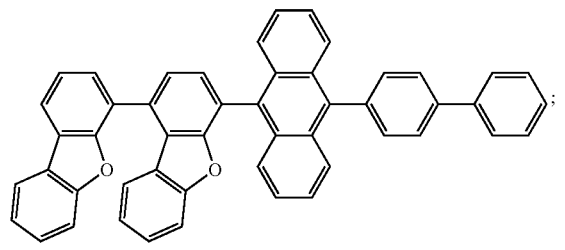
Compound 12
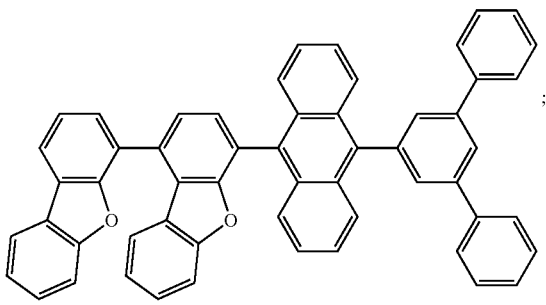
Compound 13
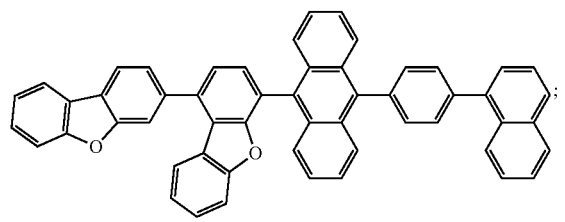
Compound 14
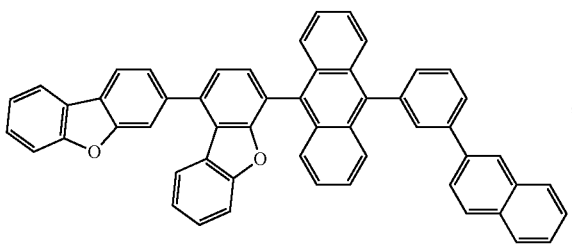
Compound 15
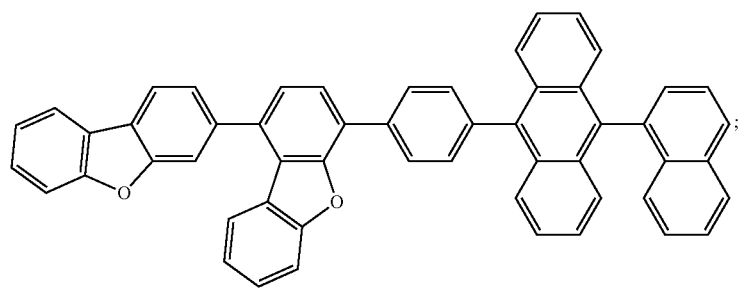

Compound 16
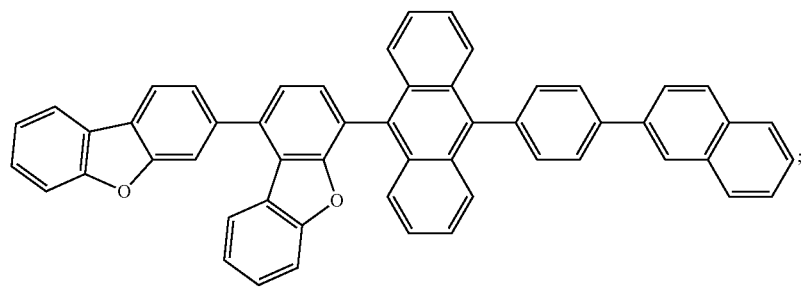
Compound 17
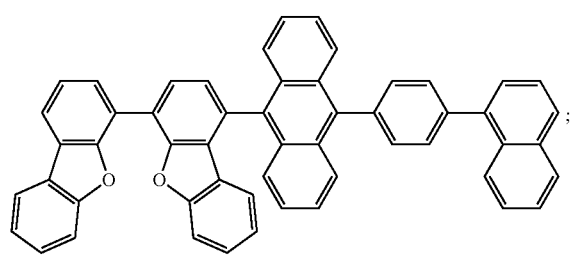
Compound 18
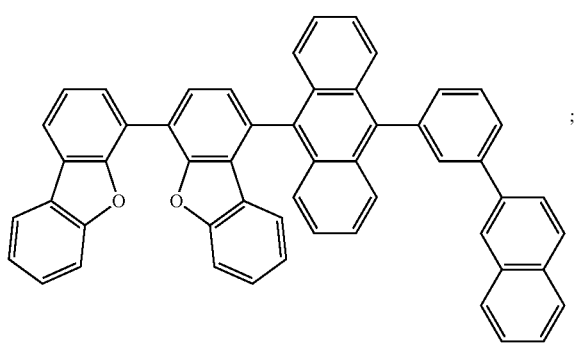
Compound 19
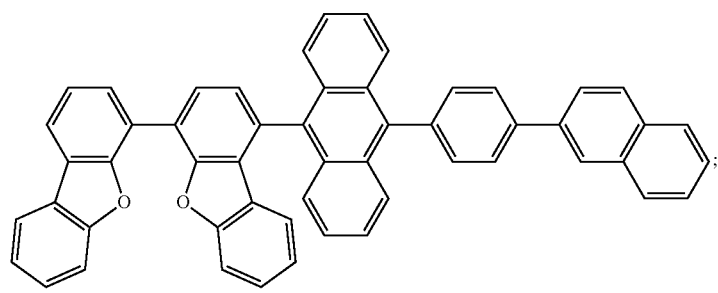
Compound 20
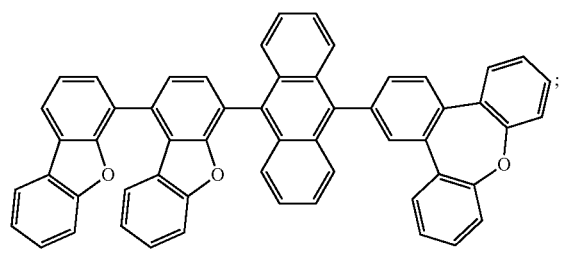
Compound 21
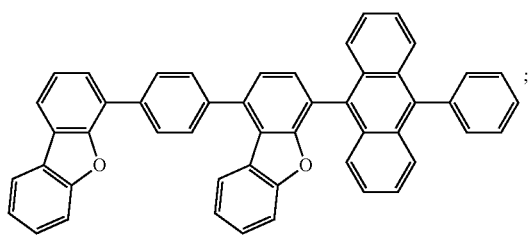
Compound 22
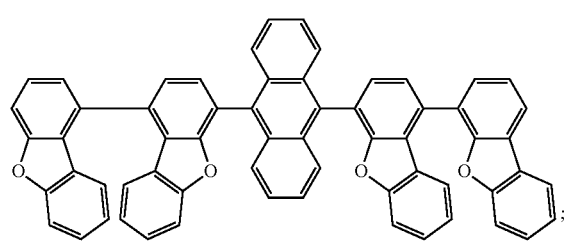
Compound 23
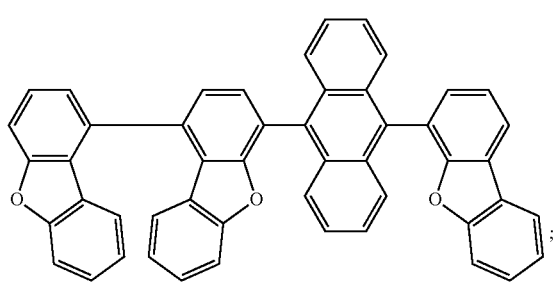

-continued
Compound 24
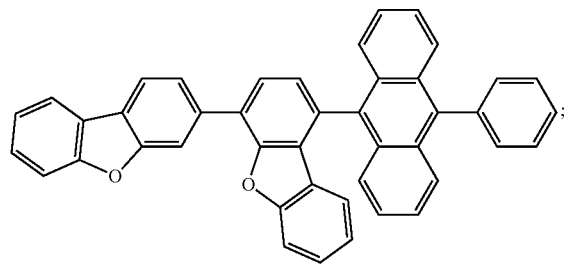
Compound 25
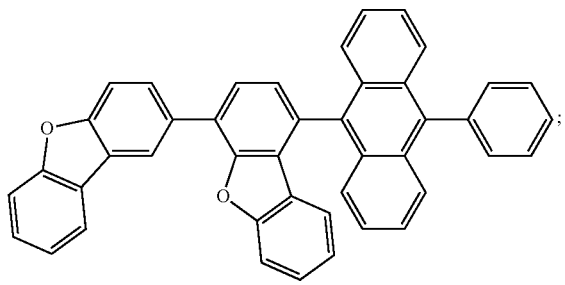
Compound 26
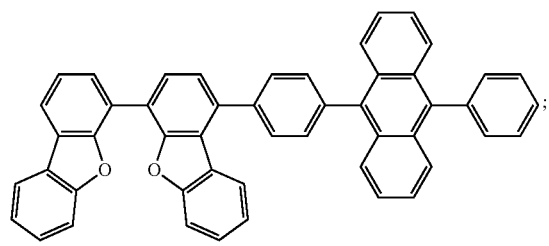
Compound 27
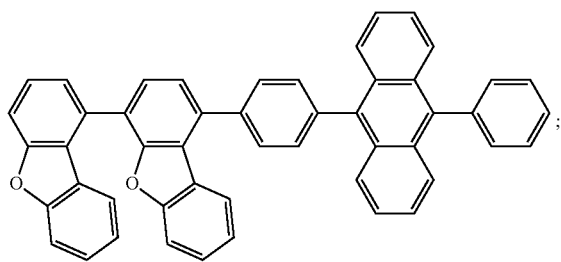
Compound 28
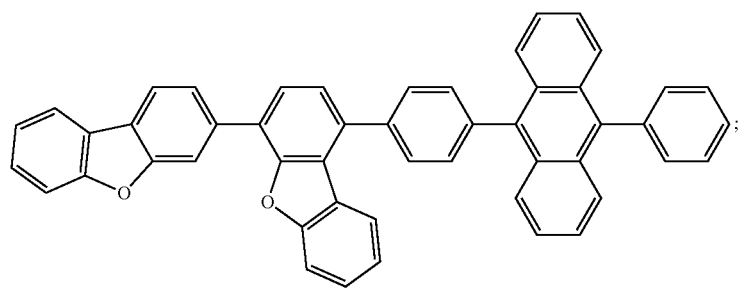
Compound 29
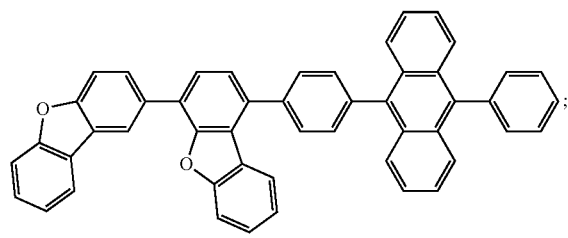
Compound 30
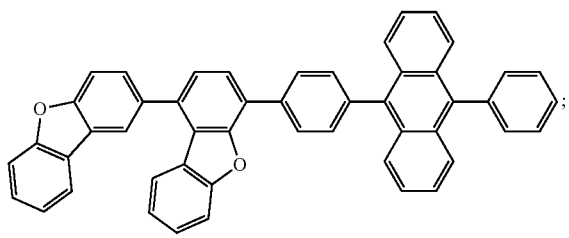
Compound 31
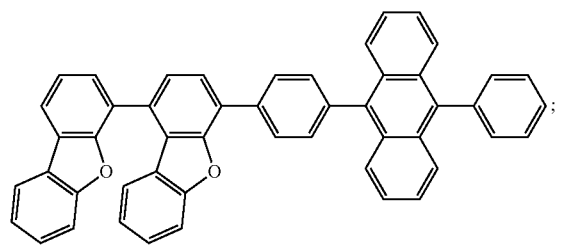
Compound 32
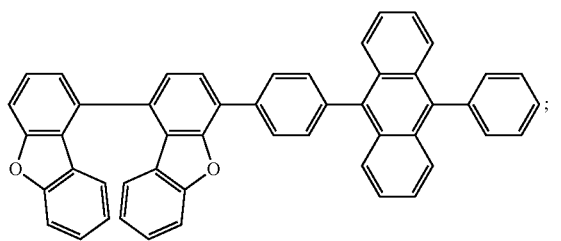

-continued
Compound 33
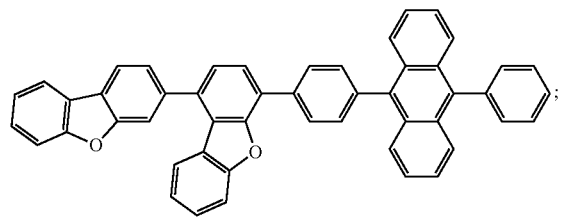
Compound 34
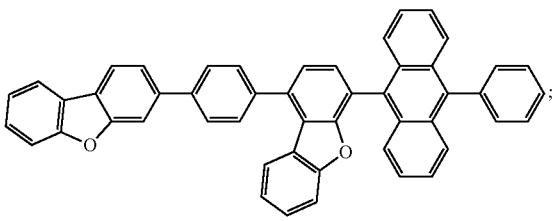
Compound 35
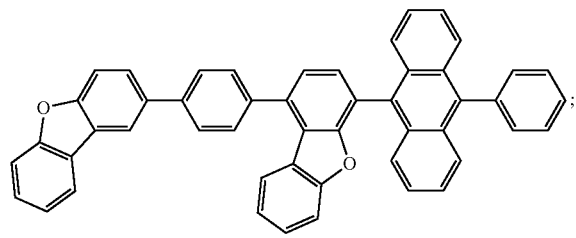
Compound 36
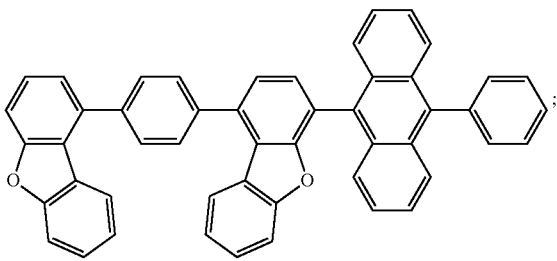
Compound 37
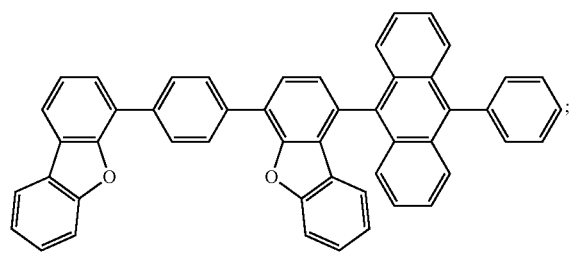
Compound 38
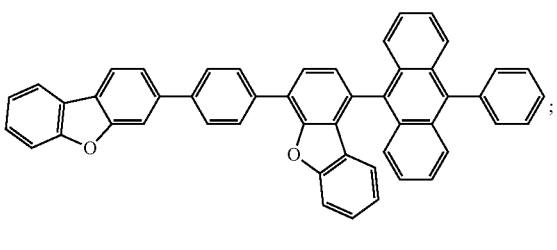
Compound 39
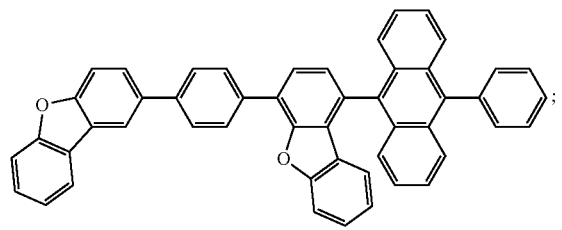
Compound 40
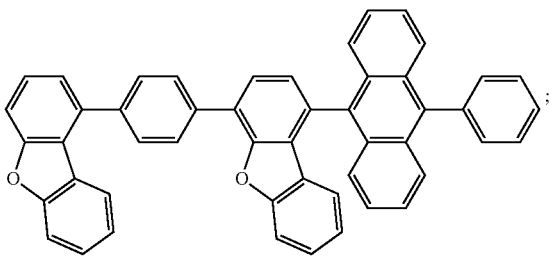
Compound 41
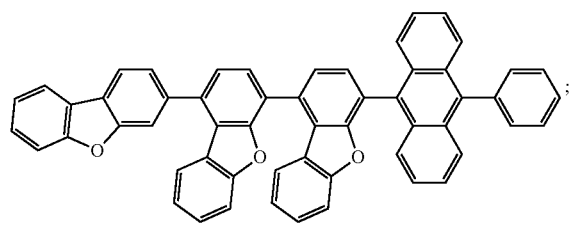
Compound 42
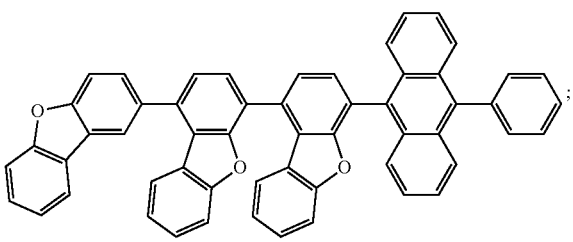
Compound 43
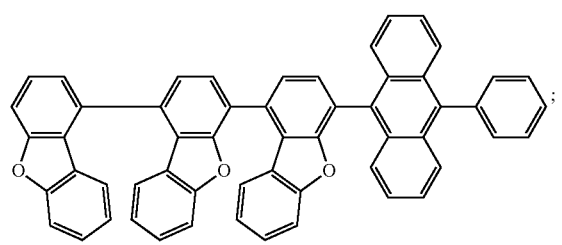
Compound 44
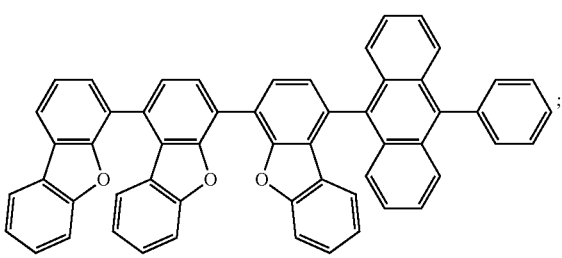

-continued
Compound 45
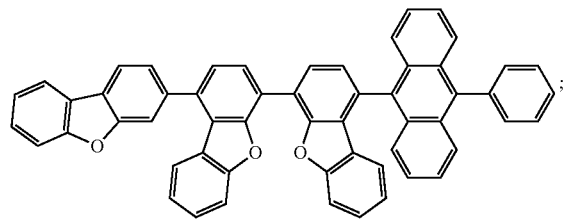
Compound 46
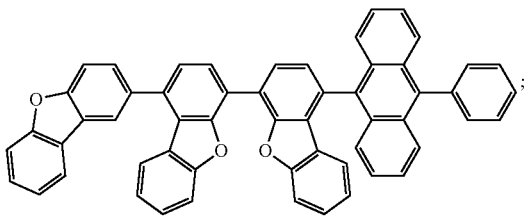
Compound 47
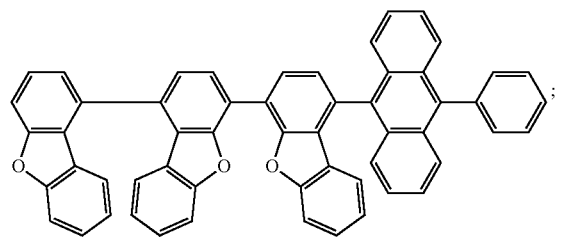
Compound 48
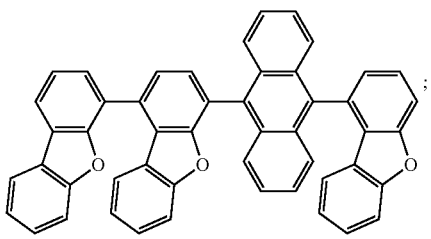
Compound 49
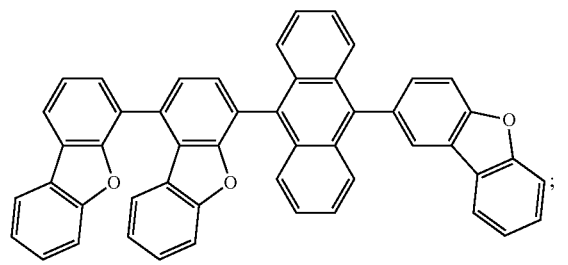
Compound 50
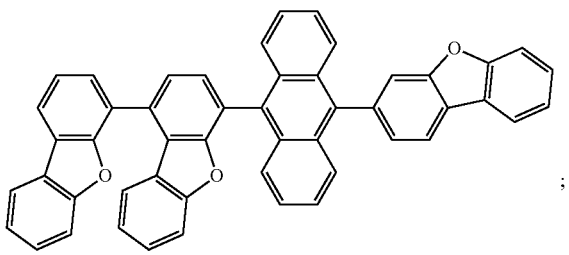
Compound 51
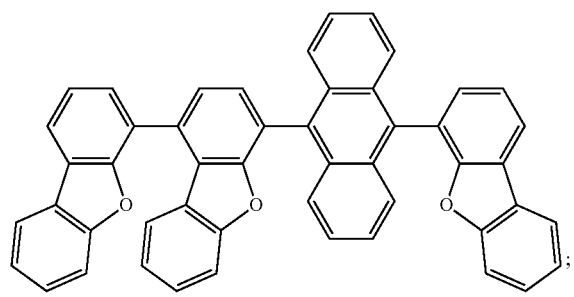
Compound 52
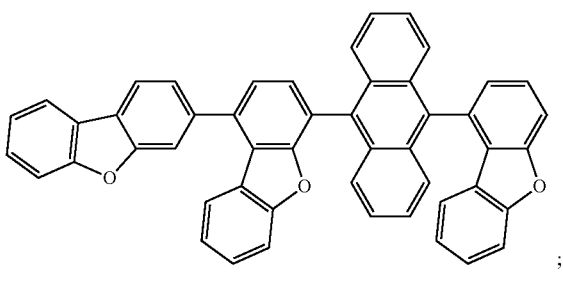
Compound 53
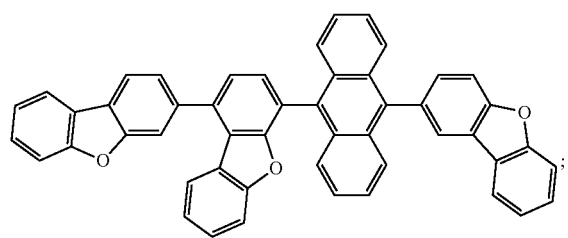
Compound 54
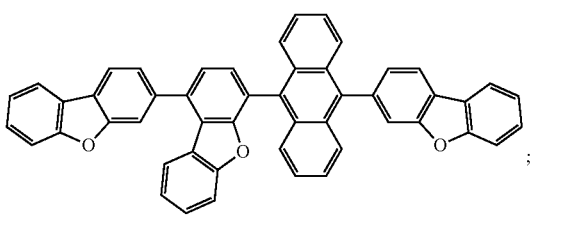

Compound 55
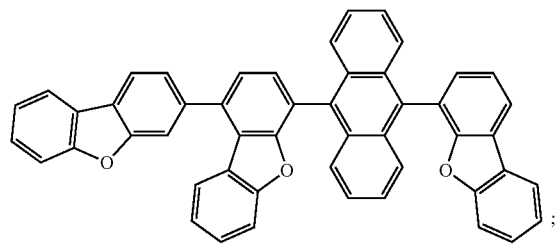
Compound 56
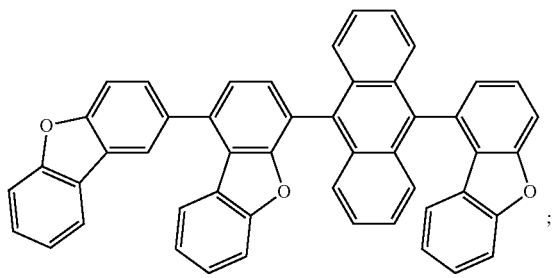
Compound 57
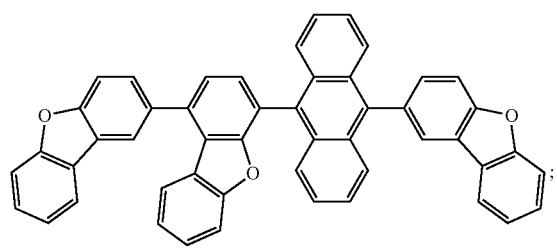
Compound 58
Compound 59
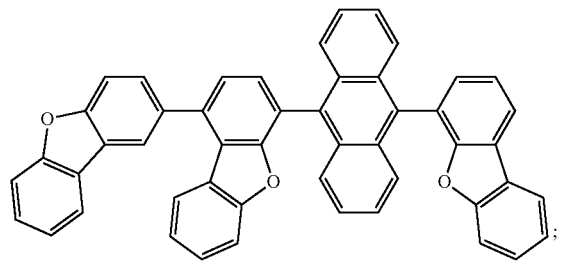
Compound 60
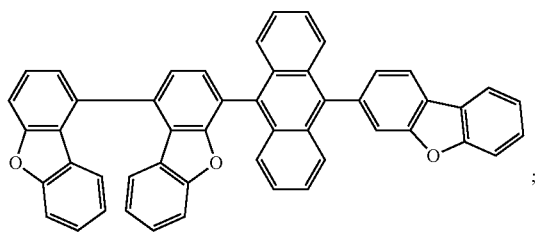
Compound 61
Compound 62
Compound 63
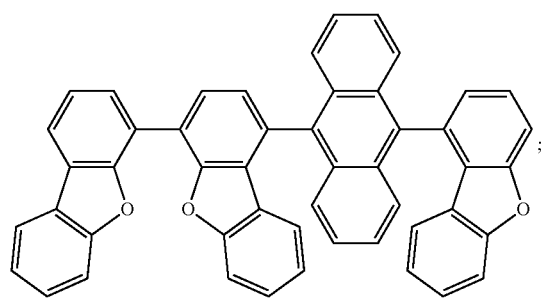
Compound 64
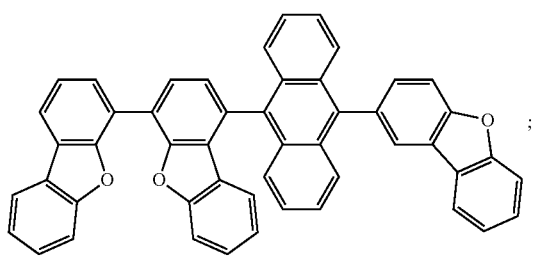

-continued
Compound 65
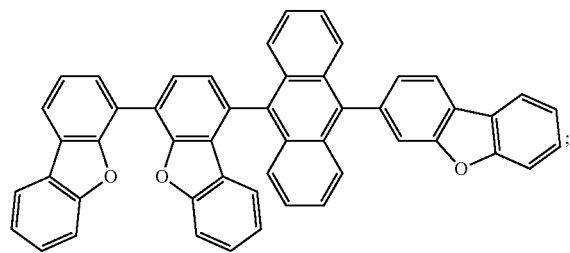
Compound 66
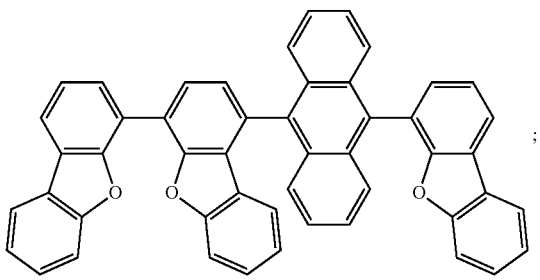
Compound 67
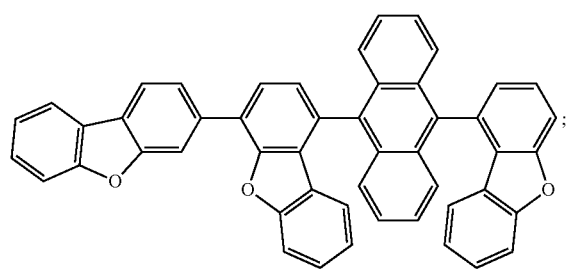
Compound 68
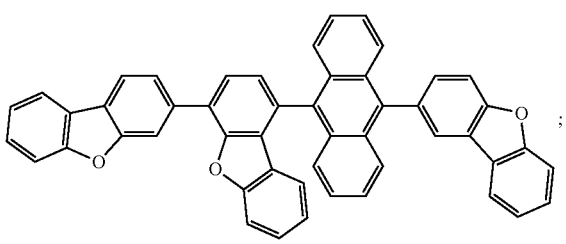
Compound 69
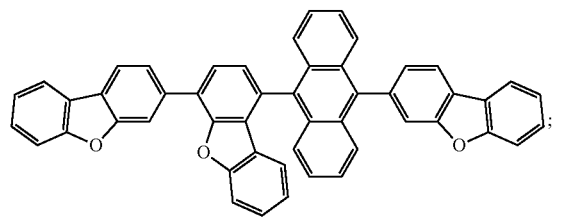
Compound 70
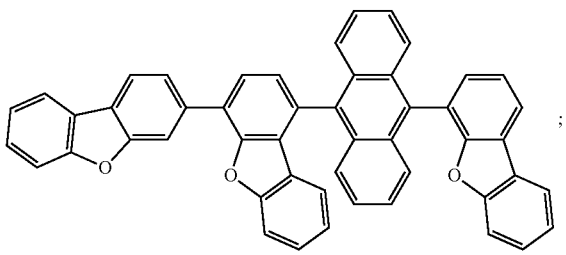
Compound 71
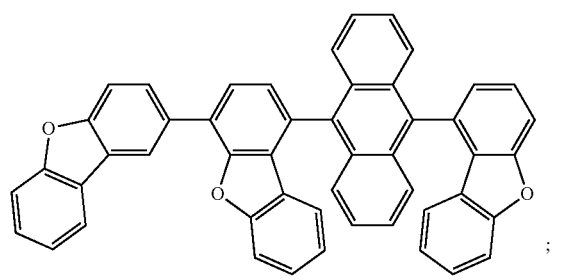
Compound 72
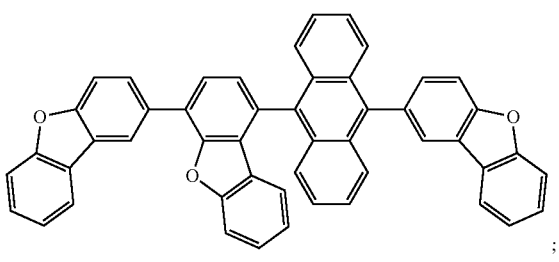
Compound 73
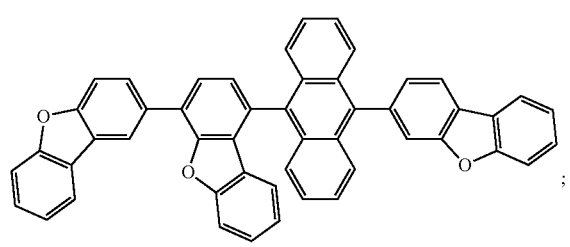
Compound 74
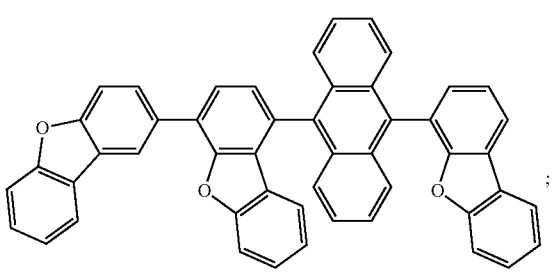

-continued
Compound 75
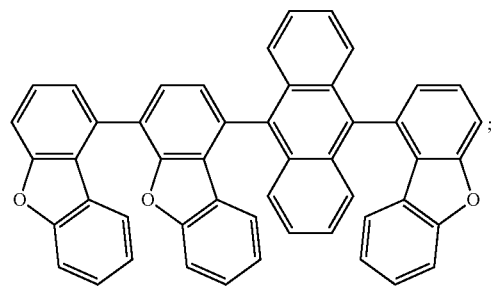
Compound 76
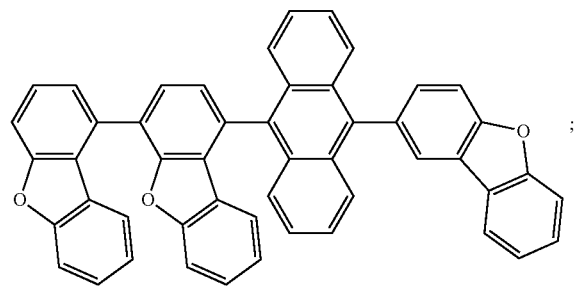
Compound 77
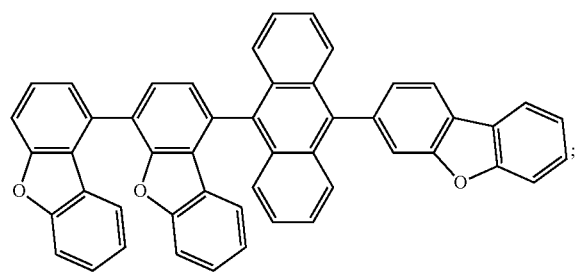
Compound 78
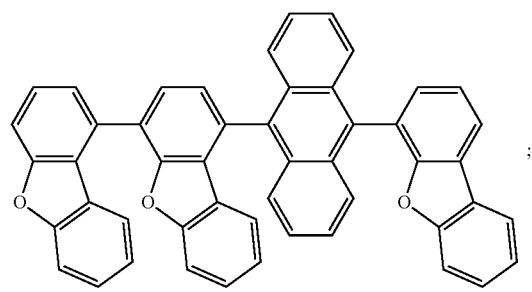
Compound 79
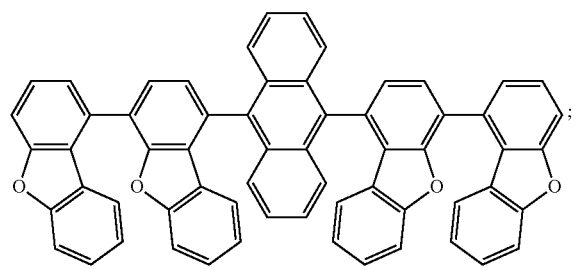
Compound 80
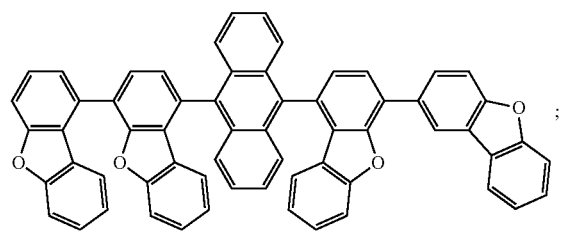
Compound 81
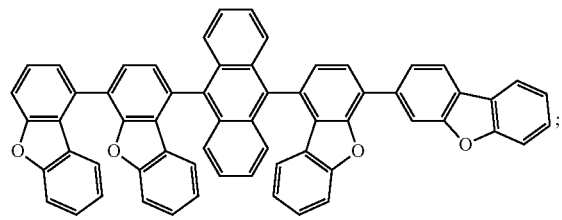
Compound 82
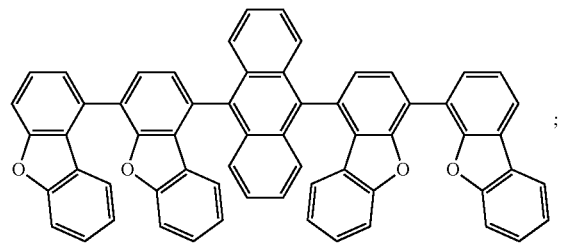
Compound 83
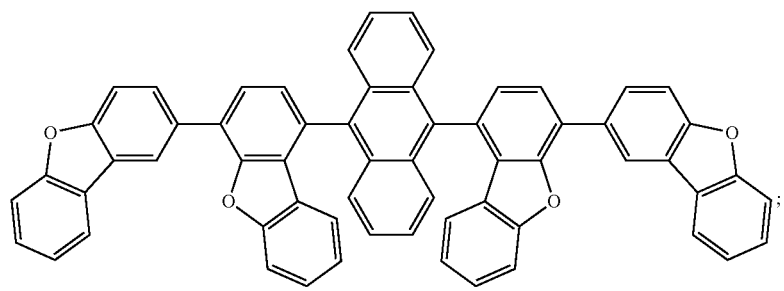

Compound 84
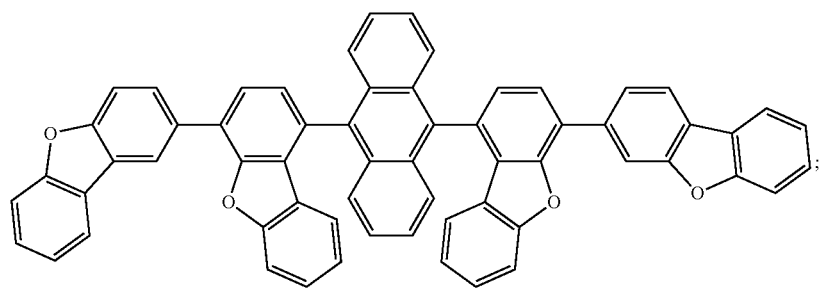
Compound 85
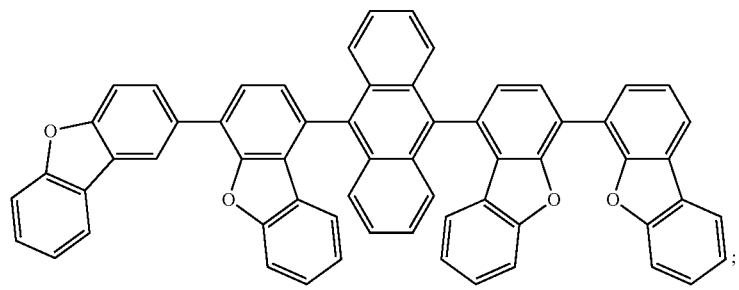
Compound 86
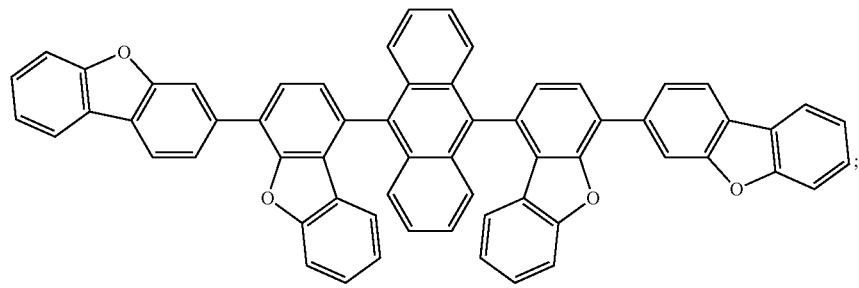
Compound 87
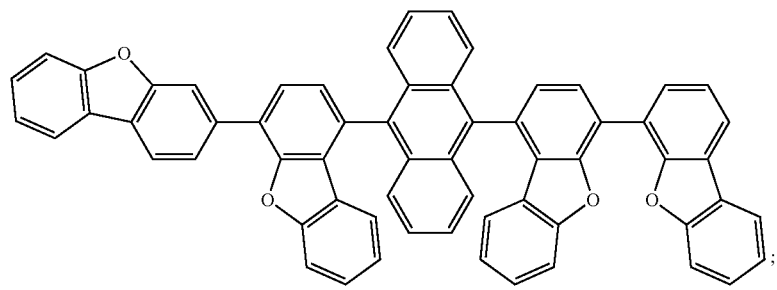
Compound 88
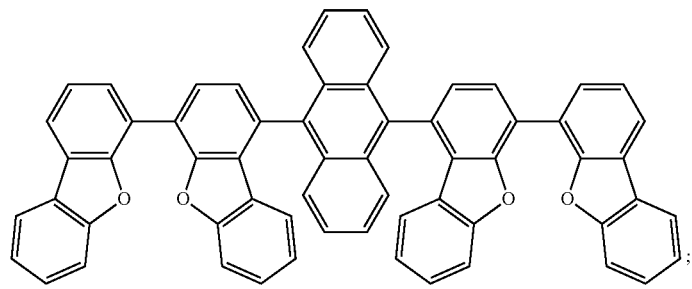

Compound 89
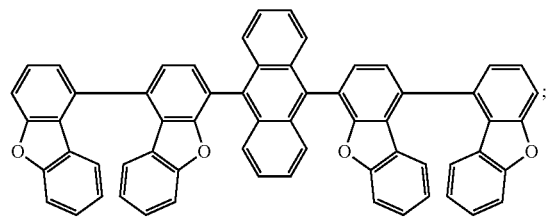
Compound 90
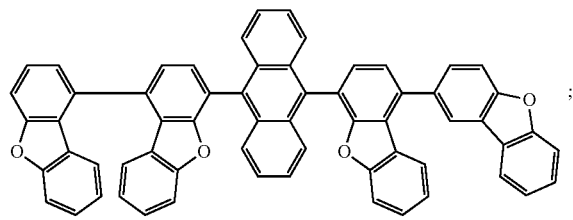
Compound 91
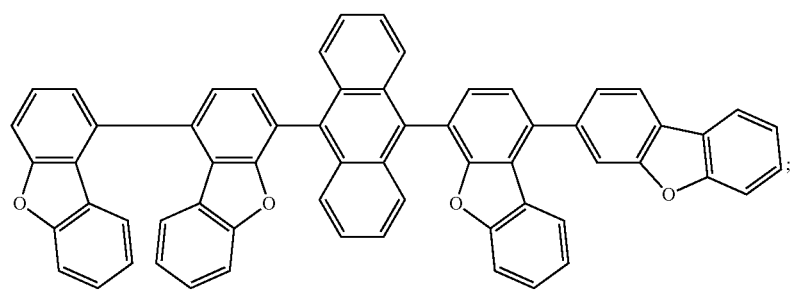
Compound 92
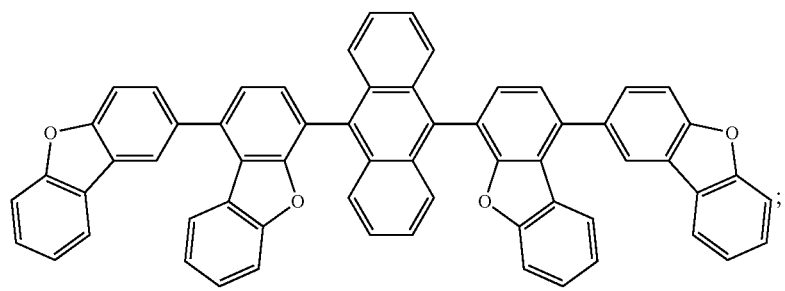
Compound 93
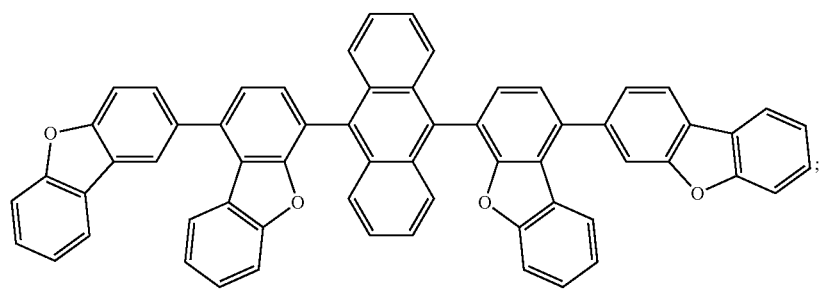
Compound 94
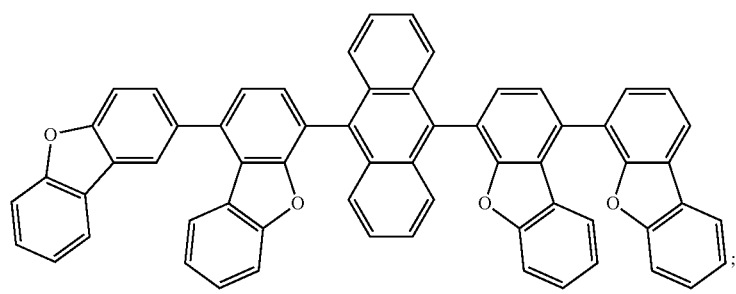

-continued
Compound 95
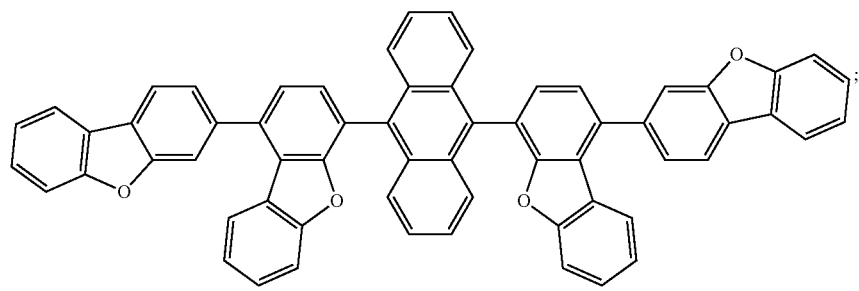
Compound 96
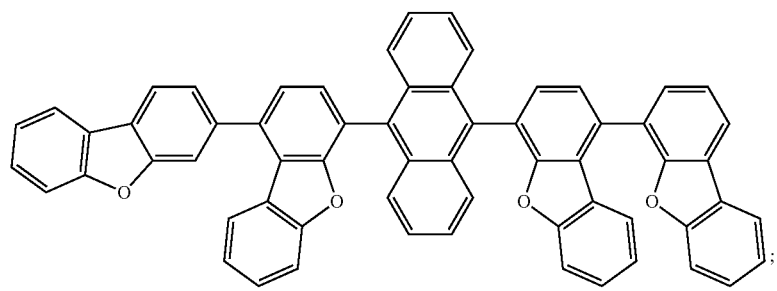
Compound 97
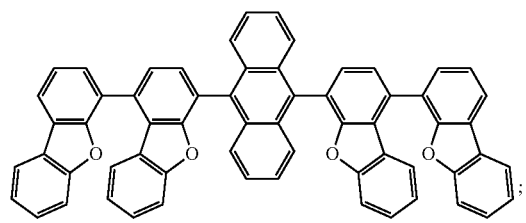
Compound 98
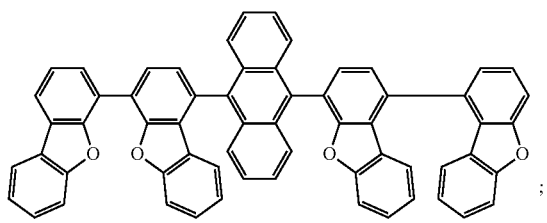
Compound 99
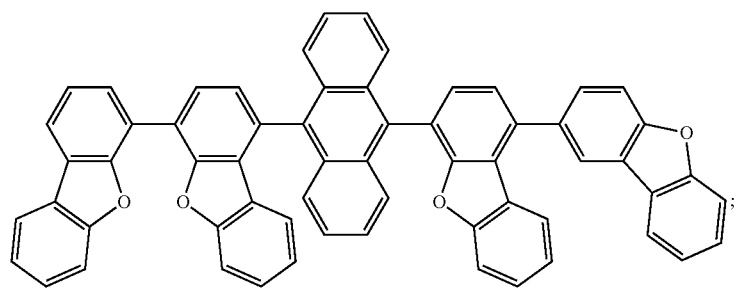
Compound 100
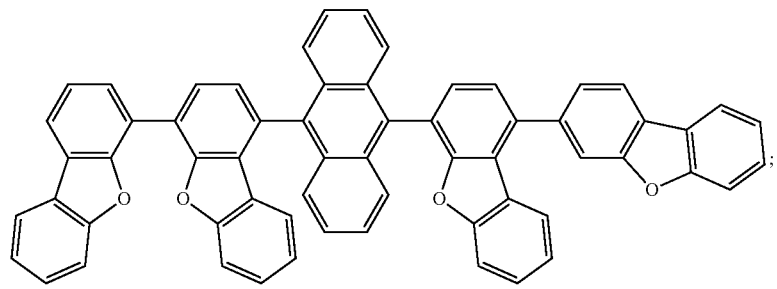
Compound 101
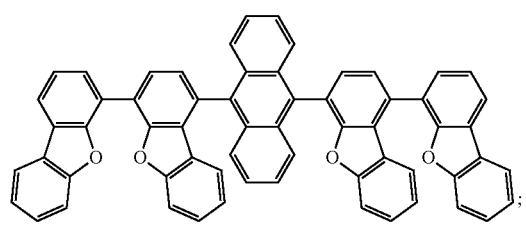
Compound 102
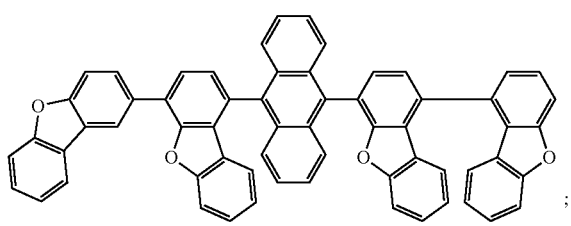

-continued
Compound 103
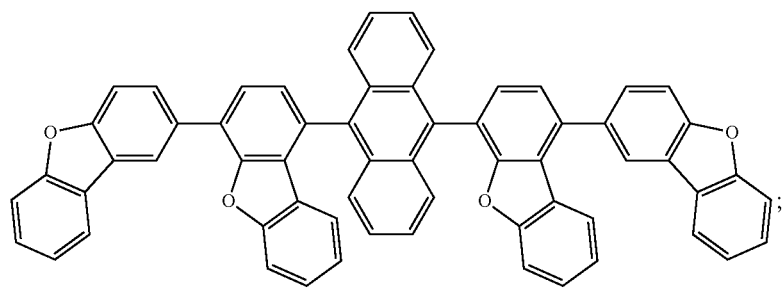
Compound 104
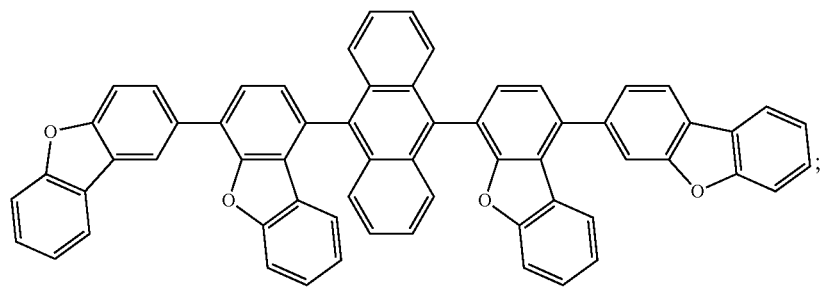
Compound 105
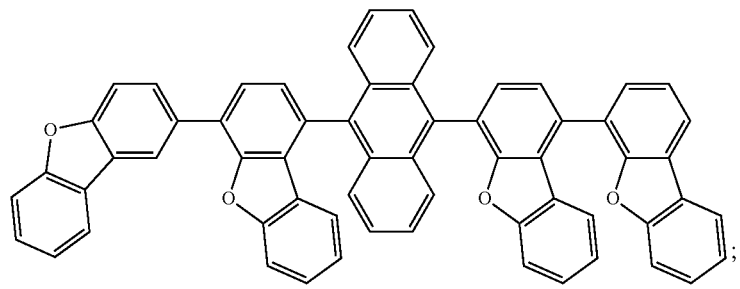
Compound 106
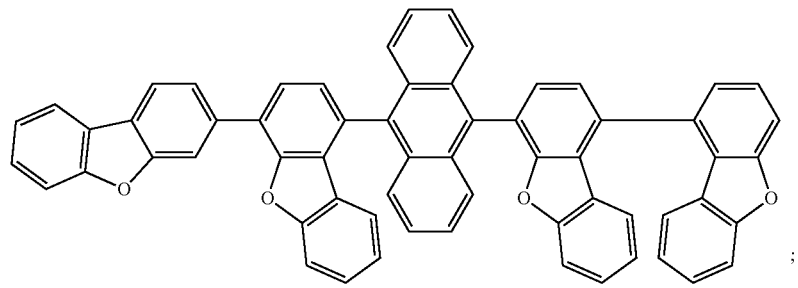
Compound 107
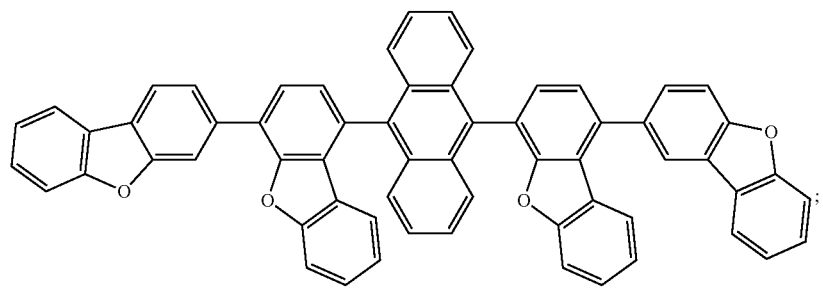

-continued
Compound 108
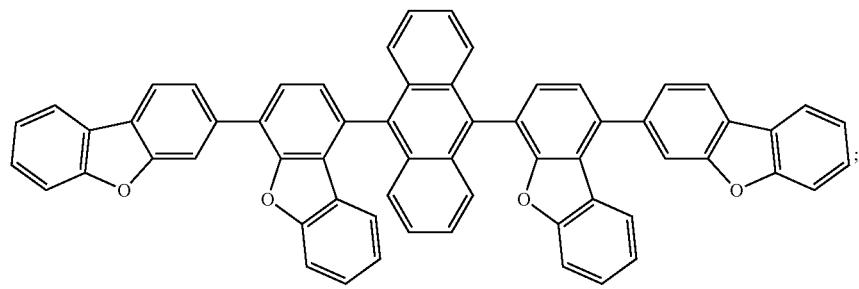
Compound 109
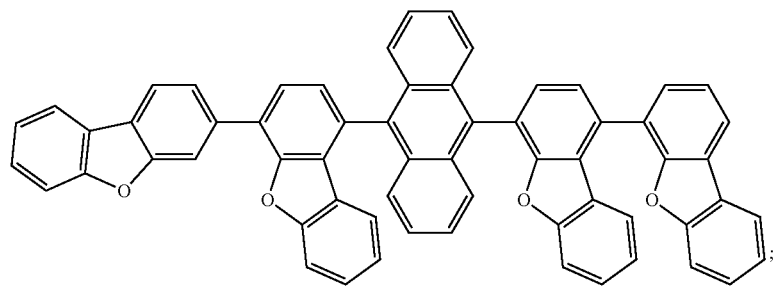
Compound 110
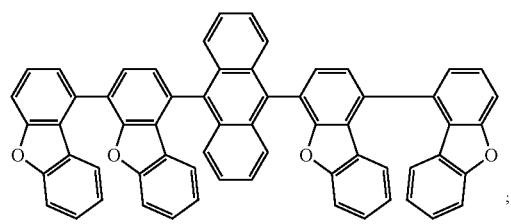
Compound 111
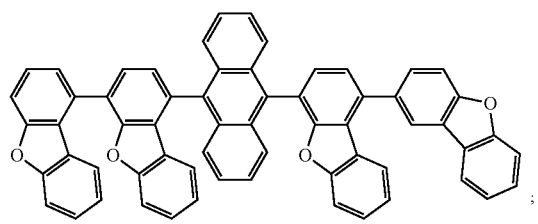
Compound 112
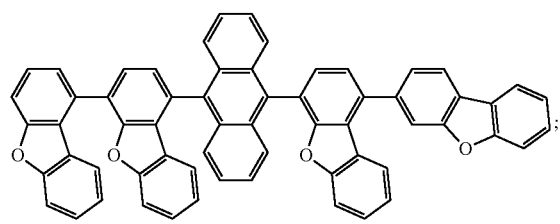
Compound 113
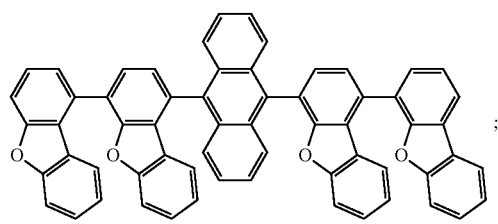
Compound 114
Compound 115
Compound 116
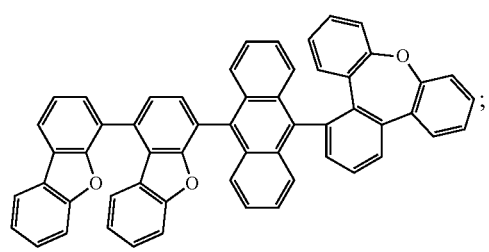
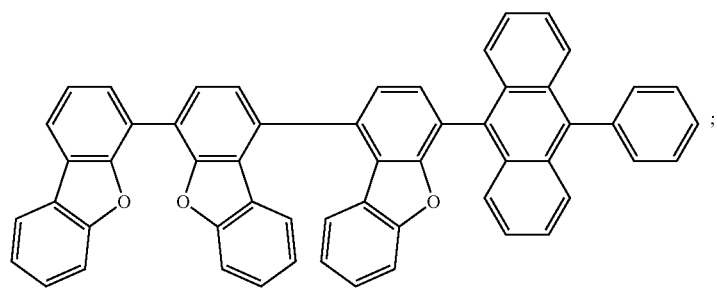

-continued
Compound 117
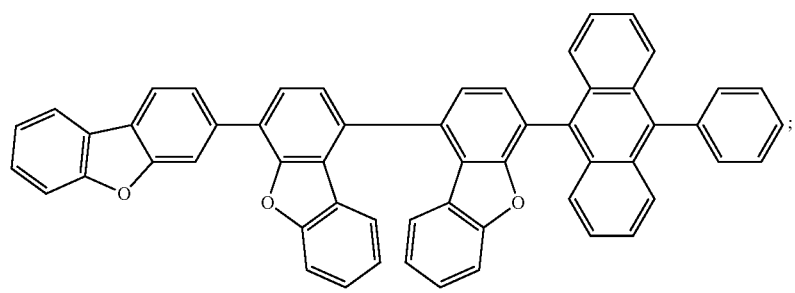
Compound 118
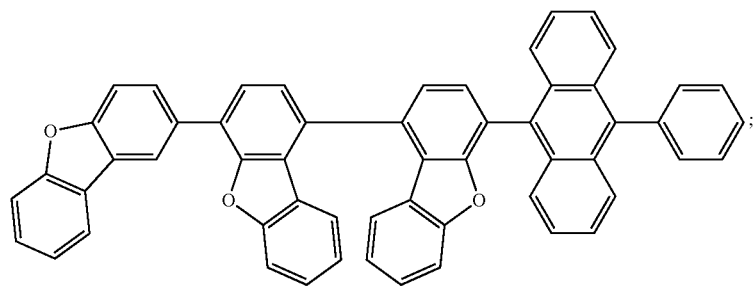
Compound 119
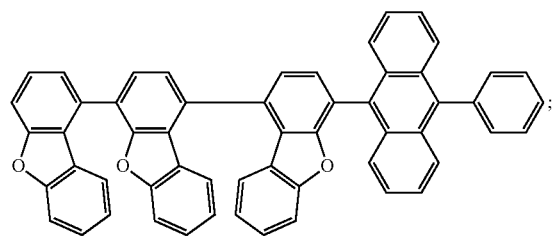
Compound 120
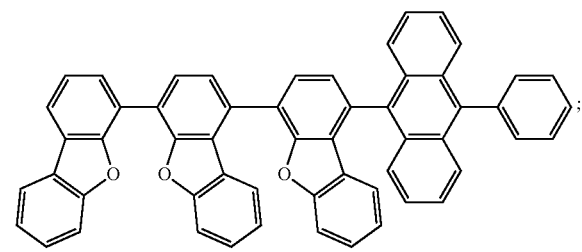
Compound 121
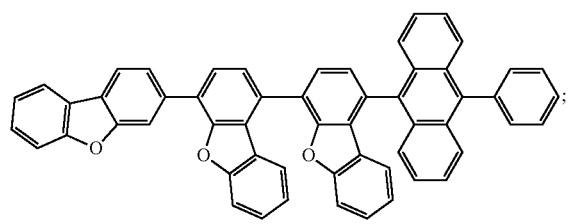
Compound 122
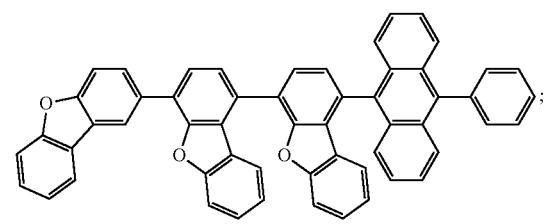
Compound 123
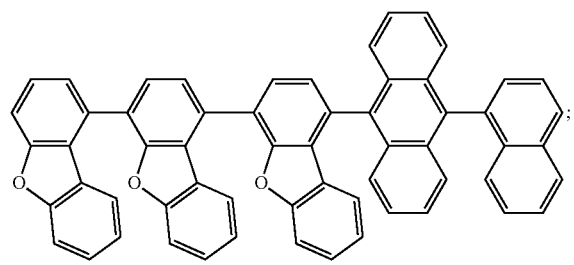
Compound 124
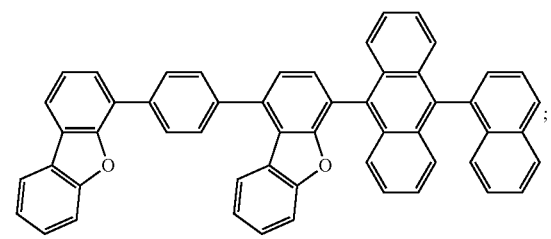

Compound 125
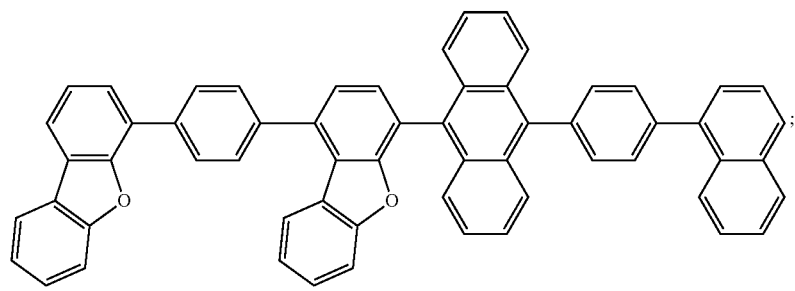
Compound 126
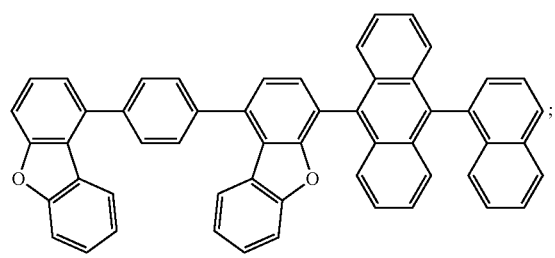
Compound 127
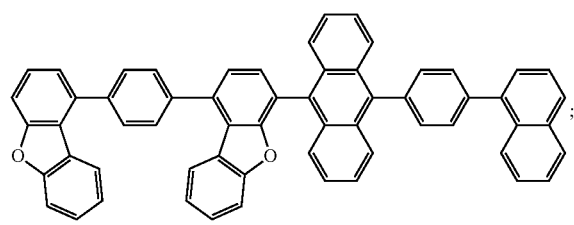
Compound 128
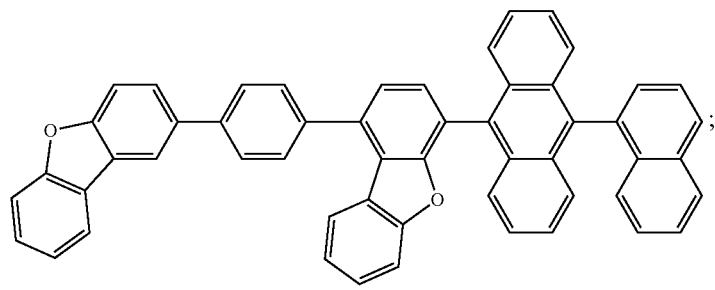
Compound 129
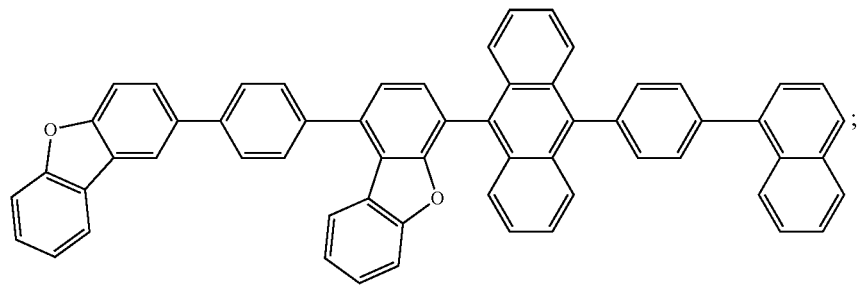
Compound 130
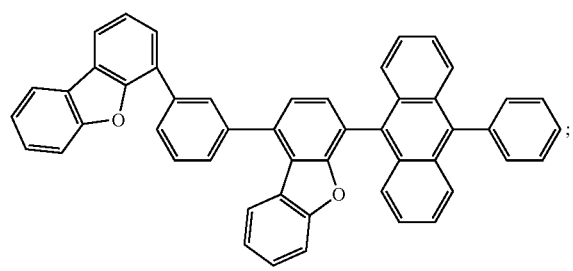
Compound 131
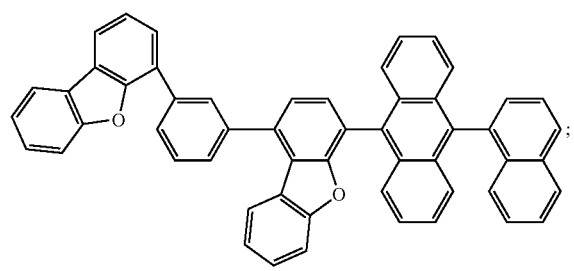

Compound 132
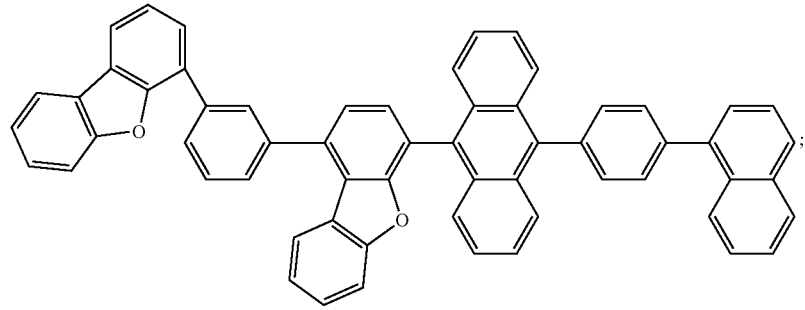
Compound 133                              Compound 134
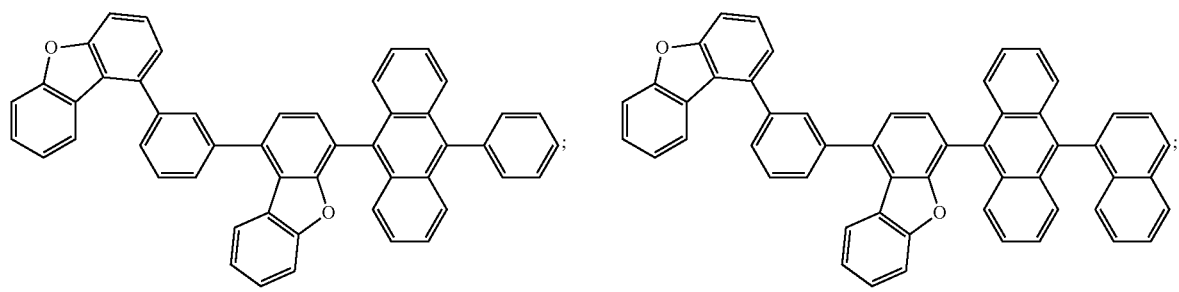
Compound 135                              Compound 136
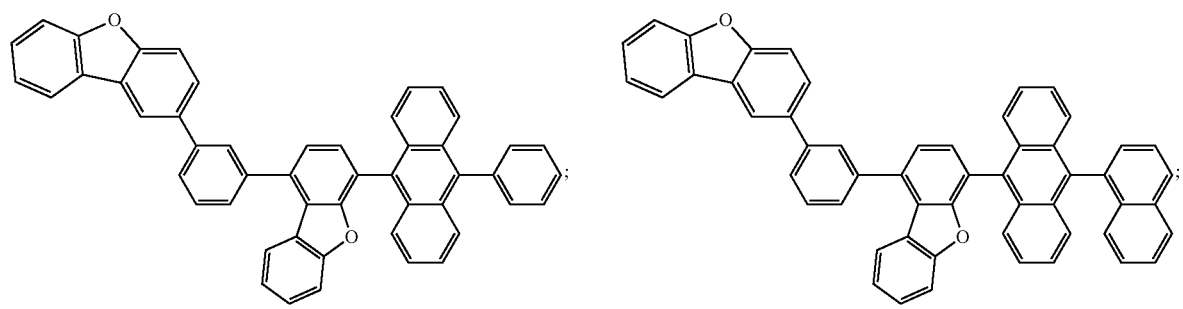
Compound 137                              Compound 138
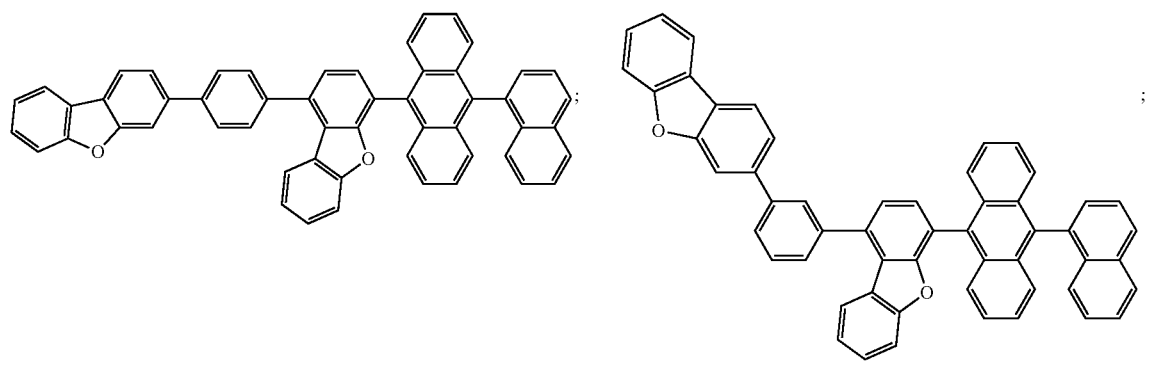

-continued
Compound 139
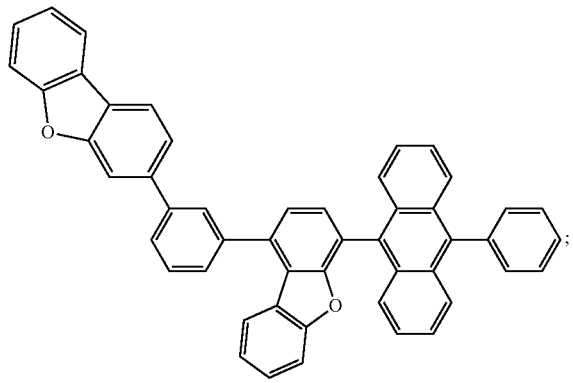
Compound 140
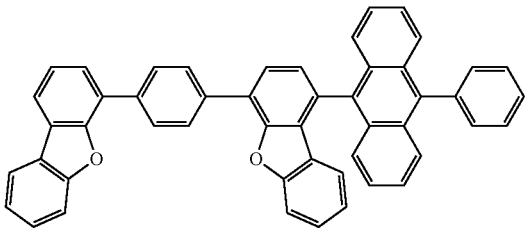
Compound 141
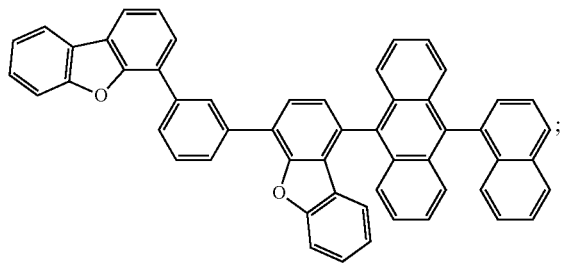
Compound 142
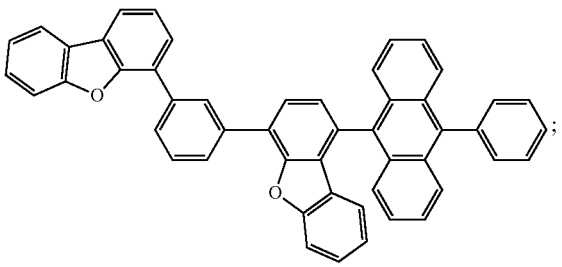
Compound 143
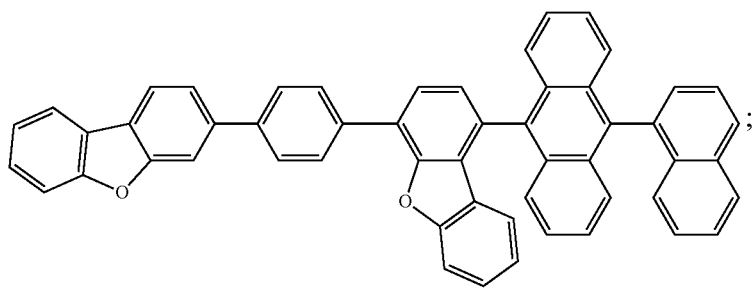
Compound 144
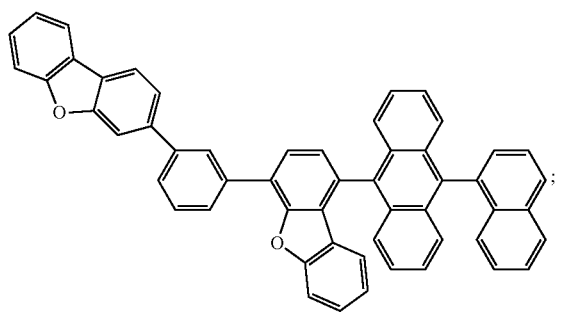
Compound 145
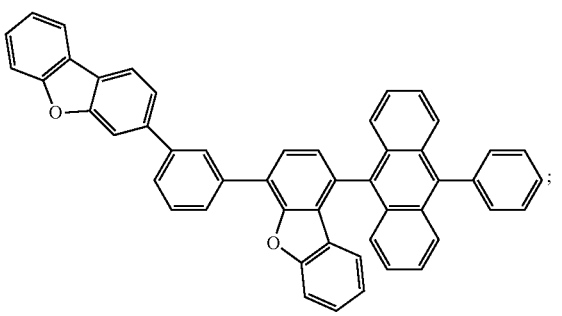
Compound 146
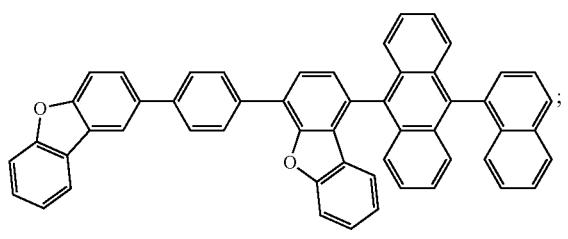
Compound 147
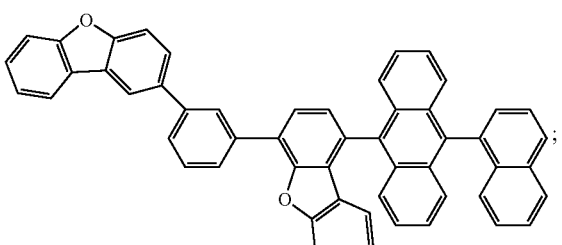

-continued
Compound 148
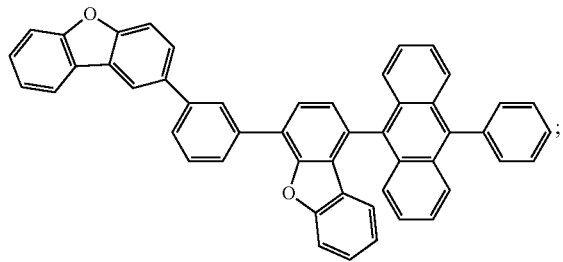
Compound 149
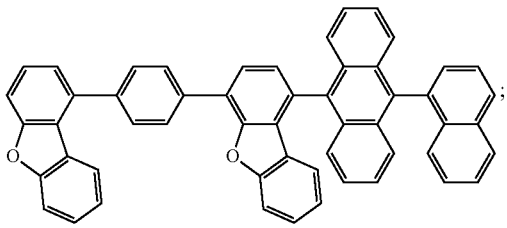
Compound 150
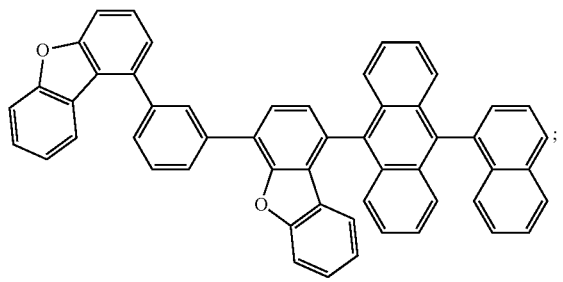
Compound 151
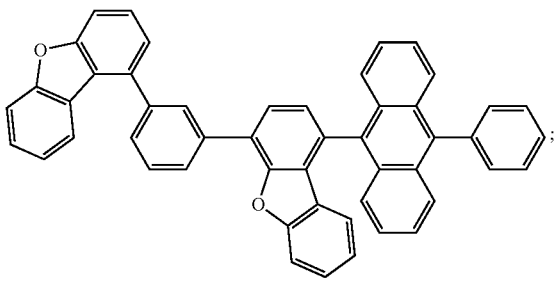
Compound 152
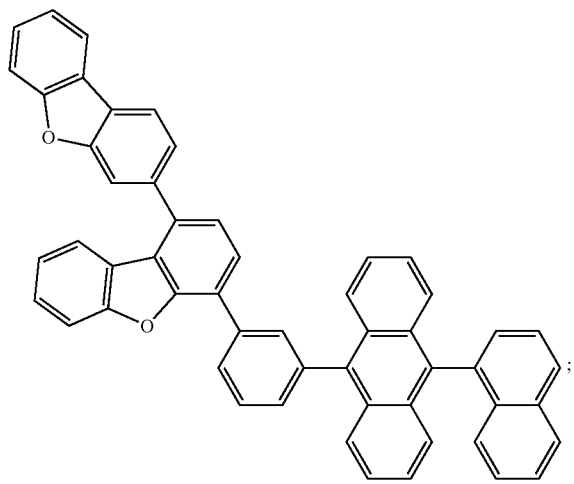
Compound 153
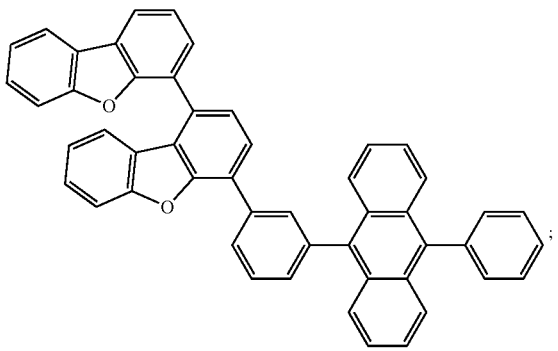
Compound 154
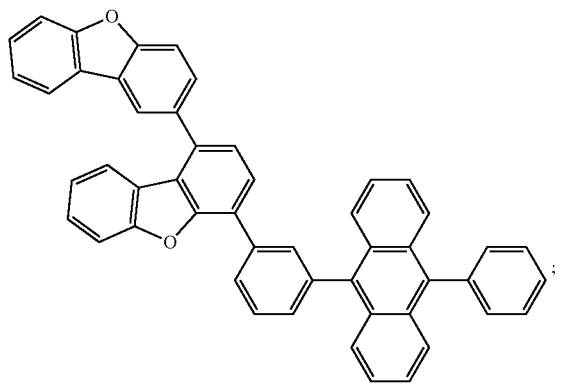
Compound 155
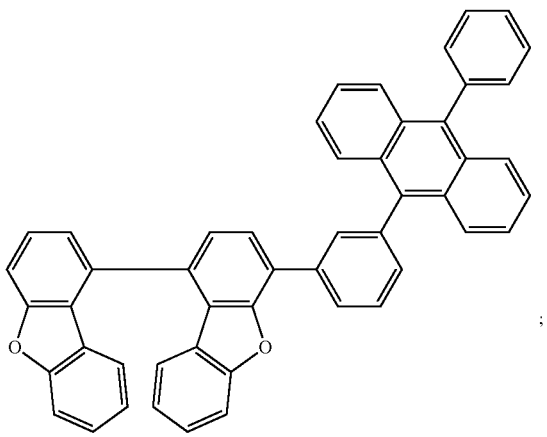

-continued
Compound 156
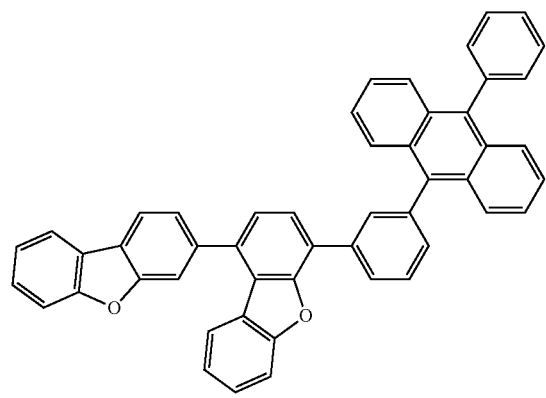
Compound 157
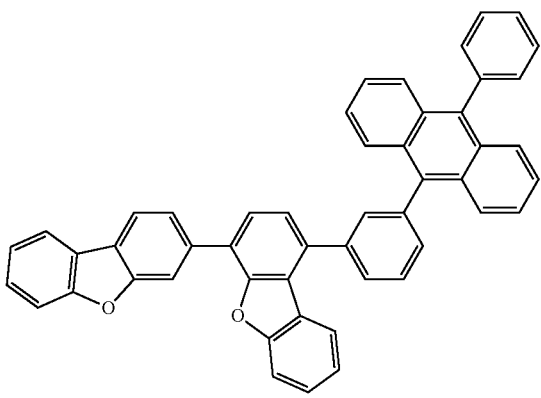
Compound 158
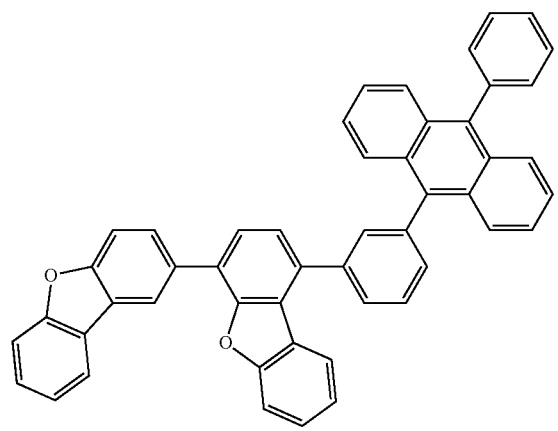
Compound 159
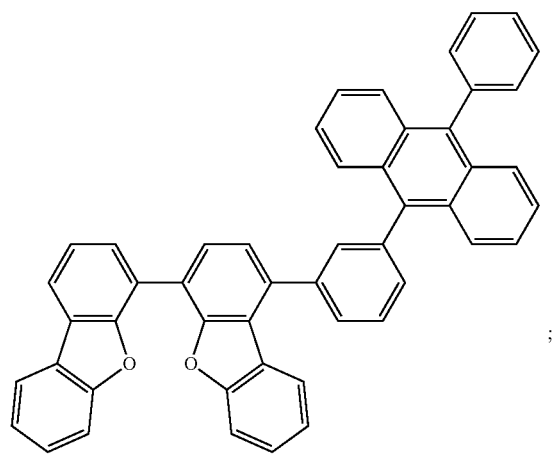
Compound 160
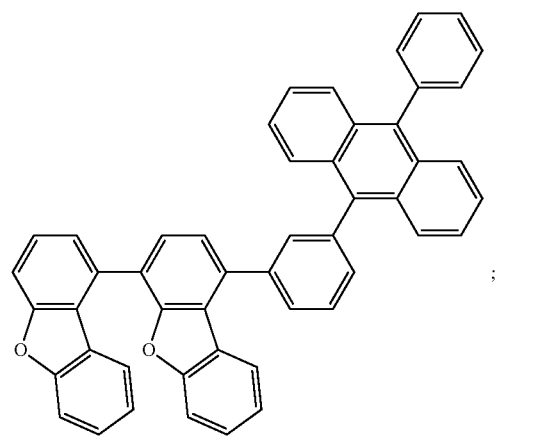
Compound 161
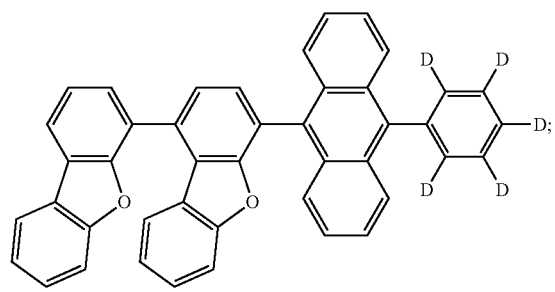
Compound 162
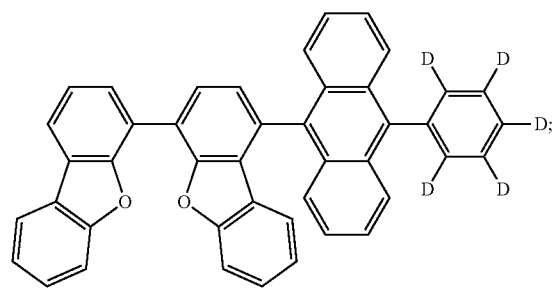
Compound 163
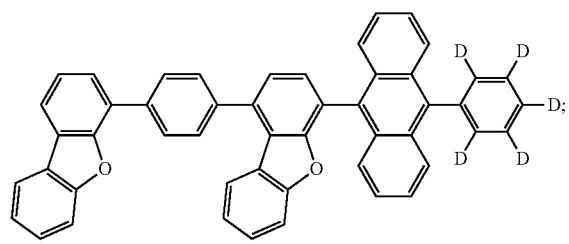

-continued
Compound 164
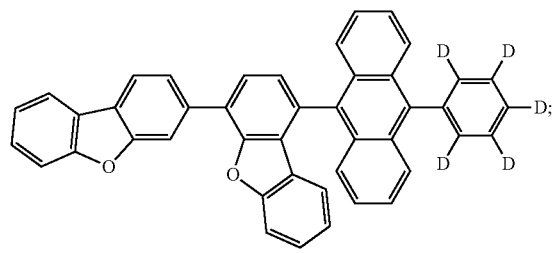
Compound 165
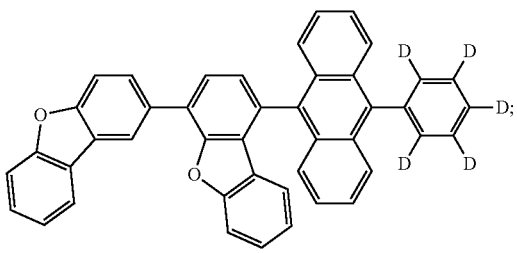
Compound 166
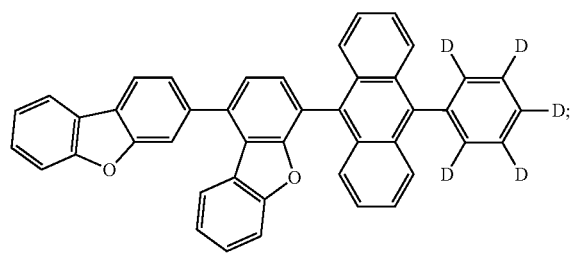
Compound 167
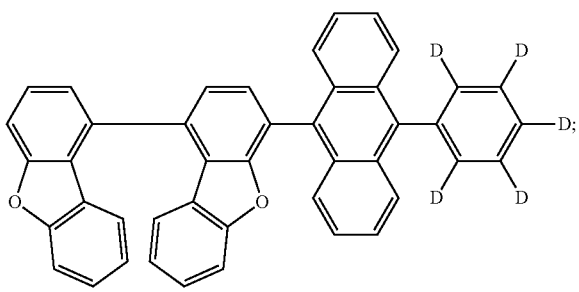
Compound 168
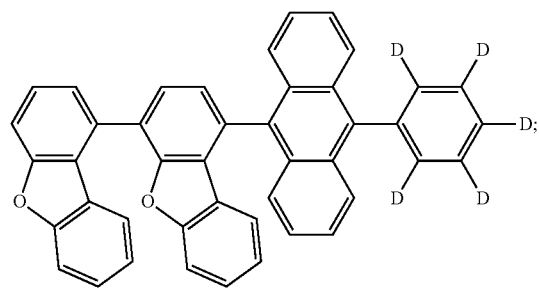
Compound 169
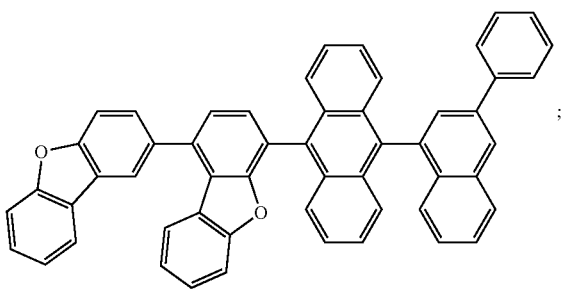
Compound 170
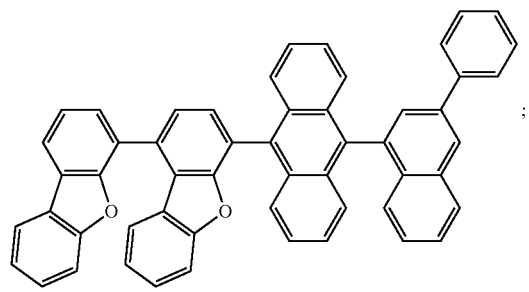
Compound 171
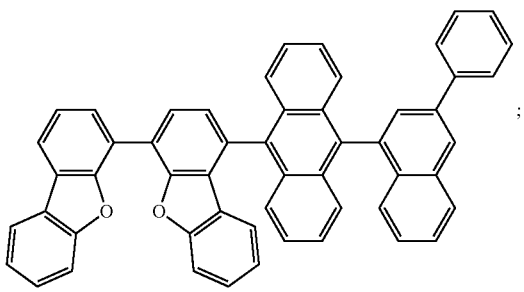
Compound 172
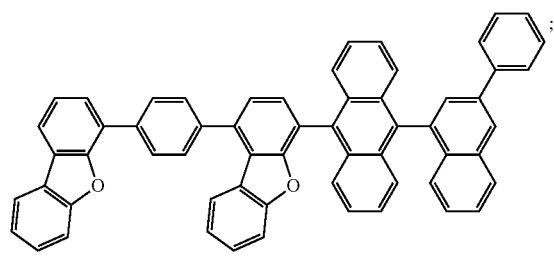
Compound 173
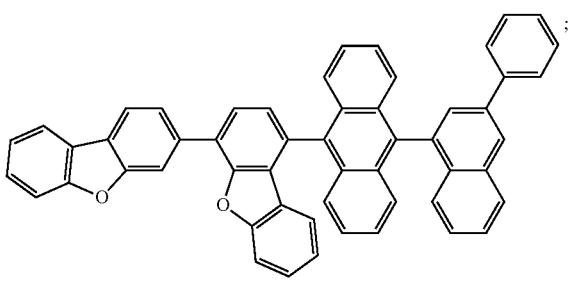

Compound 174
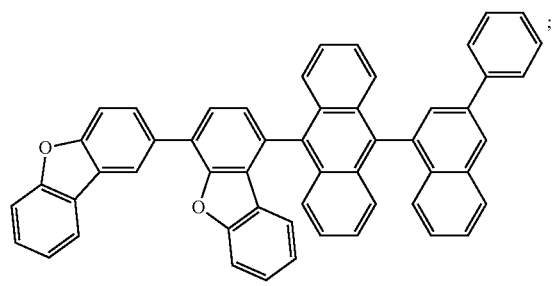
Compound 175
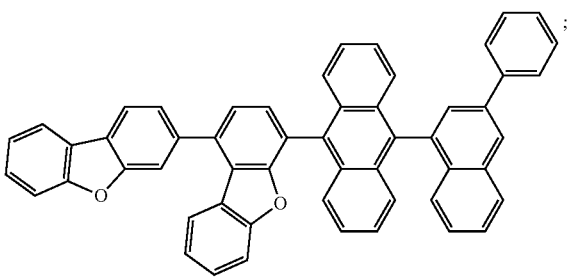
Compound 176
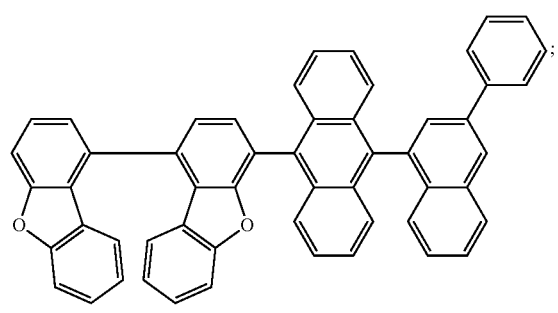
Compound 177
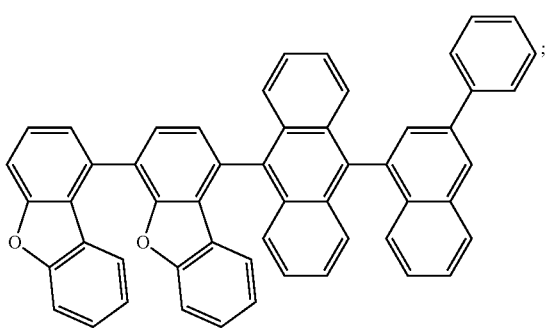
Compound 178
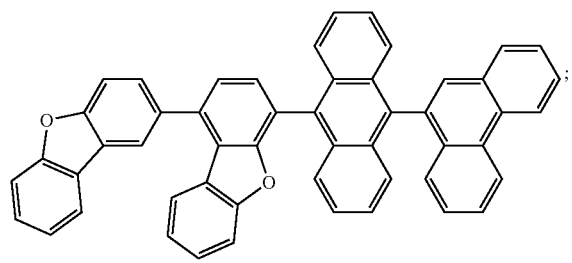
Compound 179
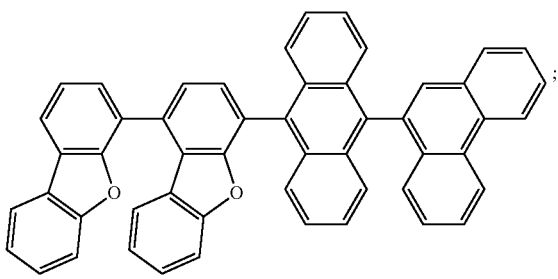
Compound 180
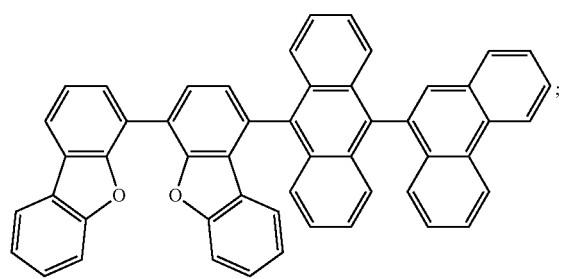
Compound 181
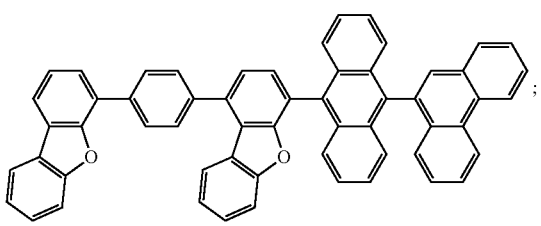
Compound 182
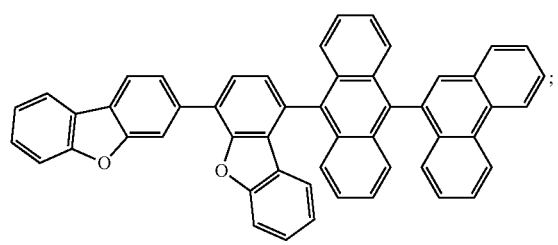
Compound 183
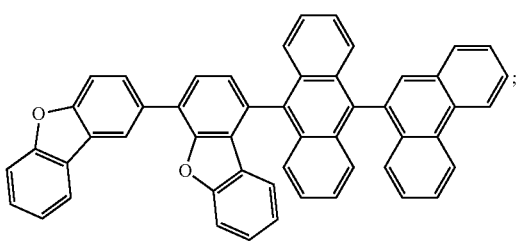

-continued
Compound 184
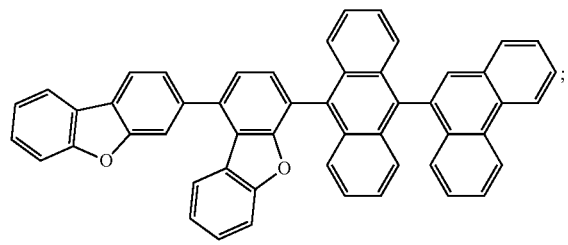
Compound 185
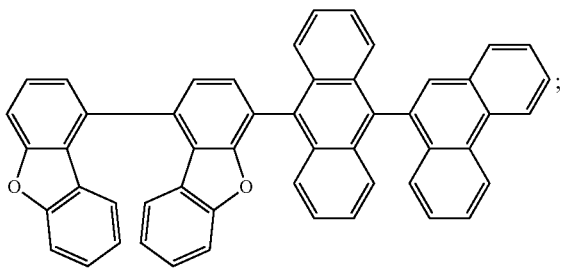
Compound 186
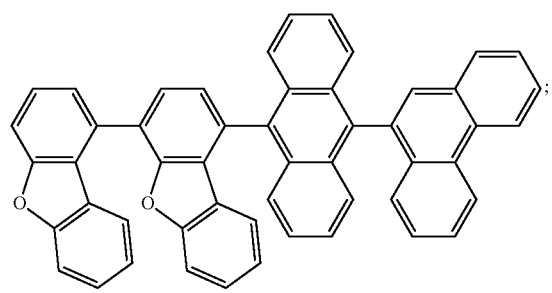
Compound 187
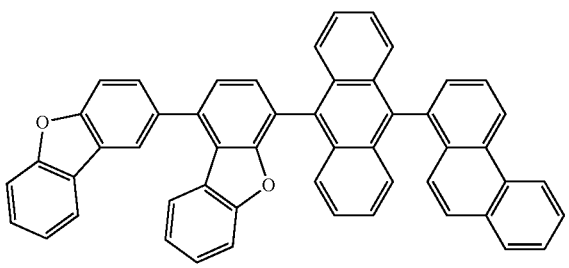
Compound 188
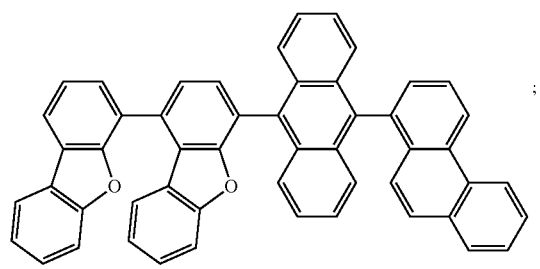
Compound 189
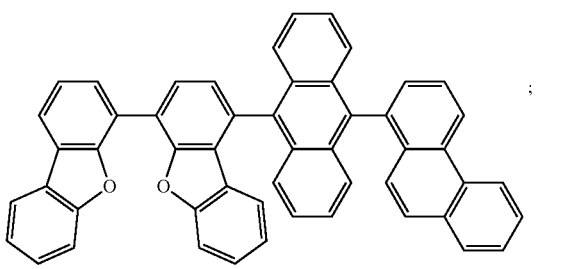
Compound 190
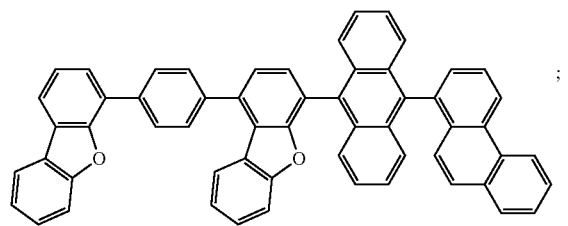
Compound 191
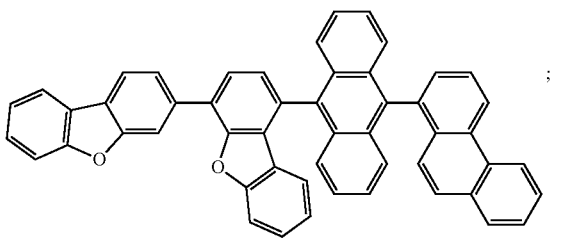
Compound 192
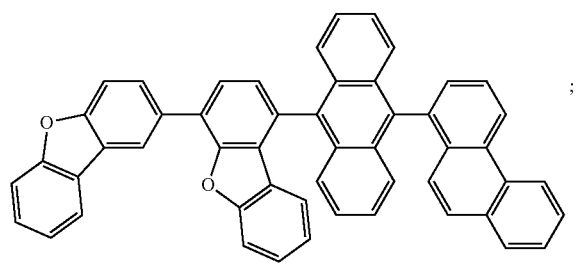
Compound 193
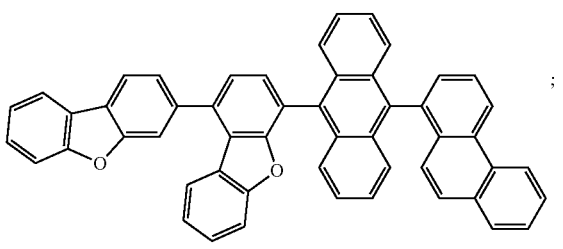

-continued
Compound 194
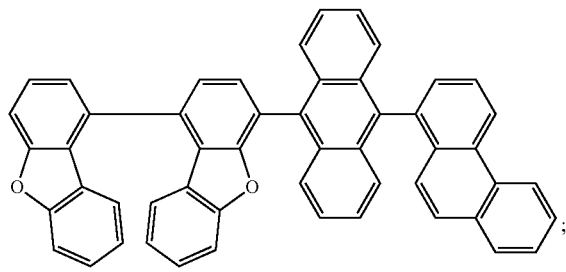
Compound 195
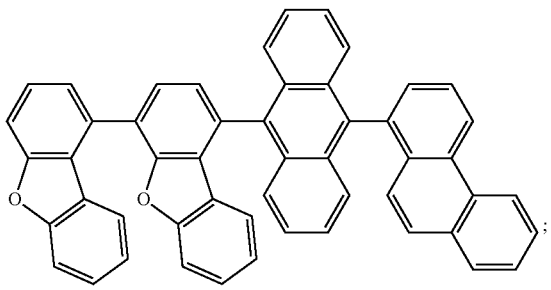
Compound 196
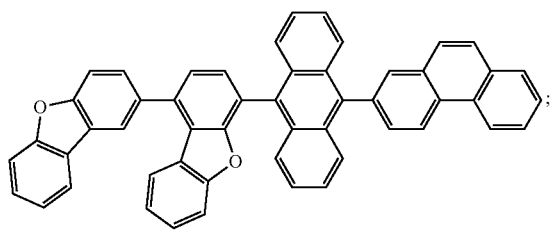
Compound 197
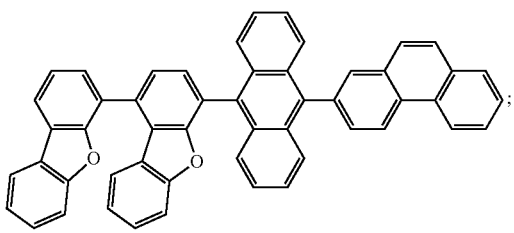
Compound 198
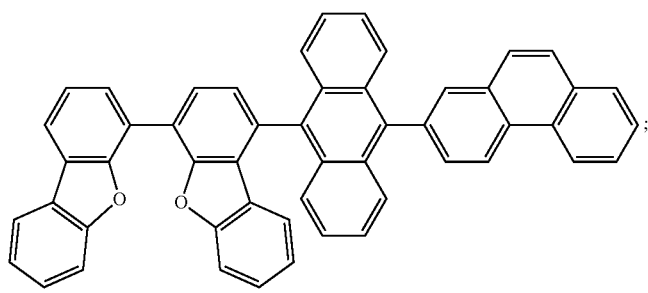
Compound 199
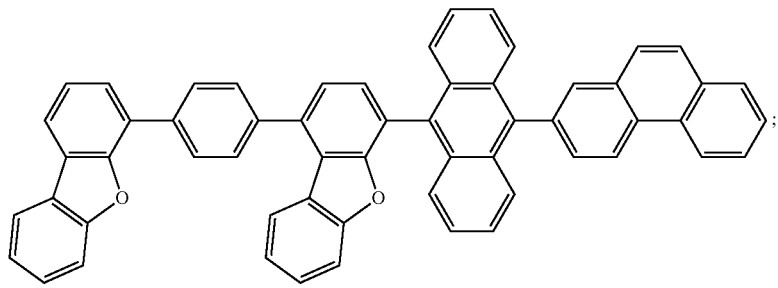
Compound 200
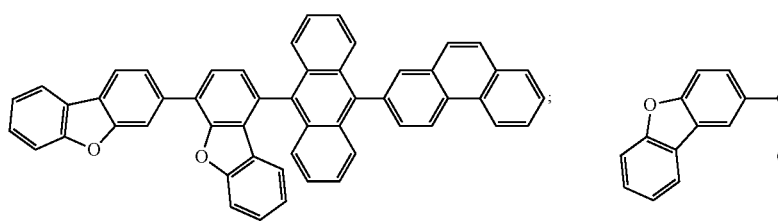
Compound 201
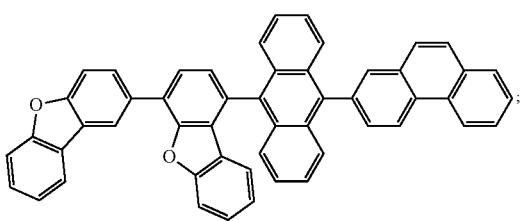
Compound 202
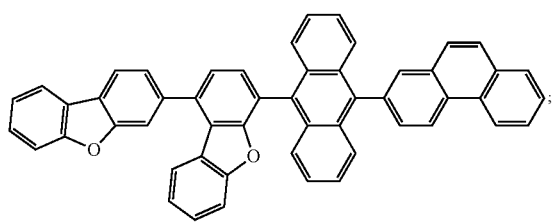
Compound 203
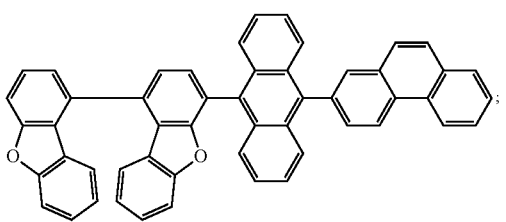

-continued
Compound 204
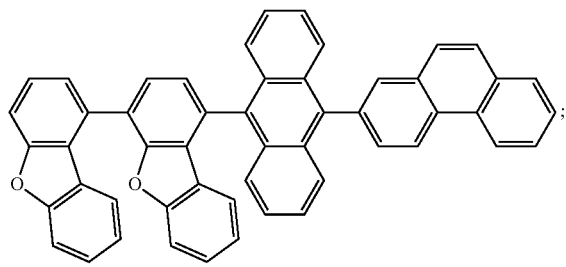
Compound 205
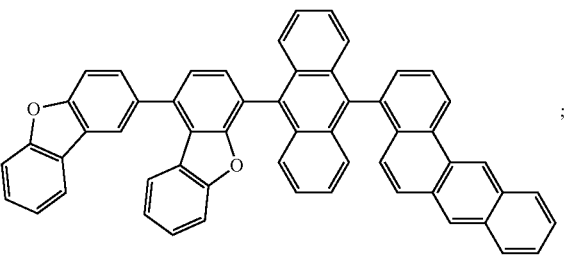
Compound 206
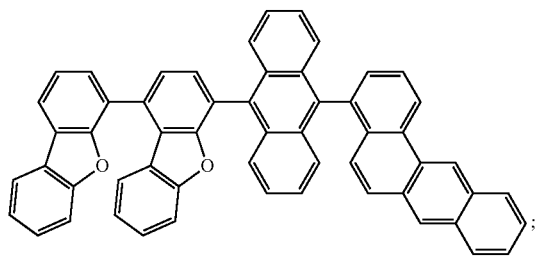
Compound 207
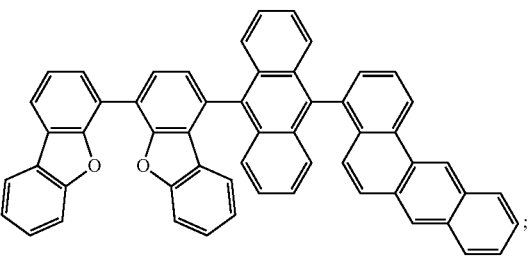
Compound 208
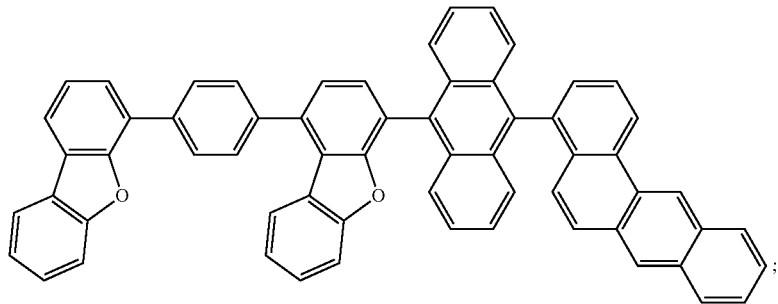
Compound 209
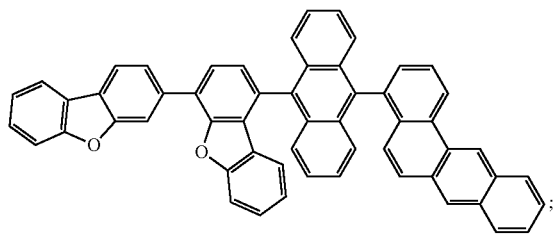
Compound 210
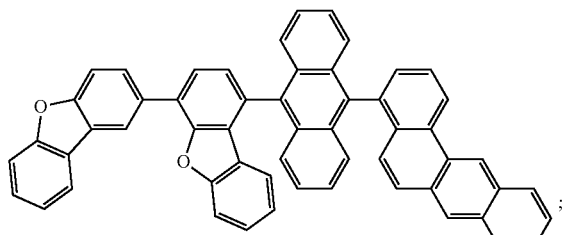
Compound 211
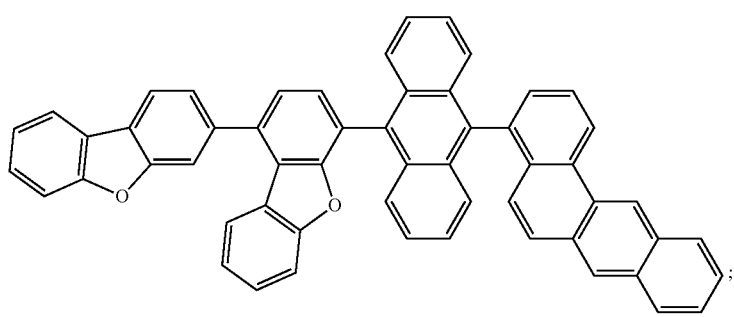

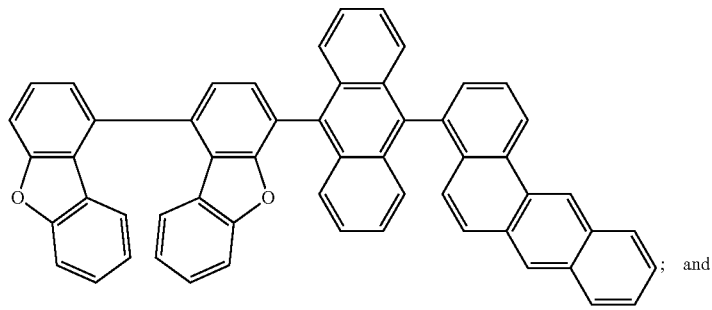

Compound 212 and

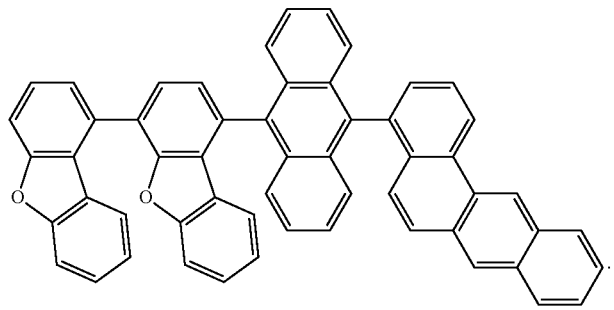

Compound 213

The present invention also provides an organic electronic device, comprising a first electrode, a second electrode, and an organic layer disposed between the first electrode and the second electrode. The organic layer comprises the novel compound as described above.

Preferably, the organic electronic device is an organic light emitting device (OLED). More preferably, the novel compound of the present invention may be used as host materials of EL, especially as blue host materials.

Specifically, the organic light emitting device may comprise:
a hole injection layer formed on the first electrode;
a hole transport layer formed on the hole injection layer;
an emission layer formed on the hole transport layer;
an electron transport layer formed on the emission layer;
an electron injection layer formed between the electron transport layer and the second electrode.

In one embodiment, the organic layer may be the emission layer, i.e., the emission layer comprises a dopant and a first host material which is the novel compound as stated above.

In another embodiment, the emission layer further comprises a second host material, the second host material is the novel compound as stated above or a conventional compound, and the second host material is different from the first host material.

For example, the emission layer may be a single-layered configuration or a multi-layered configuration. When the emission layer is the multi-layered configuration, e.g., the emission layer comprises a first emission layer and a second emission layer, the first host material of the first emission layer may be made of single novel compound and the second host material of the second emission layer may be made of another single novel compound or any single conventional compound. Or, the first host material of the first emission layer may be made of a novel compound in combination with another single novel compound or any single conventional compound, and so as the second host material.

Preferably, the hole injection layer may be a two-layered structure, i.e., the OLED comprises a first hole injection layer and a second hole injection layer disposed between the first electrode and the hole transport layer.

Preferably, the hole transport layer may be a two-layered structure, i.e., the OLED comprises a first hole transport layer and a second hole transport layer disposed between the two-layered hole injection layer and the emission layer.

Preferably, the emission layer comprises the novel compound such as Compounds 1 to 213. The OLEDs using the novel compound as the host material can have an improved efficiency compared to commercial OLEDs using known host materials of EL, such as 9,10-diphenylanthracene, 9,10-dinaphthylanthracene, 9-naphthyl-10-phenylanthracene, 9-(4-(naphthalen-1-yl)phenyl)-10-(naphthalen-2-yl) anthracene, 2-methyl-9,10-bis(naphthalen-2-yl)anthracene, or 2-phenyl-9,10-bis(naphthalen-2-yl)anthracene, as the host material.

Preferably, the OLED comprises a hole blocking layer formed between the electron transport layer and the emission layer, to block holes overflow from the emission layer to the electron transport layer. Said hole blocking layer may be made of 2,9-dimethyl-4,7-diphenyl-1,10-phenanthroline (BCP) or 2,3,5,6-tetramethyl-phenyl-1,4-(bis-phthalimide) (TMPP), but it is not limited thereto.

Preferably, the OLED comprises an electron blocking layer formed between the hole transport layer and the emission layer, to block electrons overflow from the emission layer to the hole transport layer. Said electron blocking layer may be made of 9,9'[1,1'-biphenyl]-4,4'-diylbis-9H-carbazole (CBP) or 4,4',4''-tri(N-carbazolyl)-triphenylamine (TCTA), but it is not limited thereto.

In the presence of such a hole blocking layer and/or an electron blocking layer in an OLED, the OLED has a higher luminous efficiency compared to a typical OLED.

Said first and second hole transport layers may be made of, for example, but not limited to:
$N^1,N^{1'}$-(biphenyl-4,4'-diyl)bis($N^1$-(naphthalen-1-yl)-$N^4,N^{4'}$-diphenylbenzene-1,4-diamine); or $N^4,N^{4'}$-di(naphthalen-1-yl)-$N^4,N^{4'}$-diphenylbiphenyl-4,4'-diamine (NPB).

Said first and second hole injection layers may be made of, for example, but not limited to, polyaniline or polyethylenedioxythiophene.

Preferably, the organic electronic device is a blue organic electronic device. For blue OLEDs, the dopant of the emission material is, for example, but not limited to: diaminofluorenes; diaminoanthracenes; diaminopyrenes; or organicmetallic compounds of iridium (II) having phenylpyridine ligands. With various host materials of the emission layer as stated above, the OLED can emit lights in blue.

Preferably, the electron transport layer is made of
3,3'-[5'-[3-(3-Pyridinyl)phenyl][1,1': 3',1''-terphenyl]-3,3''-diyl]bispyridine (TmPyPb),
3-(Biphenyl-4-yl)-5-(4-tert-butylphenyl)-4-phenyl-4H-1,2,4-triazole (TAZ),
1,3,5-tris(1-phenyl-1H-benzimidazol-2-yl)benzene (TPBi),
tris(2,4,6-trimethyl-3-(pyridin-3-yl)phenyl)borane (3TPYMB),
1,3-bis(3,5-dipyrid-3-yl-phenyl)benzene (BmPyPb), or
9,10-bis(3-(pyridin-3-yl)phenyl)anthracene (DPyPA), but it is not limited thereto.

Said electron injection layer may be made of an electron injection material, for example, but not limited to (8-oxidonaphthalen-1-yl)lithium(II).

Said first electrode is, for example, but not limited to, an indium-doped tin oxide electrode.

Said second electrode has a work function lower than that of the first electrode. The second electrode is, for example, but not limited to, an aluminum electrode, an indium electrode, or a magnesium electrode.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
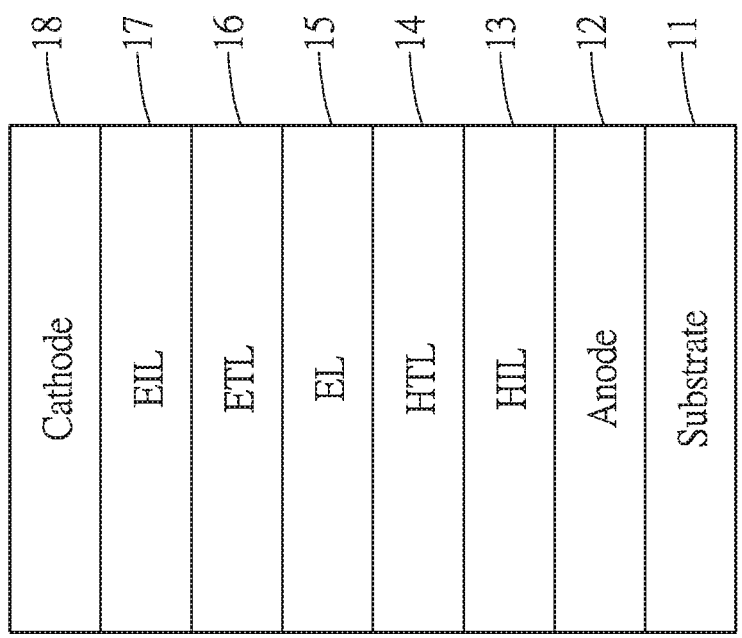
FIG. 1 illustrates a schematic cross-sectional view of an OLED.

Hereinafter, one skilled in the arts can easily realize the advantages and effects of a novel compound and an organic light emitting device using the same in accordance with the present invention from the following examples. It should be understood that the descriptions proposed herein are just preferable examples only for the purpose of illustrations, not intended to limit the scope of the invention. Various modifications and variations could be made in order to practice or apply the present invention without departing from the spirit and scope of the invention.

Synthesis of Intermediate An

Intermediate An used for preparing a novel compound was synthesized by the following steps.

Synthesis of Intermediate An-2

In step 1, the general synthesis pathway of Intermediate An-2 was summarized in Scheme A1.

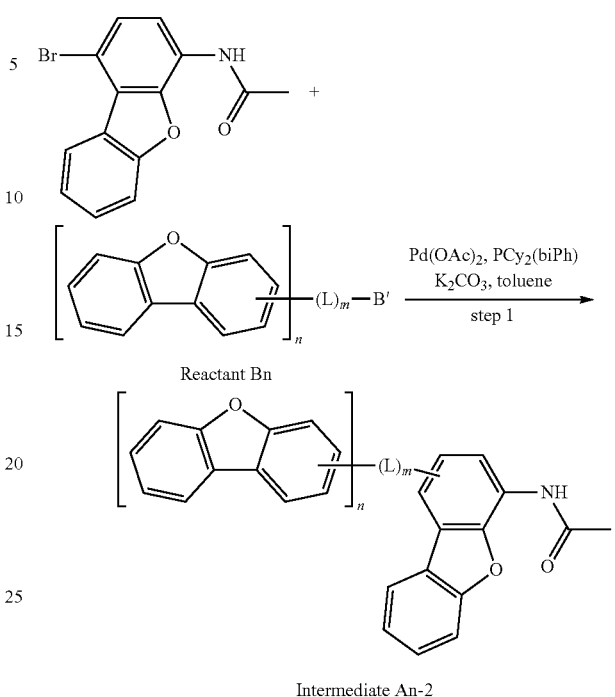

Wherein B' is B(OH)₂ group or

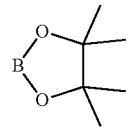

group; L is a substituted or unsubstituted arylene group having 6 to 60 ring carbon atoms; m is an integer 0 or 1; n is an integer 1 or 2.

Synthesis of Intermediate A1-2

Taking Intermediate A1-2 as an example of Intermediate An-2, the synthesis pathway of Intermediate A1-2 was summarized in Scheme A1-1.

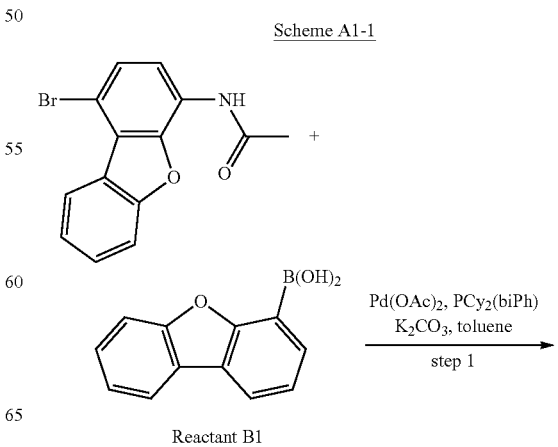

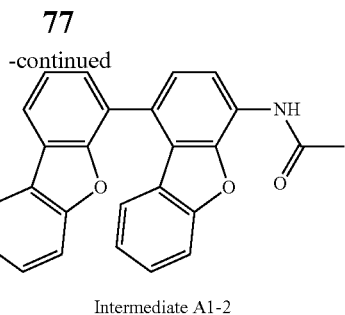

Intermediate A1-2

A mixture of 1-bromo-4-acetamidodibenzofuran (30.0 g, 1.0 eq), 4-dibenzofuranboronic acid (1.25 eq), Palladium(II) acetate [Pd(OAc)$_2$] (0.01 eq), 2-(dicyclohexylphosphino) biphenyl [PCy$_2$(2-biPh)] (0.04 eq), and potassium carbonate (K$_2$CO$_3$) (2.0 eq) was in a mixed solution of toluene (165 mL), ethanol (16.5 mL) and H$_2$O (60.0 mL). The reaction mixture was heated to about 80° C. under reflux and stirred for 16 hours under nitrogen atmosphere. After the completion of the reaction, the reaction mixture was cooled to room temperature, and the crude product was extracted and collected by the organic layer. The organic layer was dried over MgSO$_4$, separated by filtration and concentrated to dryness. A resulting residue was purified by silica gel column chromatography to obtain 34.5 g of white solid product in yield 90.25%.

The white solid product was identified as Intermediate A1-2 by a field desorption mass spectroscopy (FD-MS) analysis. FD-MS analysis: C$_{26}$H$_{17}$NO$_3$: theoretical value of 391.42 and observed value of 391.42.

Syntheses of Intermediates A2-2 to A6-2

Intermediates A2-2 to A6-2, which also can be used for preparing a novel compound, were respectively synthesized in a similar manner as Intermediate A1-2 through step 1, except that the starting material Reactant B1 was replaced by Reactants B2 to B6, respectively. All intermediates were analyzed as described above, and the results were listed in Table 1.

TABLE 1

Reactant Bn used for preparing Intermediates A1-2 to A6-2, and the chemical structures, yields, formulae, and mass analyzed by FD-MS of Intermediates A1-2 to A6-2.

| Chemical Structure of Reactant Bn | Chemical Structure of Intermediate An-2 | Yield (%) | Formula/ Mass (M$^+$) |
|---|---|---|---|
| B1 | A1-2 | 90.25 | C$_{26}$H$_{17}$NO$_3$ 391.42 |
| B2 | A2-2 | 90.0 | C$_{26}$H$_{17}$NO$_3$ 391.42 |
| B3 | A3-2 | 91.5 | C$_{26}$H$_{17}$NO$_3$ 391.42 |

TABLE 1-continued

Reactant Bn used for preparing Intermediates A1-2 to A6-2, and the chemical structures, yields, formulae, and mass analyzed by FD-MS of Intermediates A1-2 to A6-2.

| Chemical Structure of Reactant Bn | Chemical Structure of Intermediate An-2 | Yield (%) | Formula/ Mass (M+) |
|---|---|---|---|
| B4 | A4-2 | 93.0 | $C_{26}H_{17}NO_3$, 391.42 |
| B5 | A5-2 | 87.6 | $C_{32}H_{21}NO_3$, 467.51 |
| B6 | A6-2 | 81.7 | $C_{38}H_{23}NO_4$, 557.59 |

In the above Table 1, Reactant B6 is also named Intermediate A1 below, which can be synthesized through steps 1 to 4 from a starting material, Reactant B1.

Modifications of Intermediates A1-2 to A6-2

In addition to Intermediates A1-2 to A6-2, one person skilled in the art can adopt other applicable starting materials and successfully synthesize other desired intermediates through a reaction mechanism similar to Scheme A1-1. When reacting a starting material like Reactant B5, which contains a phenylene group between the dibenzofuranyl group and the —B(OH)$_2$ group, with bromo acetamidod-ibenzofuran, an intermediate which contains two dibenzofuranyl moieties and a phenylene group inserted therebetween could be synthesized. When reacting a starting material like Reactant B6, which contains two bonded dibenzofuranyl groups, with bromo acetamidodibenzofuran, an intermediate which contains three dibenzofuranyl moieties linked together could be synthesized.

Synthesis of Intermediate An-3

In step 2, the general synthesis pathway of Intermediate An-3 was summarized in Scheme A2.

Scheme A2

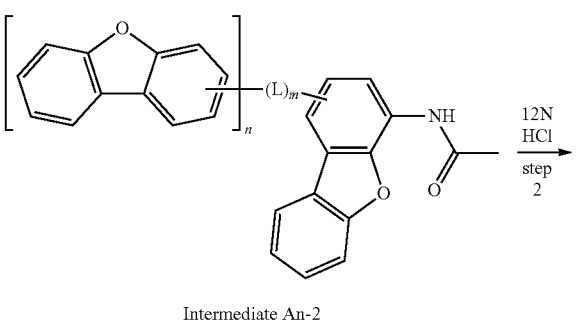

Intermediate An-2

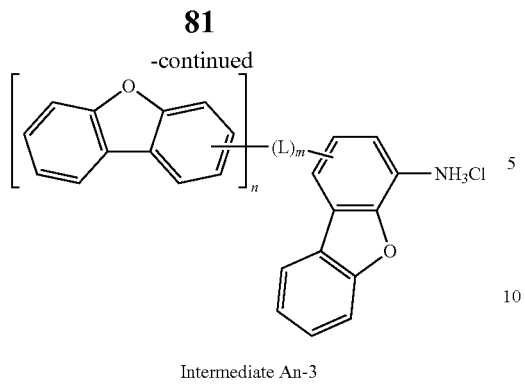

Intermediate An-3

In Scheme A2, L, m, and n are as stated in Scheme A1.
Synthesis of Intermediate A1-3

Taking Intermediate A1-3 as an example of Intermediate An-3, the synthesis pathway of Intermediate A1-3 was summarized in Scheme A2-1.

Scheme A2-1

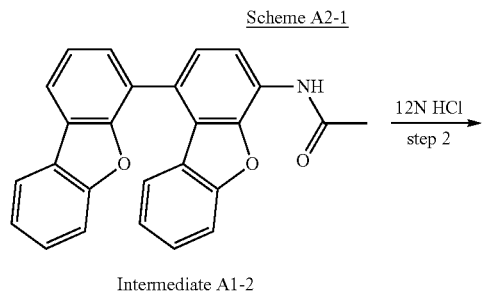

Intermediate A1-2

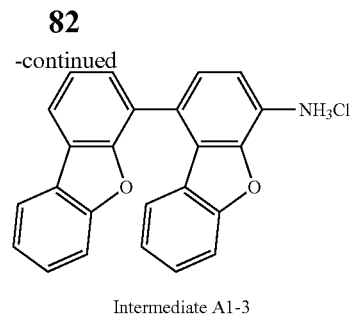

Intermediate A1-3

Intermediate A1-2 (55 g, 1.0 eq) dissolved in 12N HCl (100 mL) was stirred magnetically in 275 mL ethanol at reflux temperature for 8 hours, and then the reaction mixture was cooled to room temperature. The crude solid product was separated by filtration, washed with $H_2O$ and dried. The yield of step 2 was 98.5%.

The product was identified as Intermediate A1-3 by a FD-MS analysis. FD-MS analysis: $C_{24}H_{16}ClNO_2$: theoretical value of 385.84 and observed value of 385.84.

Syntheses of Intermediates A2-3 to A6-3

Intermediates A2-3 to A6-3, which also can be used for preparing a novel compound, were respectively synthesized in a similar manner as Intermediate A1-3 through step 2, except that the starting material Intermediate A1-2 was replaced by Intermediates A2-2 to A6-2, respectively. All intermediates were analyzed as described above, and the results were listed in Table 2.

TABLE 2

The chemical structures, yields, formulae, and mass analyzed by FD-MS of Intermediates A1-3 to A6-3.

| Intermediate An-3 No. | Chemical Structure of Intermediate An-3 | Yield (%) | Formula/ Mass (M+) |
|---|---|---|---|
| A1-3 | (structure) | 98.5 | $C_{24}H_{16}ClNO_2$ 385.84 |
| A2-3 | (structure) | 97.1 | $C_{24}H_{16}ClNO_2$ 385.84 |
| A3-3 | (structure) | 98.0 | $C_{24}H_{16}ClNO_2$ 385.84 |

TABLE 2-continued

The chemical structures, yields, formulae, and mass analyzed by FD-MS of Intermediates A1-3 to A6-3.

| Intermediate An-3 No. | Chemical Structure of Intermediate An-3 | Yield (%) | Formula/ Mass (M⁺) |
|---|---|---|---|
| A4-3 | | 96.5 | $C_{24}H_{16}ClNO_2$ 385.84 |
| A5-3 | | 97.0 | $C_{30}H_{20}ClNO_2$ 461.94 |
| A6-3 | | 95.5 | $C_{36}H_{22}ClNO_3$ 552.02 |

Modifications of Intermediates A1-3 to A6-3

In addition to Intermediates A1-3 to A6-3, one person skilled in the art can adopt other applicable starting materials and successfully synthesize other desired intermediates through a reaction mechanism similar to Scheme A2-1.

Synthesis of Intermediate An-4

In step 3, the general synthesis pathway of Intermediate An-4 was summarized in Scheme A3.

Scheme A3

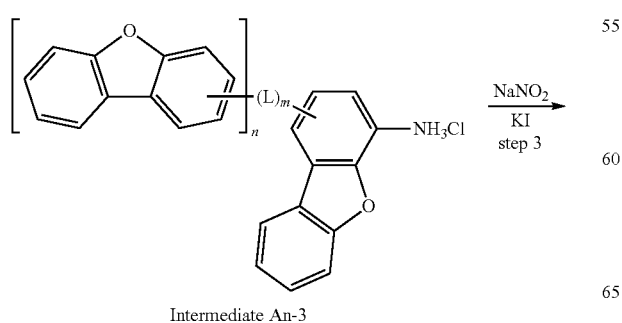

Intermediate An-3

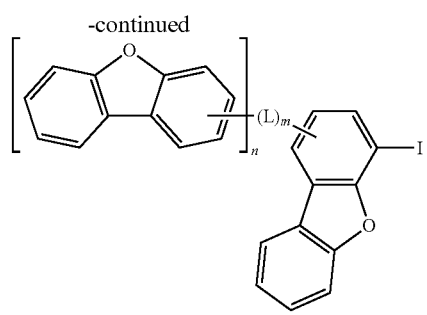

Intermediate An-4

In Scheme A3, L, m, and n are as stated in Scheme A1.

Synthesis of Intermediate A1-4

Taking Intermediate A1-4 as an example of Intermediate An-4, the synthesis pathway of Intermediate A1-4 was summarized in Scheme A3-1.

Scheme A3-1

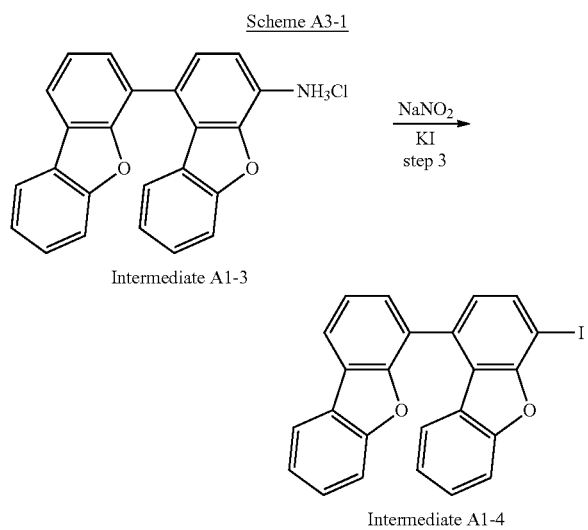

Intermediate A1-3 → (NaNO₂, KI, step 3) → Intermediate A1-4

Intermediate A1-3 (10.0 g, 1.0 eq) was added in a mixed solution of 12N HCl (40 mL) and CH₃CN (130 mL), and cooled to lower than 5° C. An aqueous solution of sodium nitrite (NaNO₂) (2.0 eq) and potassium iodide (KI) (2.5 eq) in 15.0 mL H₂O was slowly added to the foresaid cooled solution, and the reaction mass was stirred for 10 min, and then its temperature was raised to 20° C. and the reaction mass was stirred overnight. After that, the pH value of the solution was adjusted by saturated solution of sodium hydrogen carbonate (NaHCO₃) and sodium thiosulfate (Na₂S₂O₃) (2.5 eq) until the pH was between 9 and 10. The precipitate was separated by filtration or extracted with ethyl acetate, and then purified by flash chromatography with eluent (hexane to CH₂Cl₂ is 5 to 1) to get a grey solid product. The yield of step 3 was 85.7%.

The grey solid product was identified as Intermediate A1-4 by a FD-MS analysis. FD-MS analysis: $C_{24}H_{13}IO_2$: theoretical value of 460.26 and observed value of 460.26.

Syntheses of Intermediates A2-4 to A6-4

Intermediates A2-4 to A6-4, which also can be used for preparing a novel compound, were respectively synthesized in a similar manner as Intermediate A1-4 through step 3, except that the starting material Intermediate A1-3 was replaced by Intermediates A2-3 to A6-3, respectively. All intermediates were analyzed as described above, and the results were listed in Table 3.

TABLE 3

The chemical structures, yields, formulae, and mass analyzed by FD-MS of Intermediates A1-4 to A6-4.

| Intermediate An-4 No. | Chemical Structure of Intermediate An-4 | Yield (%) | Formula/ Mass (M⁺) |
|---|---|---|---|
| A1-4 | [structure] | 85.7 | $C_{24}H_{13}IO_2$ 460.26 |
| A2-4 | [structure] | 81.2 | $C_{24}H_{13}IO_2$ 460.26 |
| A3-4 | [structure] | 83.4 | $C_{24}H_{13}IO_2$ 460.26 |
| A4-4 | [structure] | 84.6 | $C_{24}H_{13}IO_2$ 460.26 |
| A5-4 | [structure] | 82.6 | $C_{30}H_{17}IO_2$ 536.36 |
| A6-4 | [structure] | 67.4 | $C_{36}H_{19}IO_3$ 626.44 |

Modifications of Intermediates A1-4 to A6-4

In addition to Intermediates A1-4 to A6-4, one person skilled in the art can adopt other applicable starting materials and successfully synthesize other desired intermediates through a reaction mechanism similar to Scheme A3-1.

Synthesis of Intermediate An

In step 4, the general synthesis pathway of Intermediate An was summarized in Scheme A4.

Scheme A4

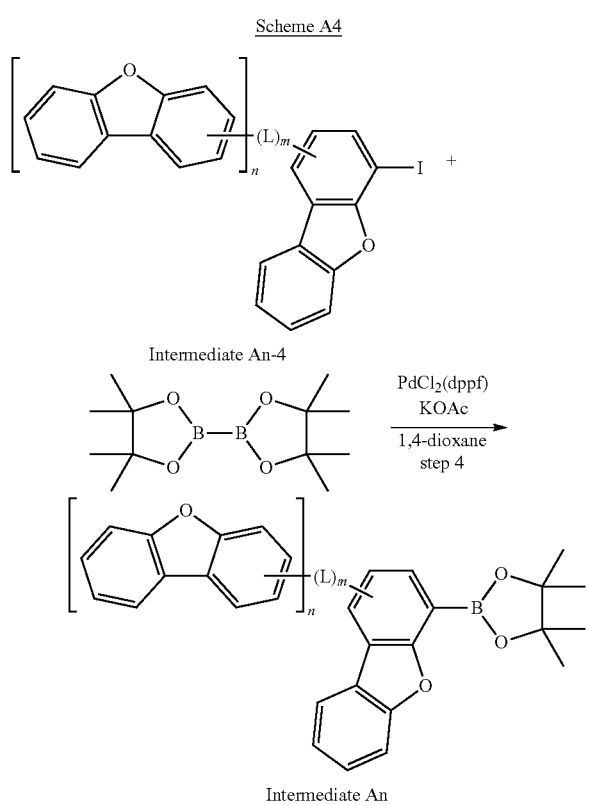

Intermediate An-4

Intermediate An

In Scheme A4, L, m, and n are as stated in Scheme A1.
Synthesis of Intermediate A1
Taking Intermediate A1 as an example of Intermediate An, the synthesis pathway of Intermediate A1 was summarized in Scheme A4-1.

Scheme A4-1

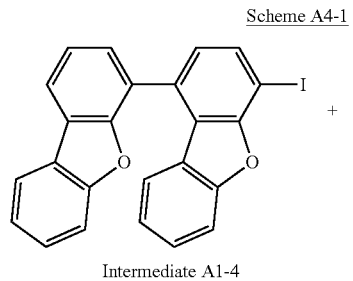

Intermediate A1-4

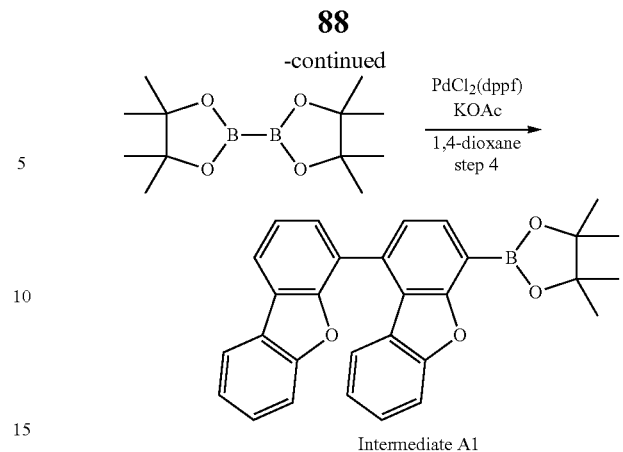

Intermediate A1

A mixture of Intermediate A1-4 (30.0 g, 1.0 eq), bis(pinacolato)diboron (1.20 eq), 1,1'-bis(diphenylphosphino)-ferrocene dichloropalladium (II) [PdCl$_2$(dppf)] (0.02 eq), and potassium acetate (KOAc) (2.0 eq) in 1,4-dioxane (165 mL) was stirred at 95° C. for 16 hours under nitrogen atmosphere. After cooling to room temperature, the crude product was extracted with H$_2$O and collected by the organic layer. The organic layer was dried over MgSO$_4$, separated by filtration and then concentrated to dryness. A resulting residue was purified by silica gel column chromatography to obtain 34.5 g of white solid product. The yield of step 4 was 91.35%.

The white solid product was identified as Intermediate A1 by a FD-MS analysis. FD-MS analysis: C$_{30}$H$_{25}$BO$_4$: theoretical value of 460.33 and observed value of 460.33.

Syntheses of Intermediates A2 to A6

Intermediates A2 to A6, which also can be used for preparing a novel compound, were respectively synthesized in a similar manner as Intermediate A1 through step 4, except that the starting material Intermediate A1-4 was replaced by Intermediates A2-4 to A6-4, respectively. All intermediates were analyzed as described above, and the results were listed in Table 4.

TABLE 4

The chemical structures, yields, formulae, and mass analyzed by FD-MS of Intermediates A1 to A6.

| Intermediate An No. | Chemical Structure of Intermediate An | Yield (%) | Formula/ Mass (M$^+$) |
|---|---|---|---|
| A1 | 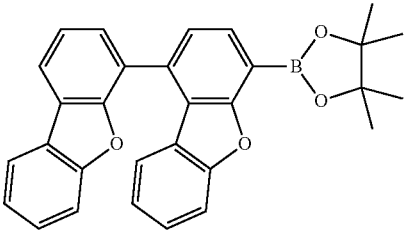 [SMILES: CC1(C)OB(c2ccc(-c3cccc4c3oc3ccccc34)c3c2oc2ccccc23)OC1(C)C] | 91.35 | C$_{30}$H$_{25}$BO$_4$ 460.33 |

TABLE 4-continued
The chemical structures, yields, formulae, and mass analyzed by FD-MS of Intermediates A1 to A6.
| Intermediate An No. | Chemical Structure of Intermediate An | Yield (%) | Formula/ Mass (M+) |
|---|---|---|---|
| A2 | 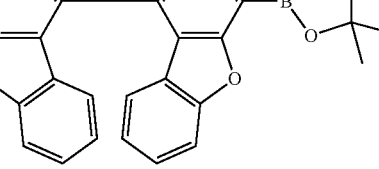 | 93.1 | C₃₀H₂₅BO₄ 460.33 |
| A3 | 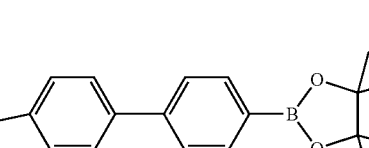 | 92.0 | C₃₀H₂₅BO₄ 460.33 |
| A4 | 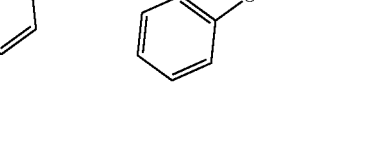 | 91.2 | C₃₀H₂₅BO₄ 460.33 |
| A5 | 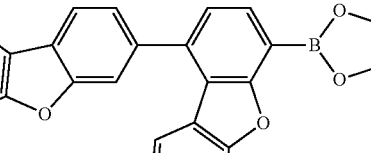 | 90.5 | C₃₆H₂₉BO₄ 536.42 |
| A6 | 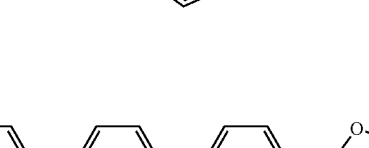 | 85.5 | C₄₂H₃₁BO₅ 626.5 |

Modifications of Intermediates A1 to A6

In addition to Intermediates A1 to A6, one person skilled in the art can adopt other starting materials and successfully synthesize other desired intermediates through a reaction mechanism similar to Scheme A4-1.

Intermediate An used for preparing a novel compound can also be synthesized by the following steps.

Synthesis of Intermediate A'n-3

Intermediate A'n-3 used for preparing a novel compound was synthesized by the following steps. The general synthesis pathway of Intermediate A'n-3 was summarized in Scheme A5.

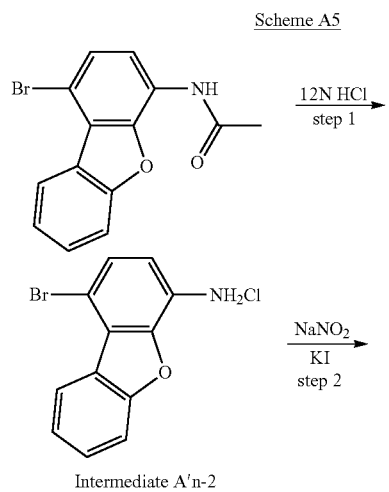

Step 1: Synthesis of Intermediate A'n-2

1-Bromo-4-acetamidodibenzofuran (55 g, 1.0 eq) dissolved in 12N HCl (100 mL) was stirred magnetically in 275 mL ethanol at reflux temperature for 8 hours, and then the reaction mixture was cooled to room temperature. The crude solid product was separated by filtration, washed with $H_2O$ and dried. The yield of step 1 was 97%.

The product was identified as Intermediate A'n-2 by a FD-MS analysis. FD-MS analysis: $C_{12}H_9BrClNO$: theoretical value of 298.56 and observed value of 298.56.

Step 2: Synthesis of Intermediate A'n-3

Intermediate A'n-2 (60.0 g, 1.0 eq) was added in a mixed solution of 12N HCl (50 mL) and $CH_3CN$ (240 mL), and cooled to lower than 5° C. An aqueous solution of $NaNO_2$ (2.0 eq) and KI (2.5 eq) in 400 mL $H_2O$ was slowly added to the foresaid cooled solution, and the reaction mass was stirred for 10 min, and then its temperature was raised to 20° C. and the reaction mass was stirred overnight. After that, the pH value of the solution was adjusted by saturated solution of $NaHCO_3$ and $Na_2S_2O_3$ (2.5 eq) until the pH value of the solution was between 9 and 10. The precipitate was separated by filtration or extracted with ethyl acetate, and then purified by flash chromatography with eluent (hexane to $CH_2Cl_2$ is 5 to 1) to get a grey solid product. The yield of step 2 was 83.2%.

The grey solid product was identified as Intermediate A'n-3 by a FD-MS analysis. FD-MS analysis: $C_{12}H_6BrIO$: theoretical value of 372.98 and observed value of 372.98.

Synthesis of Intermediate A'n-4

Intermediate A'n-4 used for preparing a novel compound was synthesized by the following step. The general synthesis pathway of Intermediate A'n-4 was summarized in Scheme A6.

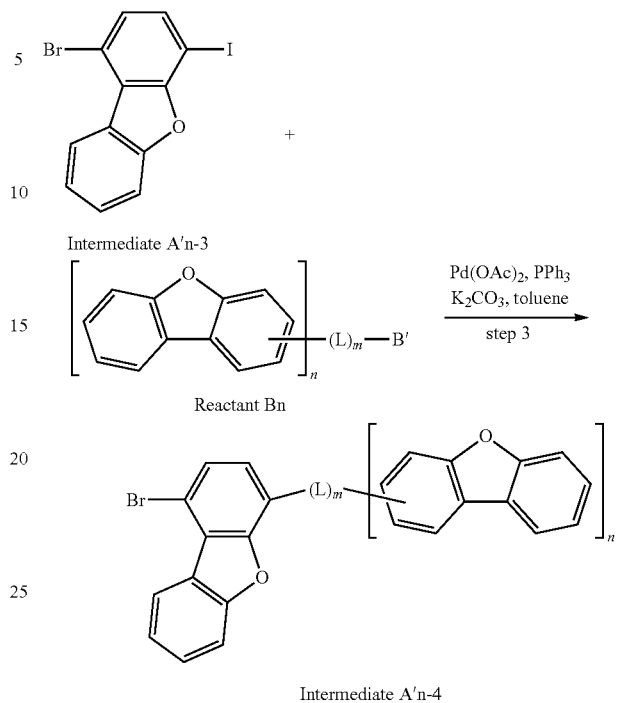

In Scheme A6, B', L, m, and n are as stated in Scheme A1.

Step 3: Synthesis of Intermediate A'7-4

Taking Intermediate A'7-4 as an example of Intermediate A'n-4, the synthesis pathway of Intermediate A'7-4 was summarized in Scheme A6-1.

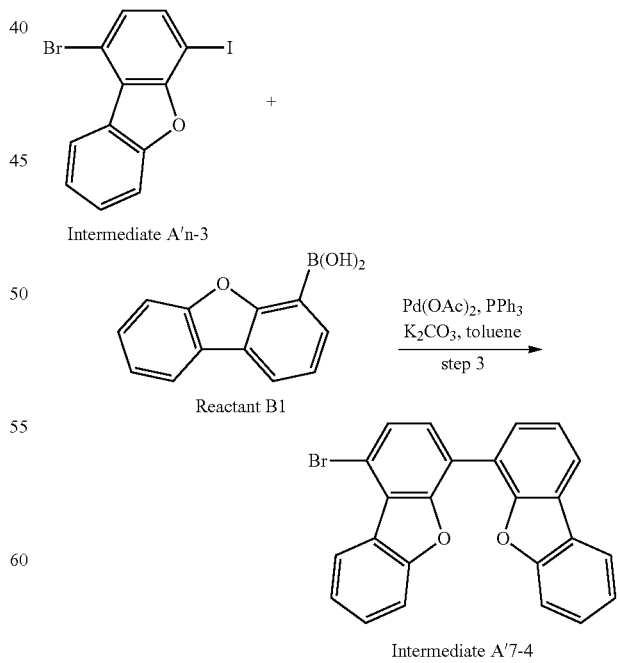

A mixture of Intermediate A'n-3 (1-bromo-4-iododibenzofuran (30.0 g, 1.0 eq), 4-dibenzofuranboronic acid (1.25 eq), Pd(OAc)$_2$ (0.01 eq), triphenylphosphine (PPh$_3$) (0.04 eq), and K$_2$CO$_3$ (2.0 eq) was in a mixed solution of toluene (260 mL), ethanol (26 mL) and H$_2$O (55 mL). The reaction mixture was heated to about 80° C. under reflux and stirred for 16 hours under nitrogen atmosphere. After completion of the reaction, the reaction mixture was cooled to room temperature, and the crude product was extracted and collected by the organic layer. The organic layer was dried over MgSO$_4$, separated by filtration and concentrated to dryness. A resulting residue was purified by silica gel column chromatography to obtain 29.3 g of white solid product. The yield of step 3 was 88.15%.

The white solid product was identified as Intermediate A'7-4 by a FD-MS analysis. FD-MS analysis: C$_{24}$H$_{13}$BrO$_2$: theoretical value of 413.26 and observed value of 413.26.

Synthesis of Intermediate A'8-4

Intermediate A'8-4 used for preparing a novel compound was synthesized in a similar manner as Intermediate A'7-4 through step 3, except that the starting material Reactant B1 was replaced by Reactant B2. All intermediates were analyzed as described above, and the results were listed in Table 5.

Modifications of Intermediates A'7-4 and A'8-4

In addition to Intermediates A'7-4 and A'8-4, one person skilled in the art can adopt other starting materials and successfully synthesize other desired intermediates through a reaction mechanism similar to Scheme A6-1.

Synthesis of Intermediate An

Intermediate An used for preparing a novel compound was synthesized by the following step. The general synthesis pathway of Intermediate An was summarized in Scheme A7.

Scheme A7

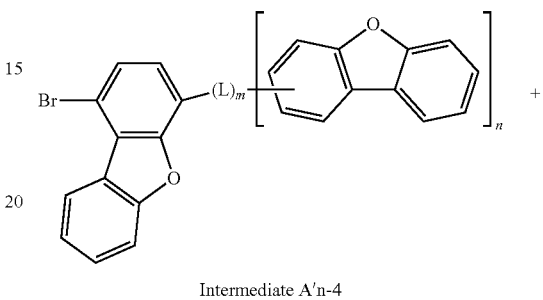

Intermediate A'n-4

TABLE 5

Reactant Bn used for preparing Intermediates A'7-4 and A'8-4, and the chemical structures, yields, formulae, and mass analyzed by FD-MS of Intermediates A'7-4 and A'8-4.

| Chemical Structure of Reactant Bn | Chemical Structure of Intermediate A'n-4 | Yield (%) | Formula/ Mass (M⁺) |
|---|---|---|---|
| 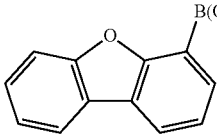<br>B1 | 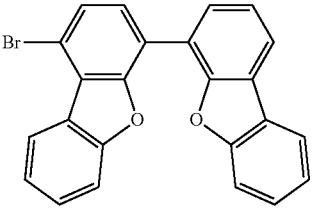 [SMILES: Brc1ccc(-c2cccc3c2oc2ccccc23)c2oc3ccccc3c12]<br>A'7-4 | 88.15 | C$_{24}$H$_{13}$BrO$_2$<br>413.26 |
| 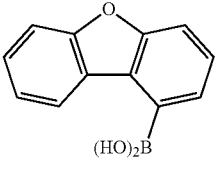<br>B2 | 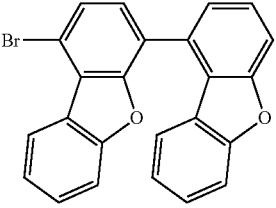 [SMILES: Brc1ccc(-c2cccc3oc4ccccc4c23)c2oc3ccccc3c12]<br>A'8-4 | 86.3 | C$_{24}$H$_{13}$BrO$_2$<br>413.26 |

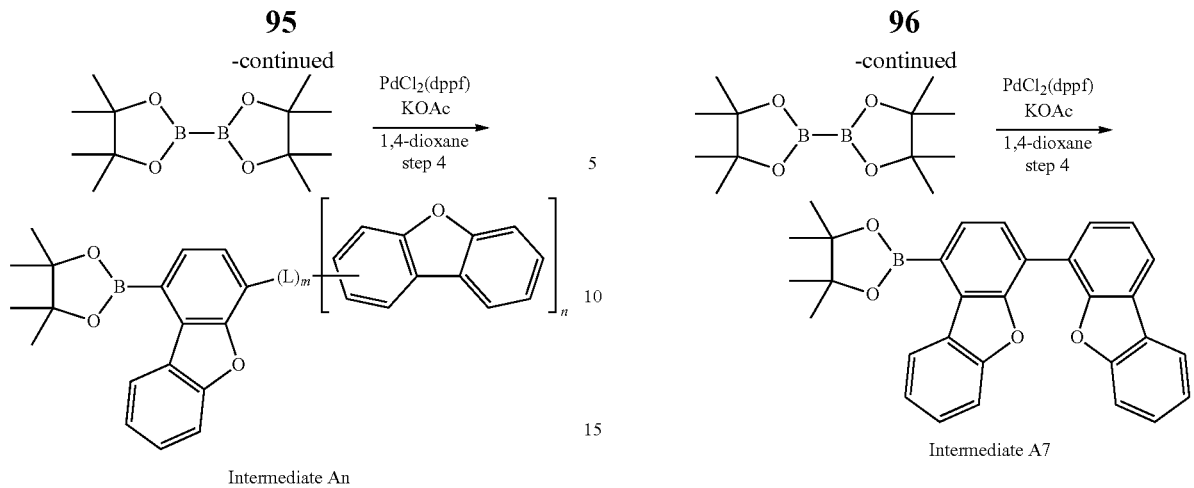

Intermediate An

In Scheme A7, L, m, and n are as stated in Scheme A1.
Step 4: Synthesis of Intermediate A7

Taking Intermediate A7 as an example of Intermediate An, the synthesis pathway of Intermediate A7 was summarized in Scheme A7-1.

Scheme A7-1

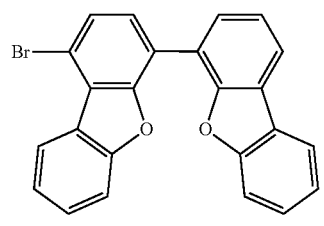

Intermediate A'7-4

Intermediate A7

A mixture of Intermediate A'7-4 (27.0 g 1.0 eq), bis(pinacolato)diboron (1.20 eq), PdCl$_2$(dppf) (0.02 eq), and KOAc (2.0 eq) in 1,4-dioxane (165 mL) was stirred at 95° C. for 16 hours under nitrogen atmosphere. After cooling to room temperature, the crude product was extracted with H$_2$O and collected by the organic layer. The organic layer was dried over MgSO$_4$, separated by filtration and then concentrated to dryness. A resulting residue was purified by silica gel column chromatography to obtain 28.1 g of white solid product. The yield of step 4 was 93.4%.

The white solid product was identified as Intermediate A7 by a FD-MS analysis. FD-MS analysis: C$_{30}$H$_{25}$BO$_4$: theoretical value of 460.33 and observed value of 460.33.

Synthesis of Intermediate A8

Intermediate A8 used for preparing a novel compound was synthesized in a similar manner as Intermediate A7 through step 4, except that the starting material Intermediate A'7-4 was replaced by Intermediate A'8-4. All intermediates were analyzed as described above, and the results were listed in Table 6.

TABLE 6 the chemical structures, yields, formulae, and mass analyzed by FD-MS of Intermediates A7 and A8.

| Intermediate An No. | Chemical Structure of Intermediate An | Yield (%) | Formula/ Mass (M⁺) |
|---|---|---|---|
| A7 | | 93.4 | C$_{30}$H$_{25}$BO$_4$ 460.33 |
| A8 | | 92.9 | C$_{30}$H$_{25}$BO$_4$ 460.33 |

Modifications of Intermediates A9 and A12

In addition to Intermediates A7 and A8, one person skilled in the art can adopt other starting materials and successfully synthesize other desired intermediates through a reaction mechanism similar to Scheme A7-1. Applicable modifications of Intermediates A7 and A8 may be, for example, but not limited to, Intermediates A9 to A12 as follows.

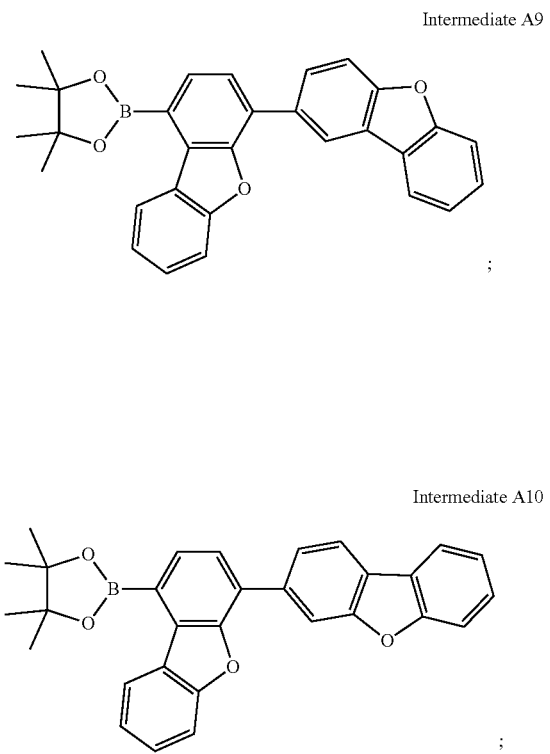

Intermediate A9

Intermediate A10

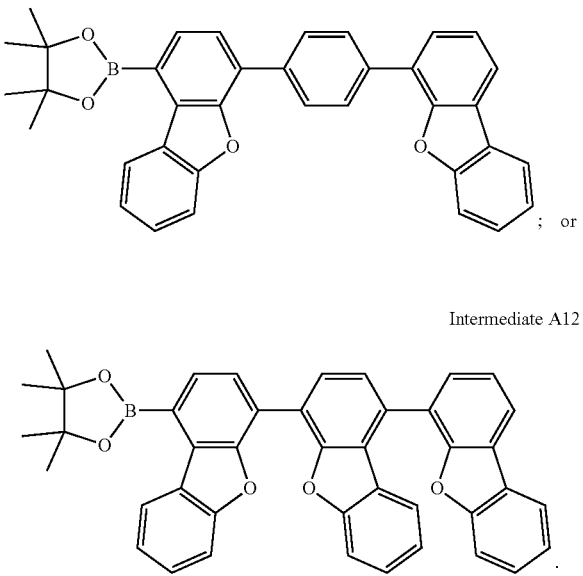

Intermediate A11

; or

Intermediate A12

Synthesis of Intermediate An-L

The foresaid Intermediate An-4, for example, Intermediates A1-4 to A6-4, or the foresaid Intermediate A'n-4, for example, Intermediates A'7-4 to A'8-4, could be further inserted with a phenylene group to obtain Intermediate An-4-L through step 4'-1.

Intermediate An-L used for preparing a novel compound was synthesized by the following steps. The general synthesis pathway of the Intermediate An-L was summarized in Scheme A4-L.

Scheme A4-L

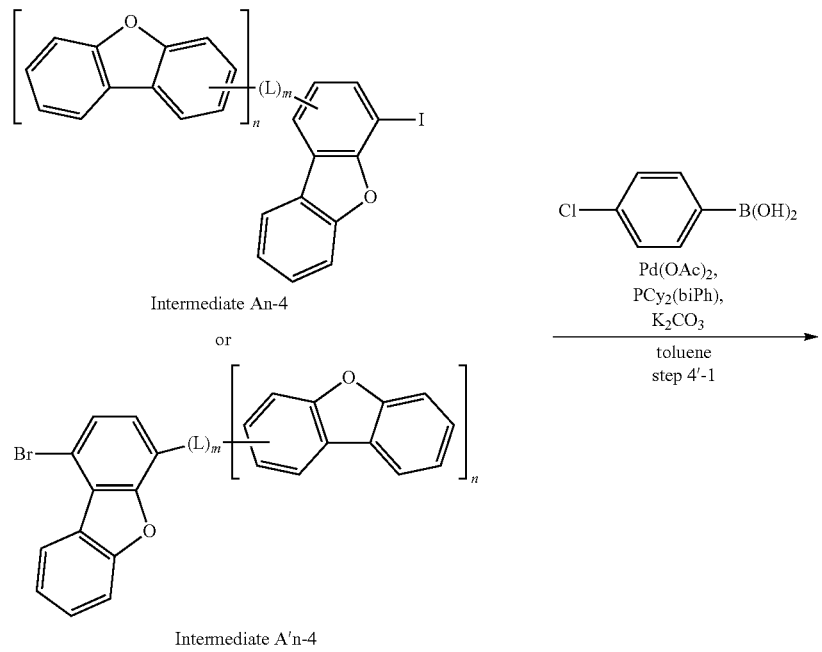

Intermediate An-4
or
Intermediate A'n-4

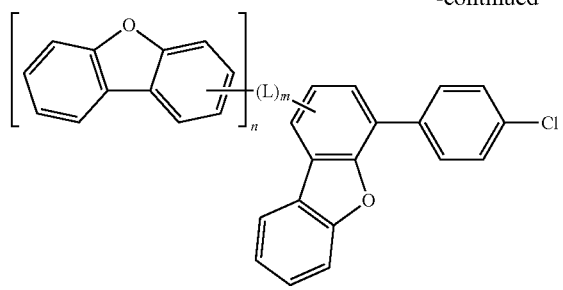
or
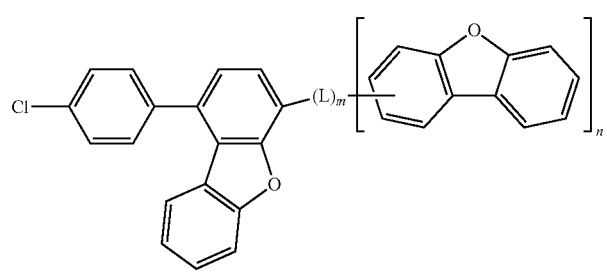
Intermediate An-4-L
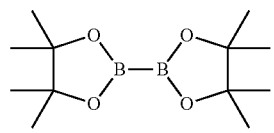
PdCl$_2$(dppf)
KOAc
1,4-dioxane
—————————→
step 4'-2
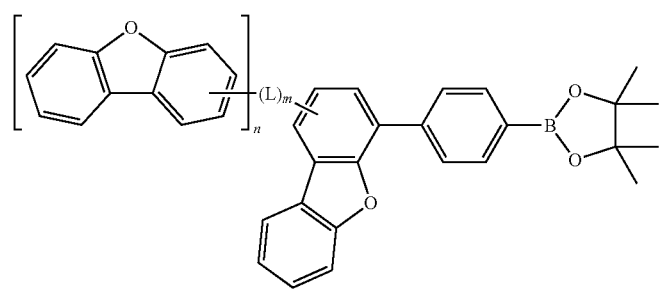
or
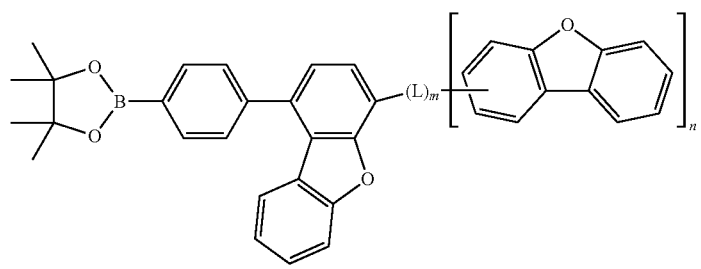
Intermediate An-L In Scheme A4-L, L, m, and n are as stated in Scheme A1.

Step 4'-1: Synthesis of Intermediate A1-4-L

Taking Intermediate A1-4-L as an example of Intermediate An-4-L, the synthesis pathway of the Intermediate A1-4-L was summarized in Scheme A4-1-L.

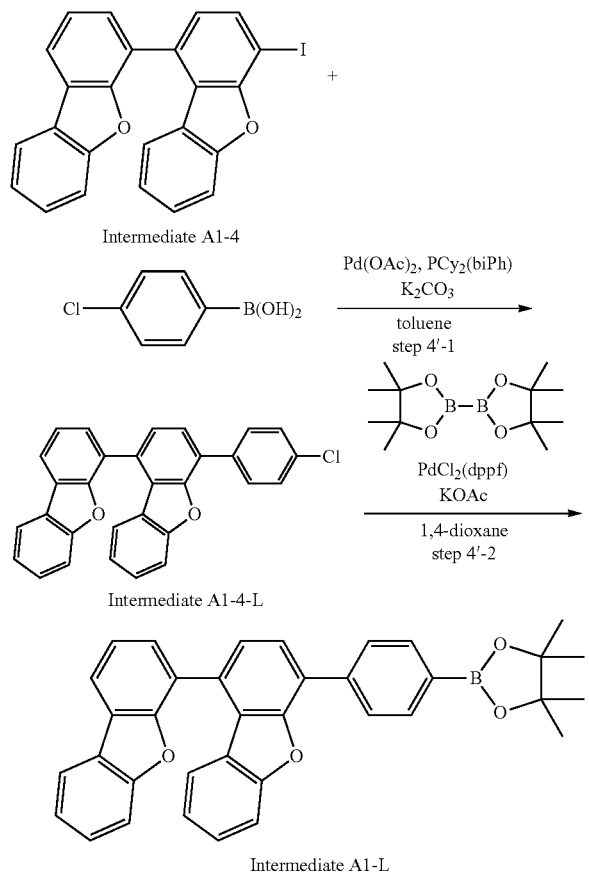

A mixture of Intermediate A1-4 (1-(dibenzofuran-4-yl)-4-iododibenzofuran) (50.0 g 1.0 eq), 4-chlorophenylboronic acid (1.05 eq, CAS No. 1679-18-1), $Pd(OAc)_2$ (0.01 eq), $PCy_2$(2-biPh) (0.04 eq), and $K_2CO_3$ (2.0 eq) was in a mixed solution of toluene (340 mL), ethanol (34 mL) and $H_2O$ (72 mL). The reaction mixture was heated to about 80° C. under reflux and stirred for 16 hours under nitrogen atmosphere. After the completion of the reaction, the reaction mixture was cooled to room temperature, and the crude product was extracted and collected by the organic layer. The organic layer was dried over $MgSO_4$, separated by filtration and concentrated to dryness. A resulting residue was purified by silica gel column chromatography to obtain 43 g of white solid product. The yield of step 4'-1 was 89%.

The white solid product was identified as Intermediate A1-4-L by a FD-MS analysis. FD-MS analysis: $C_{30}H_{17}ClO_2$: theoretical value of 444.91 and observed value of 444.91.

Step 4'-2: Synthesis of Intermediate A1-L

In step 4'-2, Intermediate A1-L, which also can be used for preparing a novel compound, was synthesized in a similar manner as Intermediate A1 through step 4, except that the starting material Intermediate A1-4 was replaced by Intermediate A1-4-L. The yield of step 4'-2 was 89%.

The white product was identified as Intermediate A1-L by a FD-MS analysis. FD-MS analysis: $C_{36}H_{29}BO_4$: theoretical value of 536.42 and observed value of 536.42.

Modifications of Intermediates A1-L

In addition to Intermediate A1-L, one person skilled in the art can adopt other starting materials and successfully synthesize other desired intermediates through a reaction mechanism similar to Scheme A4-1-L. Applicable modifications of Intermediate A1-L may be, for example, but not limited to, Intermediates A2-L to A19-L as follows.

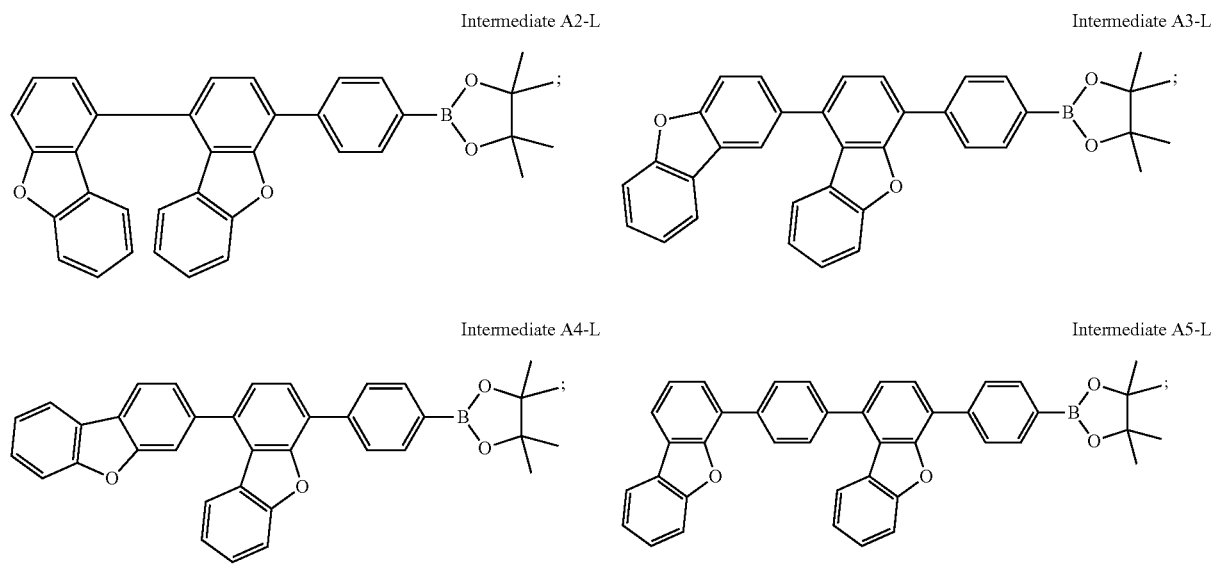

-continued
Intermediate A6-L
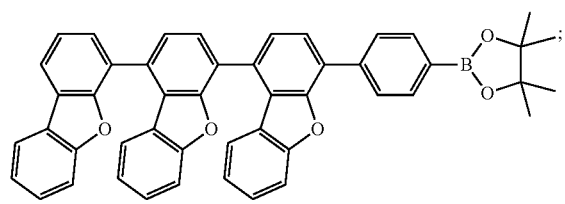
Intermediate A7-L
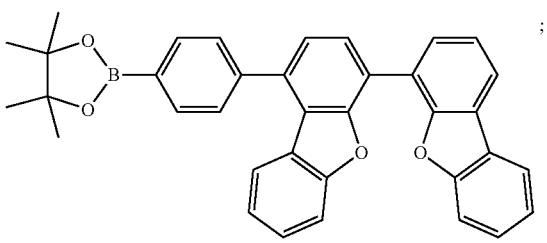
Intermediate A8-L
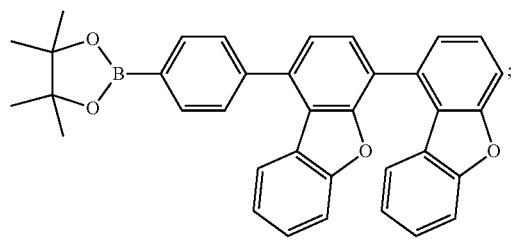
Intermediate A9-L
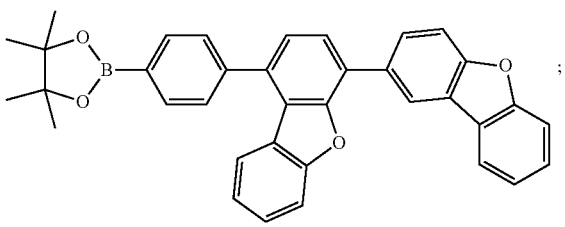
Intermediate A10-L
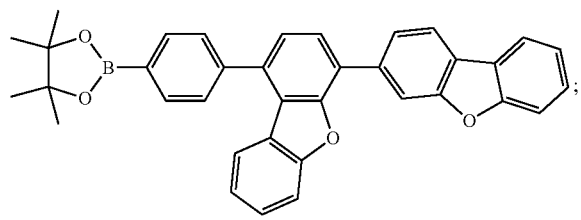
Intermediate A11-L
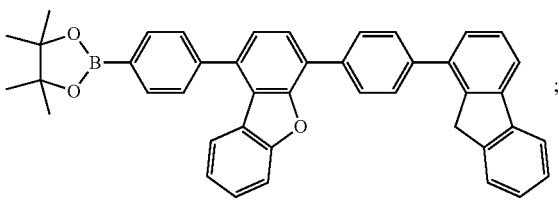
Intermediate A12-L
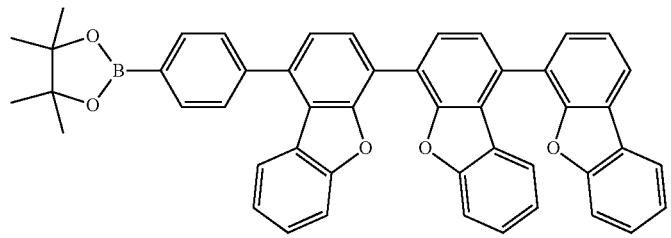
Intermediate A13-L
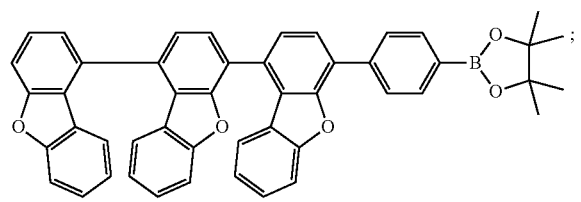
Intermediate A14-L
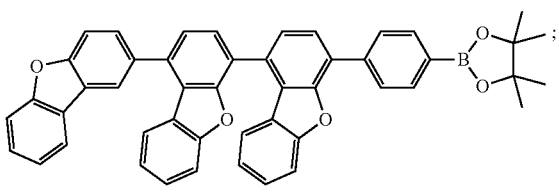
Intermediate A15-L
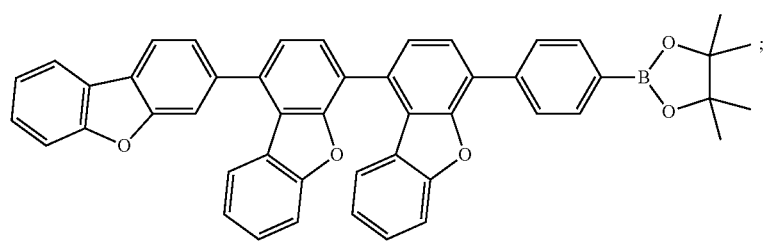

-continued

Intermediate A16-L

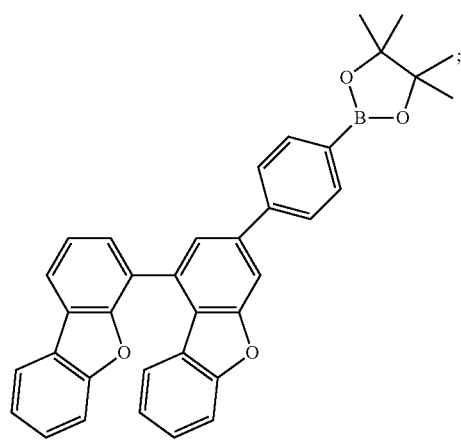

Intermediate A17-L

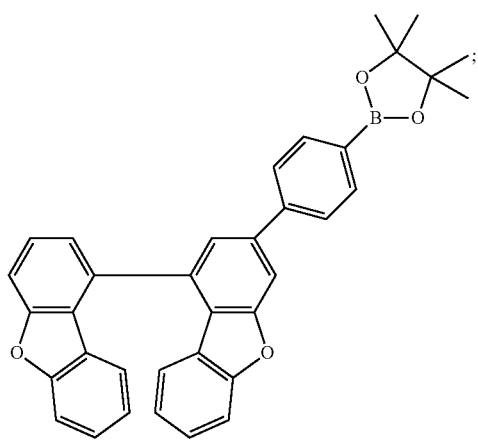

Intermediate A18-L

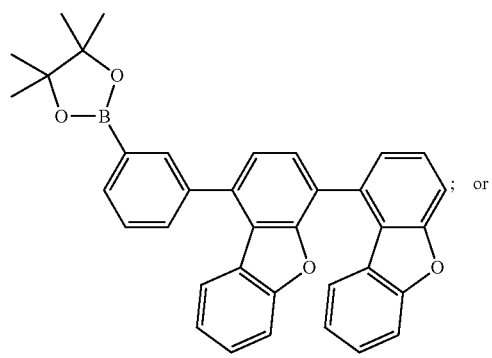

; or

Intermediate A19-L

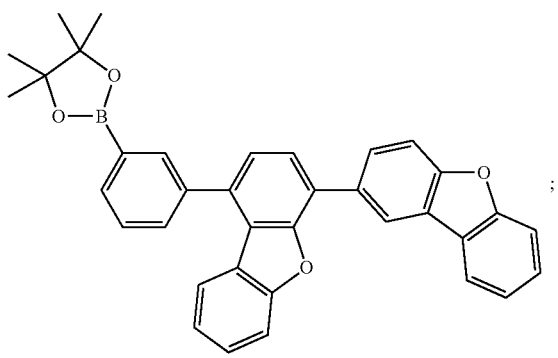

;

Synthesis of Novel Compounds

Each of the foresaid Intermediates, e.g., Intermediates An and An-L could be reacted with various reactants to synthesize various claimed novel compounds. The general synthesis pathway of the claimed novel compound was summarized in Scheme I. In the following Scheme I, "Reactant An" may be any one of Reactants A1 to A10 as listed in Table 7, and "Intermediate A" may be any one of the foresaid Intermediates An and An-L or the like. The compounds were each synthesized by the following steps.

Scheme I

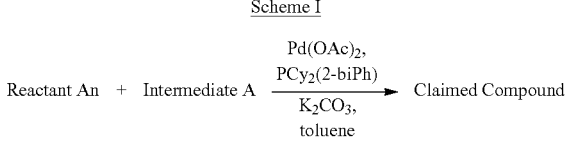

TABLE 7

| chemical structure and CAS No. of Reactants A1 to A10. | | | |
|---|---|---|---|
| Reactant No. | Reactant A1 | Reactant A2 | Reactant A3 |
| Chemical Structure | | | |
| CAS No. | [23674-20-6] | [1304129-94-9] | [400607-04-7] |

TABLE 7-continued chemical structure and CAS No. of Reactants A1 to A10.

| Reactant No. | Reactant A4 | Reactant A5 | Reactant A6 |
|---|---|---|---|
| Chemical Structure | 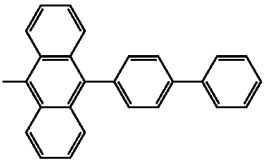 | | |
| CAS No. | [400607-05-8] | [474688-74-9] | [1092390-01-6] |

| Reactant No. | Reactant A7 | Reactant A8 |
|---|---|---|
| Chemical Structure | 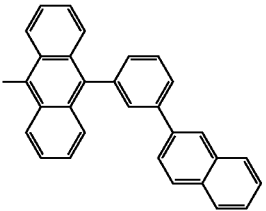 | |
| CAS No. | [944801-33-6] | [866611-29-2] |

| Reactant No. | Reactant A9 | Reactant A10 |
|---|---|---|
| Chemical Structure | 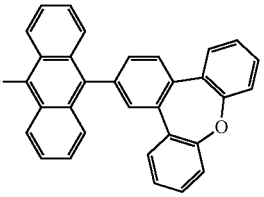 | |

Synthesis of Reactant A9

Reactant A9 used for preparing a novel compound was synthesized by the following steps. The synthesis pathway of the Reactant A9 was summarized in Scheme R1.

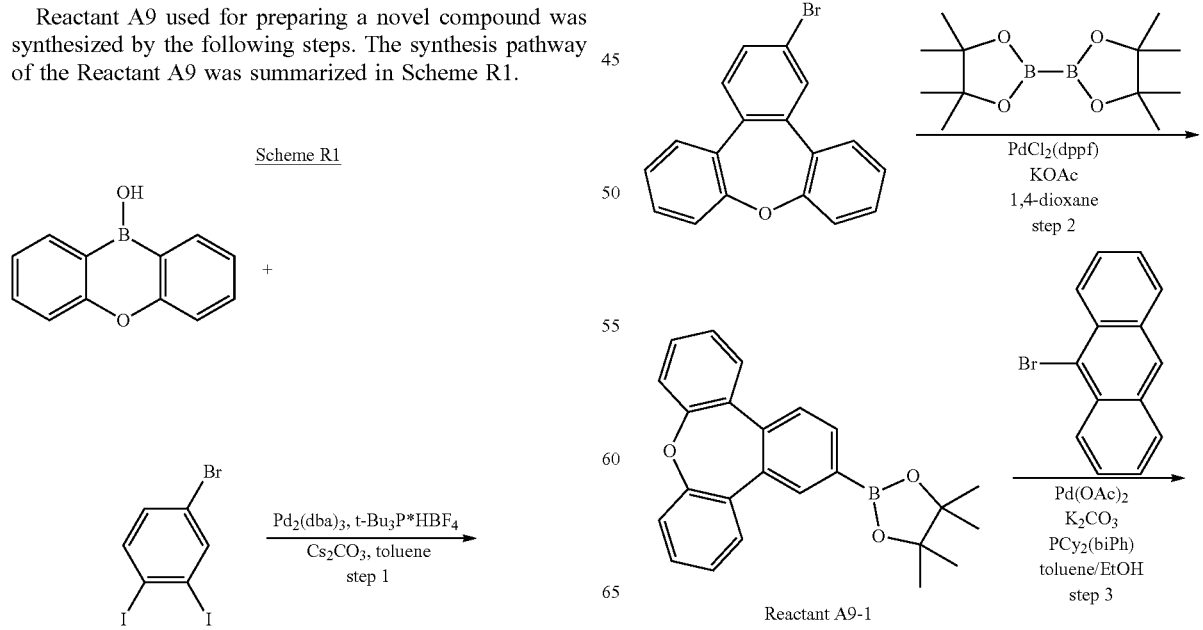

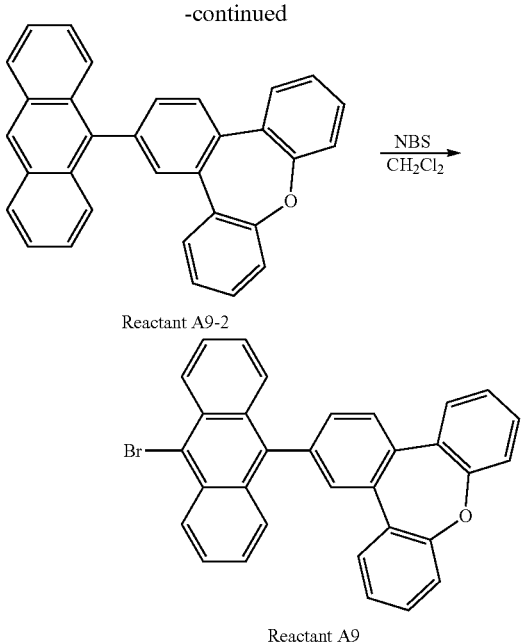

Reactant A9-2

Reactant A9

The step 1 was performed to obtain a starting material for Reactant A9-1. The starting material can adopt other materials such as Intermediate B in U.S. patent application Ser. No. 15/679,379, and successfully synthesize other desired materials through a reaction mechanism similar to the synthetic method of Intermediate B in U.S. patent application Ser. No. 15/679,379.

Step 2: Synthesis of Reactant A9-1

A mixture of the starting material (1.0 eq), bis(pinacolato) diboron (1.20 eq), PdCl$_2$(dppf) (0.02 eq), and KOAc (2.0 eq) in 1,4-dioxane (165 mL) was stirred at 95° C. for 16 hours under nitrogen atmosphere. After cooling to room temperature, the crude product was extracted with H$_2$O and collected by the organic layer. The organic layer was dried over MgSO$_4$, separated by filtration and then concentrated to dryness. A resulting residue was purified by silica gel column chromatography to obtain 20 g of solid product. The yield of step 2 was 88%.

The product was identified as Reactant A9-1 by a field desorption mass spectroscopy (FD-MS) analysis. FD-MS analysis: C$_{24}$H$_{23}$BO$_3$: theoretical value of 370.25 and observed value of 370.25.

Step 3: Synthesis of Reactant A9-2

A mixture of Reactant A9-1 (1.25 eq), 9-bromoanthracene (10.0 g, 1.0 eq), Pd(OAc)$_2$ (0.01 eq), PCy$_2$(biPh) (0.04 eq), K$_2$CO$_3$ (2.0 eq) was in a mixed solution of toluene (120 mL), ethanol (12 mL) and H$_2$O (25.0 mL). The reaction mixture was heated to about 80° C. under reflux and stirred for 16 hours under nitrogen atmosphere. After the completion of the reaction, the reaction mixture was cooled to room temperature, and the crude product was extracted and collected by the organic layer. The organic layer was dried over MgSO$_4$, separated by filtration and concentrated to dryness. A resulting residue was purified by silica gel column chromatography to obtain 12.0 g of white solid product. The yield of step 3 was 73.38%. The white solid product was identified as Reactant A9-2 by a field desorption mass spectroscopy (FD-MS) analysis. FD-MS analysis: C$_{32}$H$_{20}$O: theoretical value of 420.5 and observed value of 420.5.

Step 4: Synthesis of Reactant A9

Before the reaction was initiated, Reactant A9-2 (12 g, 1.0 eq) was vacuated and then filled with argon gas. Subsequently, Reactant A9-2 was dissolved in dichloromethane (120 mL) and stirred at 0° C. for 10 minutes. N-bromosuccinimide (NBS, 1.75 eq) was then added into the foresaid solution, and the reactant mixture was stirred at ambient temperature for one day. After the completion of the reaction, the crude product was extracted with distilled water and ethyl acetate and collected by the organic layer. The organic layer was dried over MgSO$_4$ and solvent was removed by using a rotary evaporator. A resulting residue was purified by silica gel column chromatography to obtain 10.8 g of yellow solid product. The yield of step 4 was 75.78%. The yellow solid product was identified as Reactant A9 by a field desorption mass spectroscopy (FD-MS) analysis. FD-MS analysis: C$_{32}$H$_{19}$BrO: theoretical value of 499.4 and observed value of 499.4.

Synthesis of Reactant A10

Reactant A10 used for preparing a novel compound was synthesized by the following steps. The general synthesis pathway of the Reactant A10 was summarized in Scheme R2.

Scheme R2

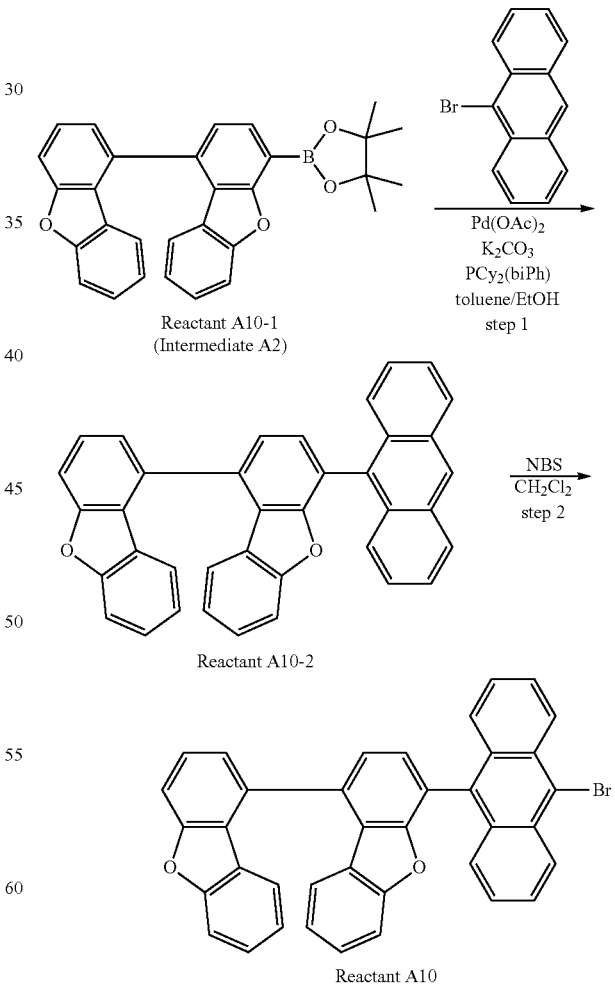

Reactant A10-1
(Intermediate A2)

Reactant A10-2

Reactant A10

Intermediate A2 was used as Reactant A10-1. One person skilled in the art can adopt other desired Intermediate An or Intermediate An-L and then successfully synthesize other Reactant An-2 and Reactant An through a reaction mechanism similar to Scheme R2.

Reactant A10 used for preparing a novel compound was synthesized in a similar manner as Reactant A9 through steps 3 and 4, except that the starting material Reactant A9-1 was replaced by Reactant A10-1.

The yield of step 1 was 88.2%. The Reactant A10-2 was identified by a field desorption mass spectroscopy (FD-MS) analysis. FD-MS analysis: $C_{38}H_{22}O_2$: theoretical value of 510.58 and observed value of 510.58.

The yield of step 2 was 85%. The Reactant A10 was identified by a field desorption mass spectroscopy (FD-MS) analysis. FD-MS analysis: $C_{38}H_{21}BrO_2$: theoretical value of 589.48 and observed value of 589.48.

Scheme I: Synthesis of Compounds 1 to 22

In Scheme I, a mixture of Intermediate A (1.05 eq), Reactant An (1.0 eq), $Pd(OAc)_2$ (0.01 eq), $PCy_2$(2-biPh) (0.04 eq), $K_2CO_3$ (2.0 eq) was in a mixed solution of toluene (30 mL), ethanol (3 mL) and $H_2O$ (3 mL). Subsequently, the reaction mixture was heated under reflux and stirred for 16 hours under nitrogen atmosphere. After the completion of the reaction, the reaction mixture was cooled to room temperature, and the crude product was extracted and collected by the organic layer. The organic layer was dried over $MgSO_4$, separated by filtration and concentrated to dryness. A resulting residue was purified by silica gel column chromatography to obtain 12.0 g of white solid product as the claimed novel compound.

Intermediate A and Reactant An adopted to synthesize Compounds 1 to 22 were listed in Table 8.

Another synthesis pathway of the claimed novel compound was summarized in Scheme II. Each of the foresaid Reactants Bn could be reacted with Reactant A10 or other Reactant An, which is synthesized through a reaction mechanism similar to Scheme R2, to synthesize various claimed novel compounds. In the following Scheme II, "Reactant Bn" may be any one of Reactants B1 to B6 as listed in Table 1, and "Reactant An" may be any one of the foresaid Reactant A10 or the like. The compounds were each synthesized by the following steps.

Scheme II

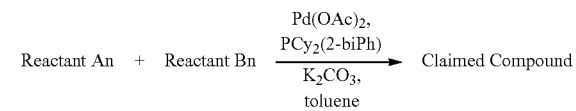

Take Reactant B1 and Reactant A10 as an example of starting materials in Scheme II.

Scheme II: Synthesis of Compound 23

In Scheme II, a mixture of Reactant B1 (1.05 eq), Reactant A10 (1.0 eq), $Pd(OAc)_2$ (0.01 eq), $PCy_2$(2-biPh) (0.04 eq), $K_2CO_3$ (2.0 eq) was in a mixed solution of toluene (30 mL), ethanol (3 mL) and $H_2O$ (3 mL). Subsequently, the reaction mixture was heated under reflux and stirred for 16 hours under nitrogen atmosphere. After the completion of the reaction, the reaction mixture was cooled to room temperature, and the crude product was extracted and collected by the organic layer. The organic layer was dried over $MgSO_4$, separated by filtration and concentrated to dryness. A resulting residue was purified by silica gel column chromatography to obtain 5.5 g of white solid product as the claimed novel compound.

Reactants An and Bn adopted to synthesize Compound 23 were listed in Table 8.

Figure 2:
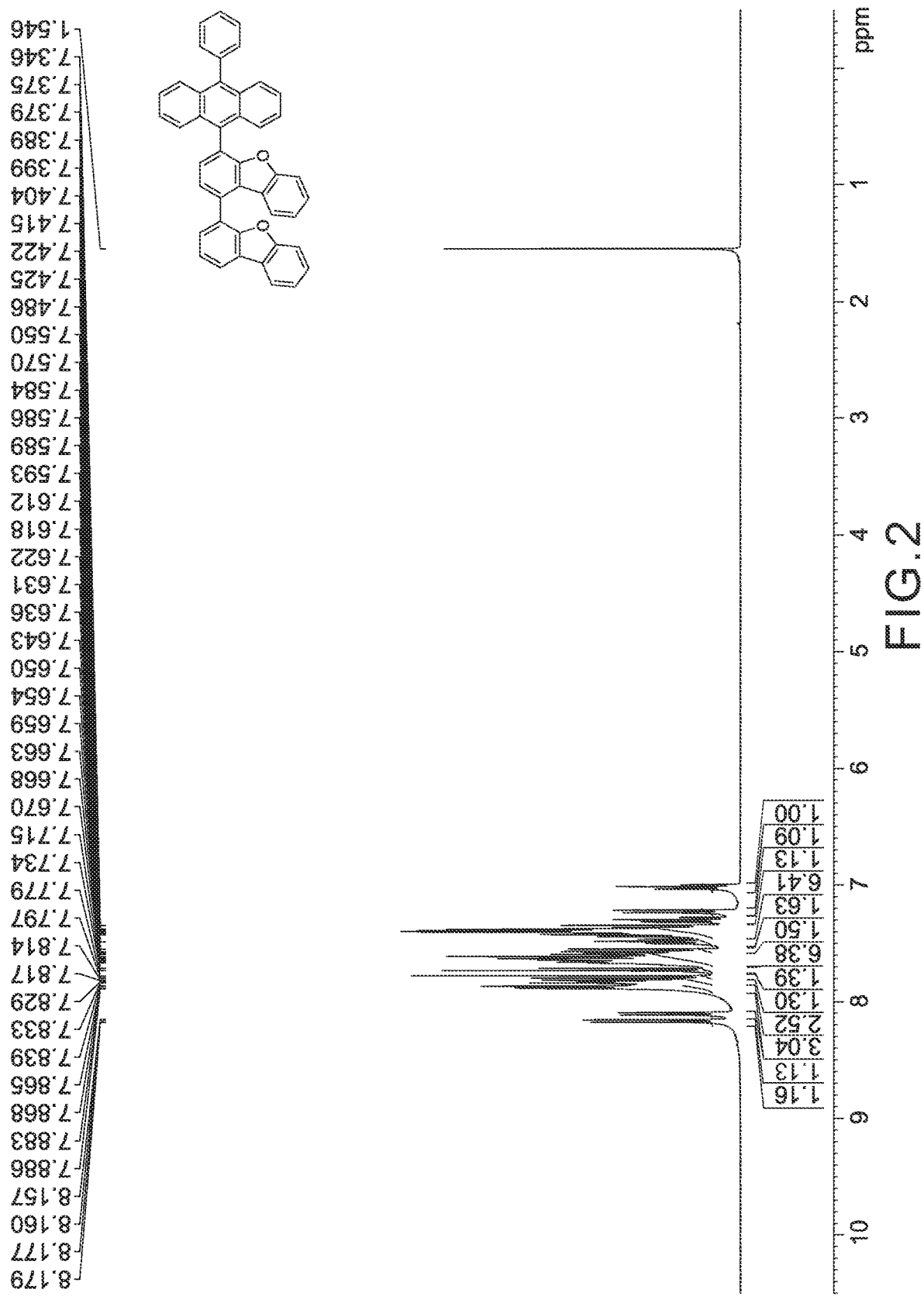
FIGS. 2 to 22 are respectively $^1$H nuclear magnetic resonance (NMR) spectra of Compounds 1 to 21.
Figure 3:
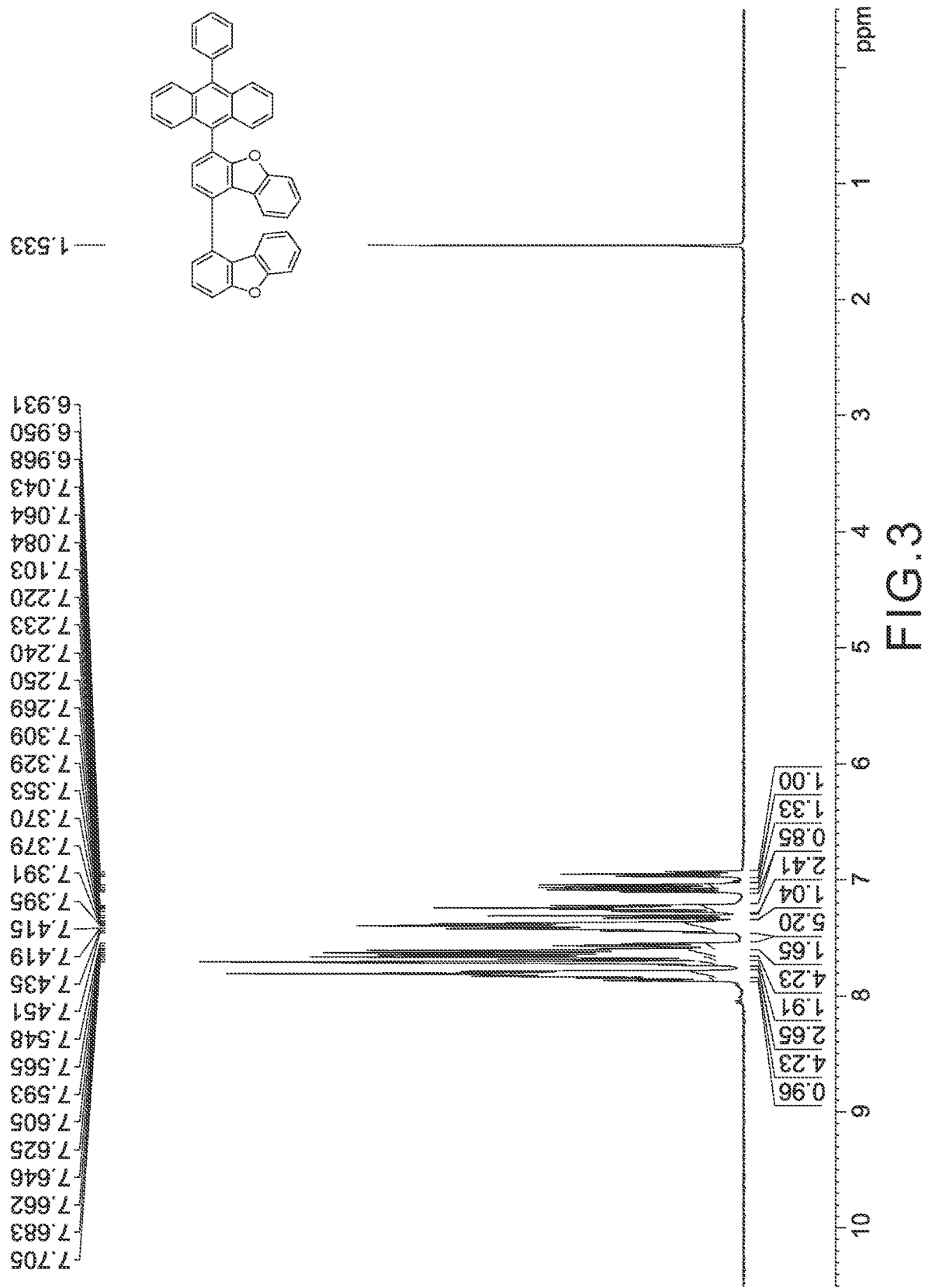
Figure 4:
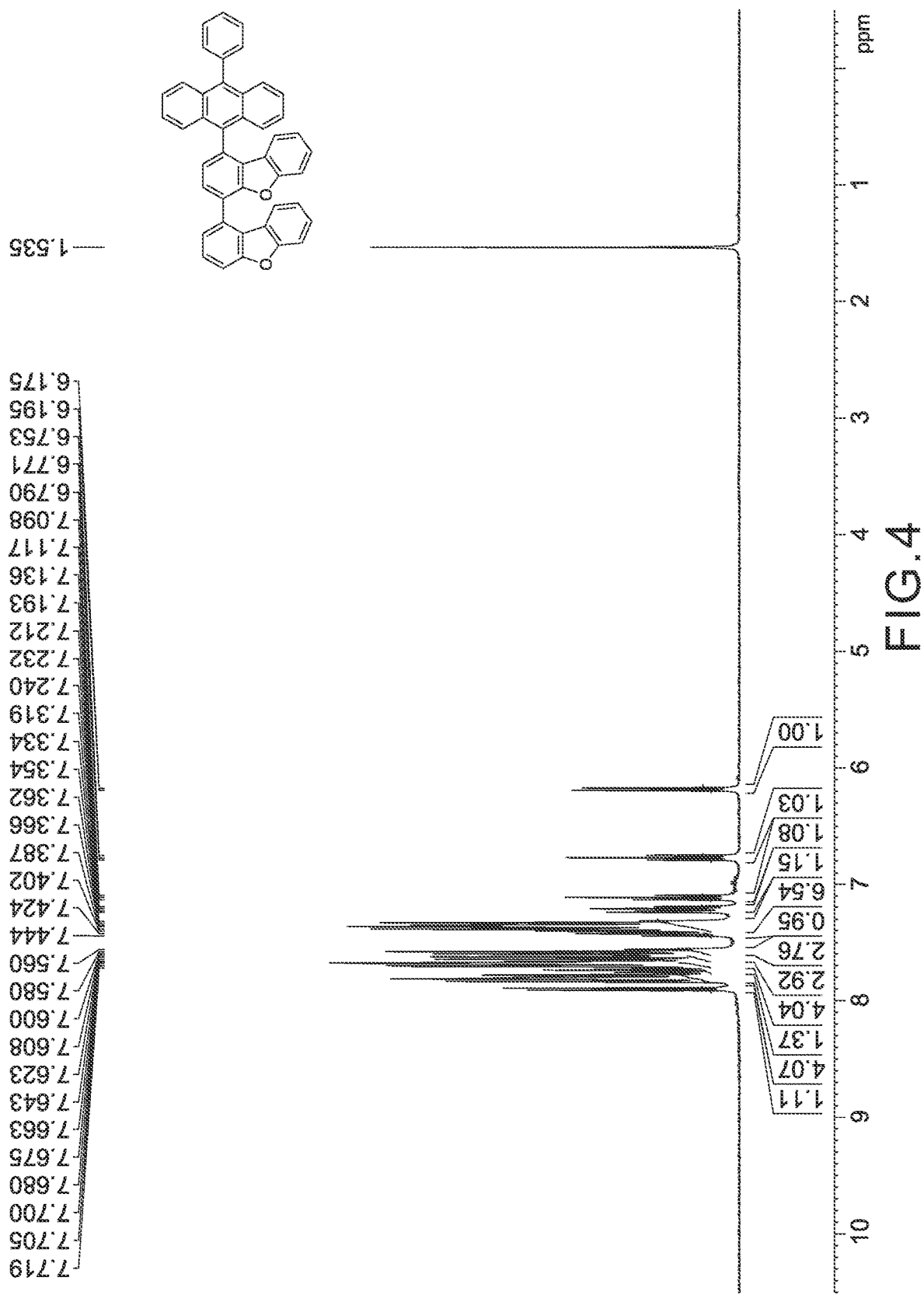
Figure 5:
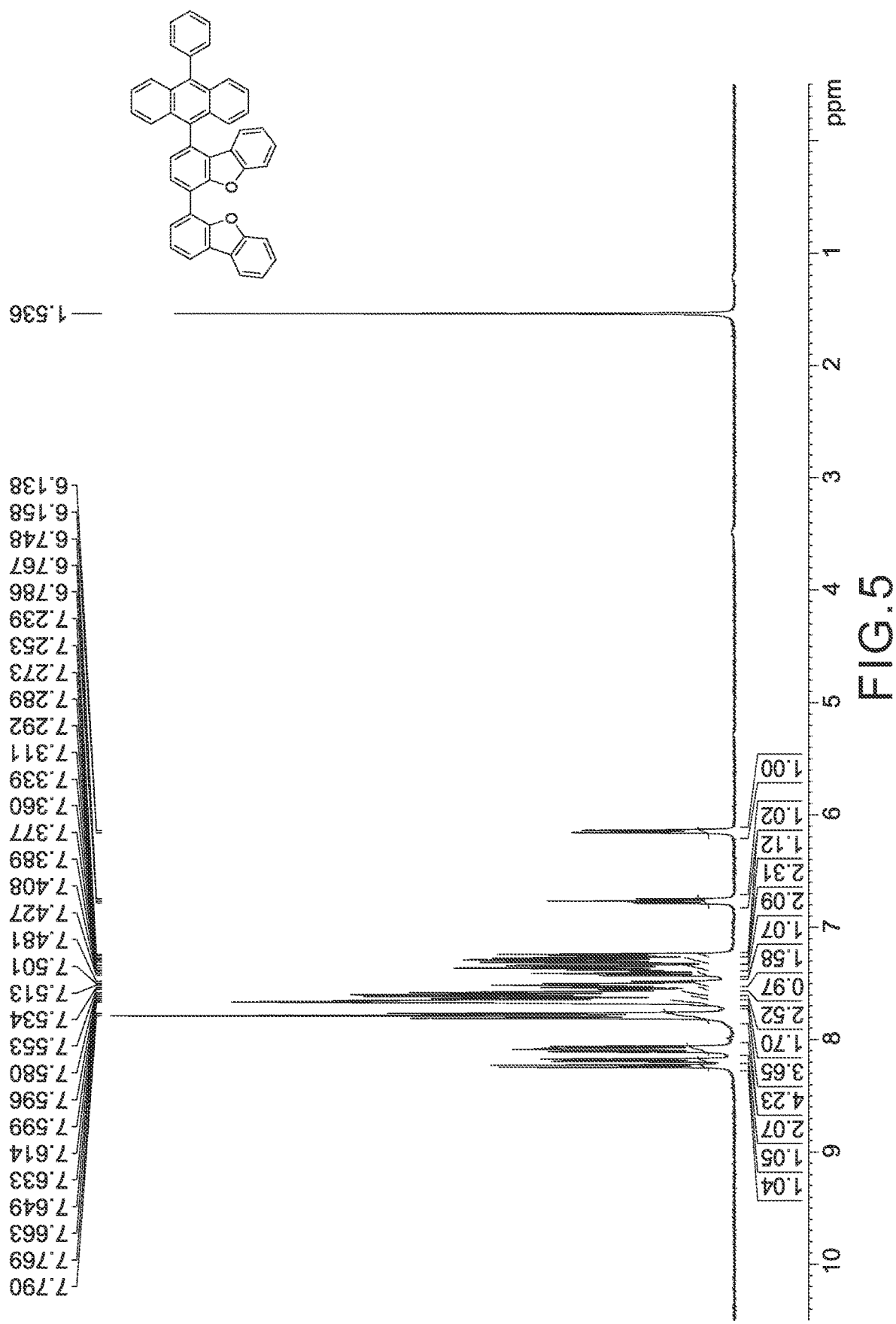
Figure 6:
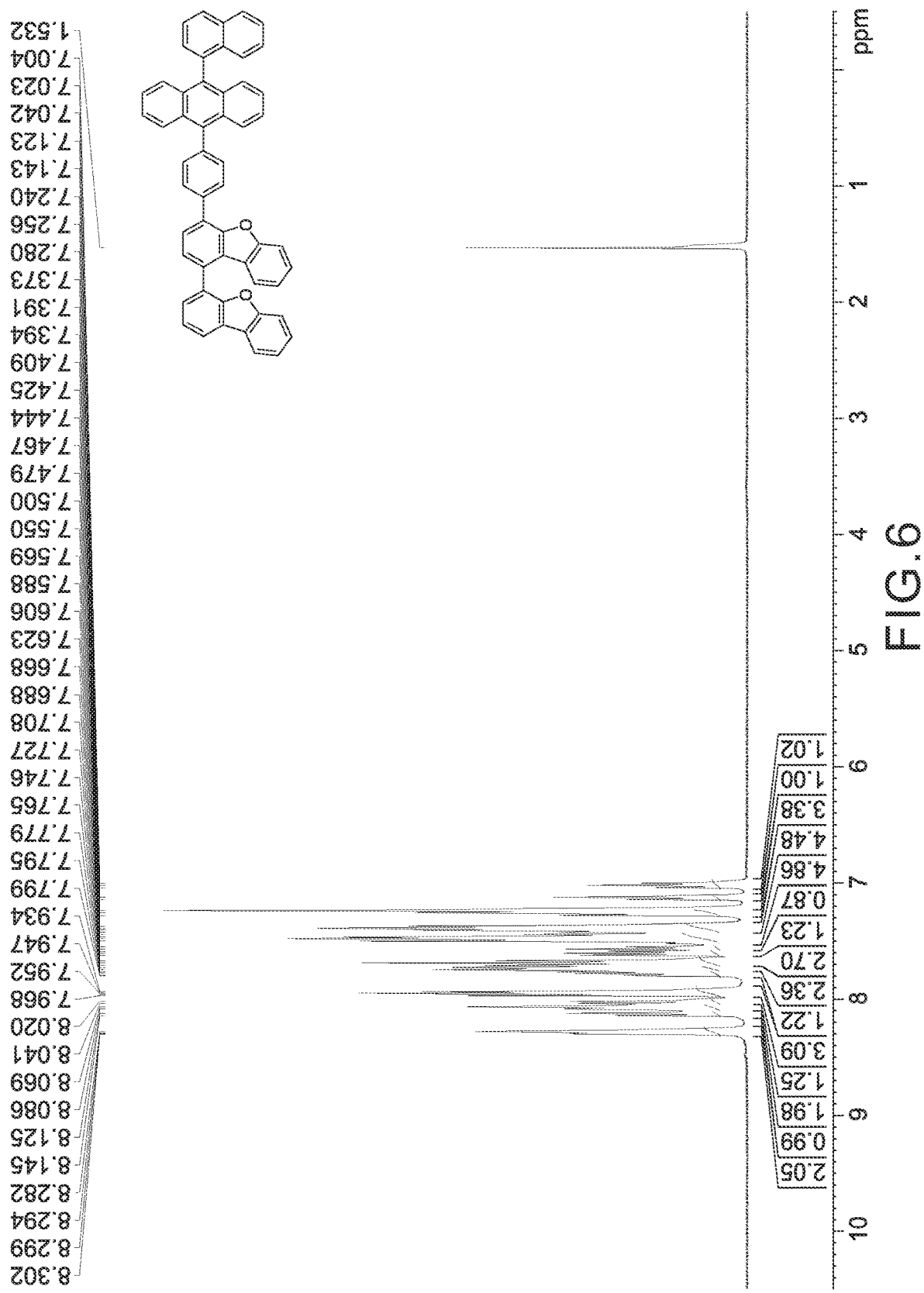
Figure 7:
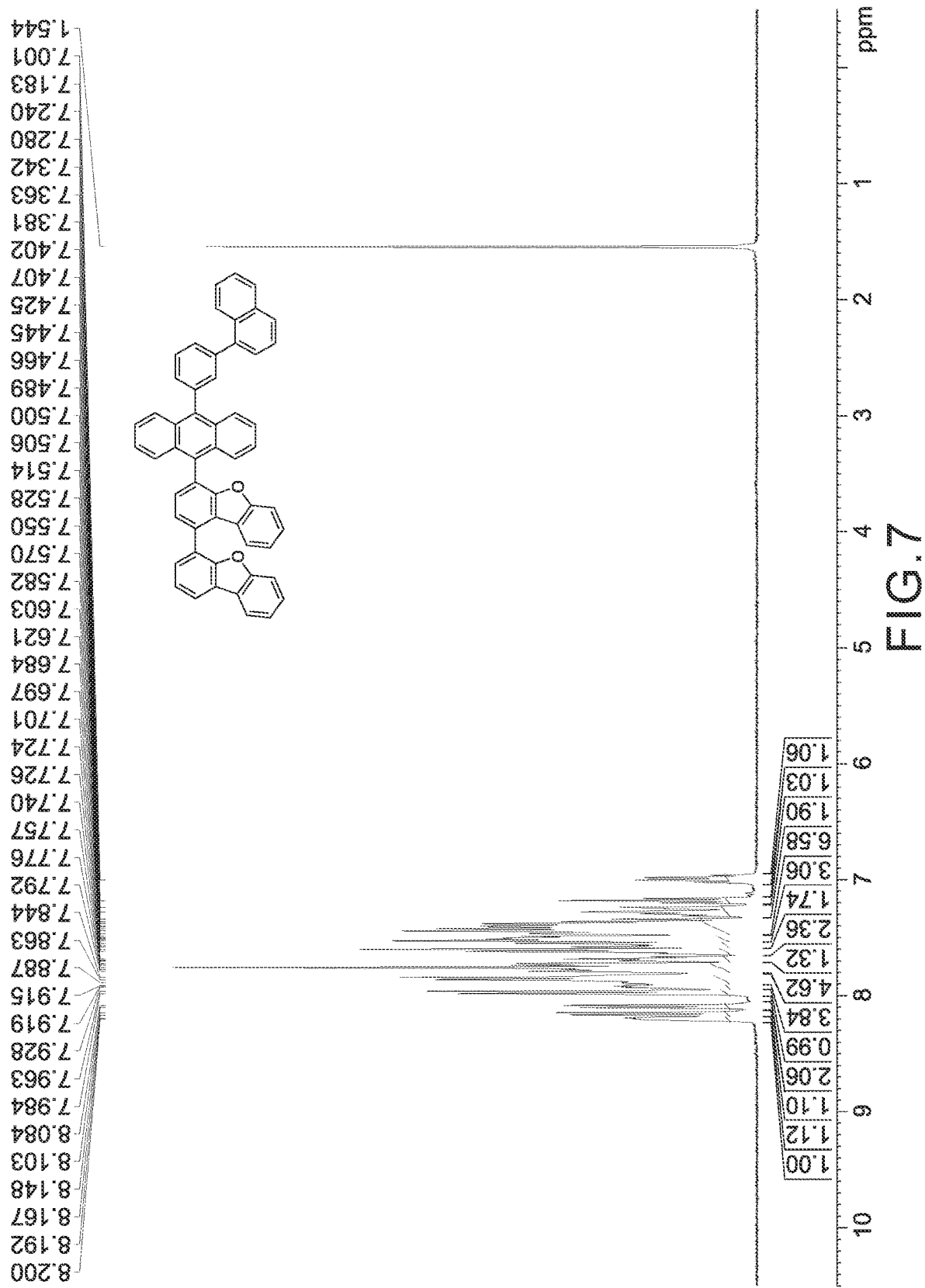
Figure 8:
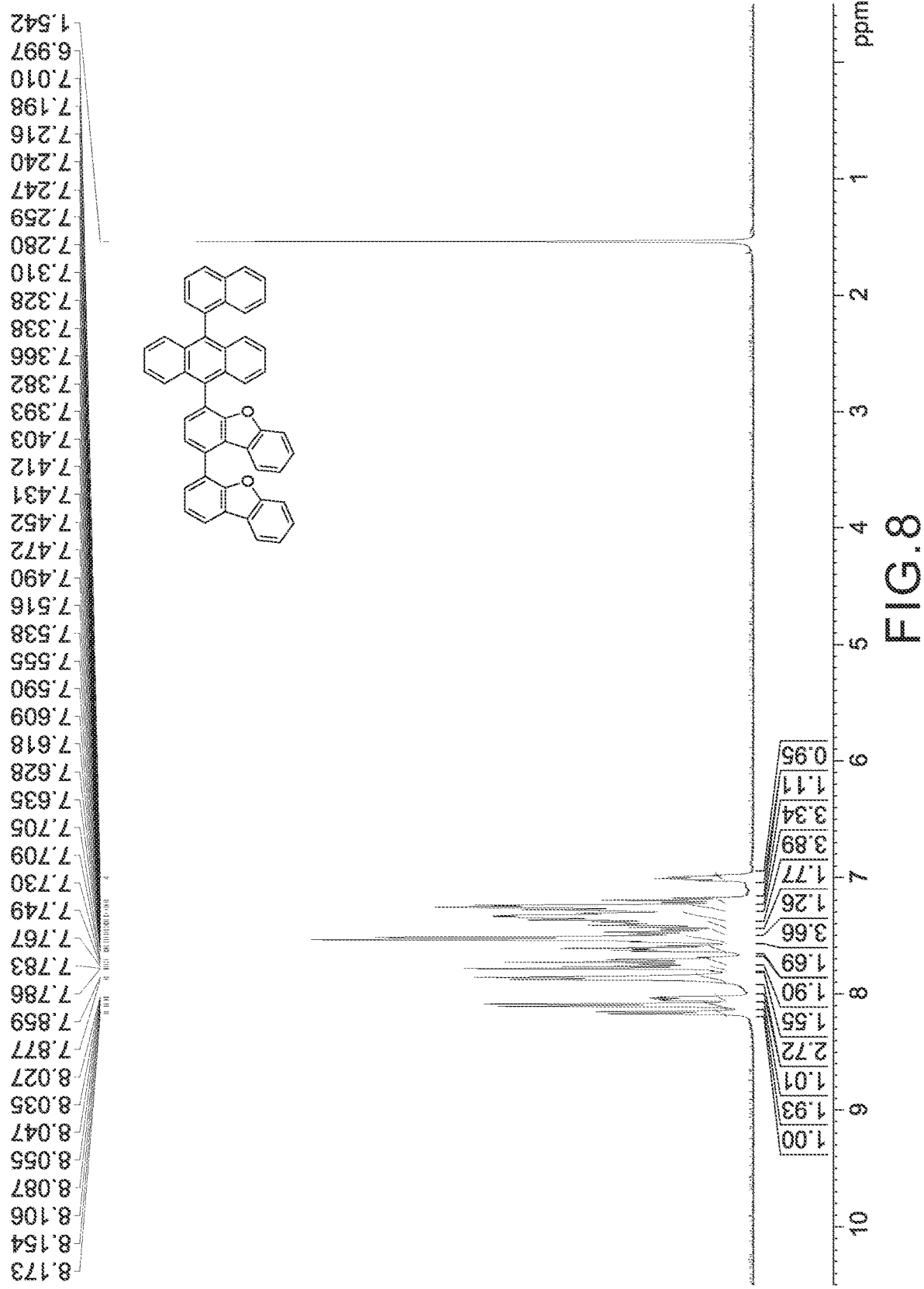
Figure 9:
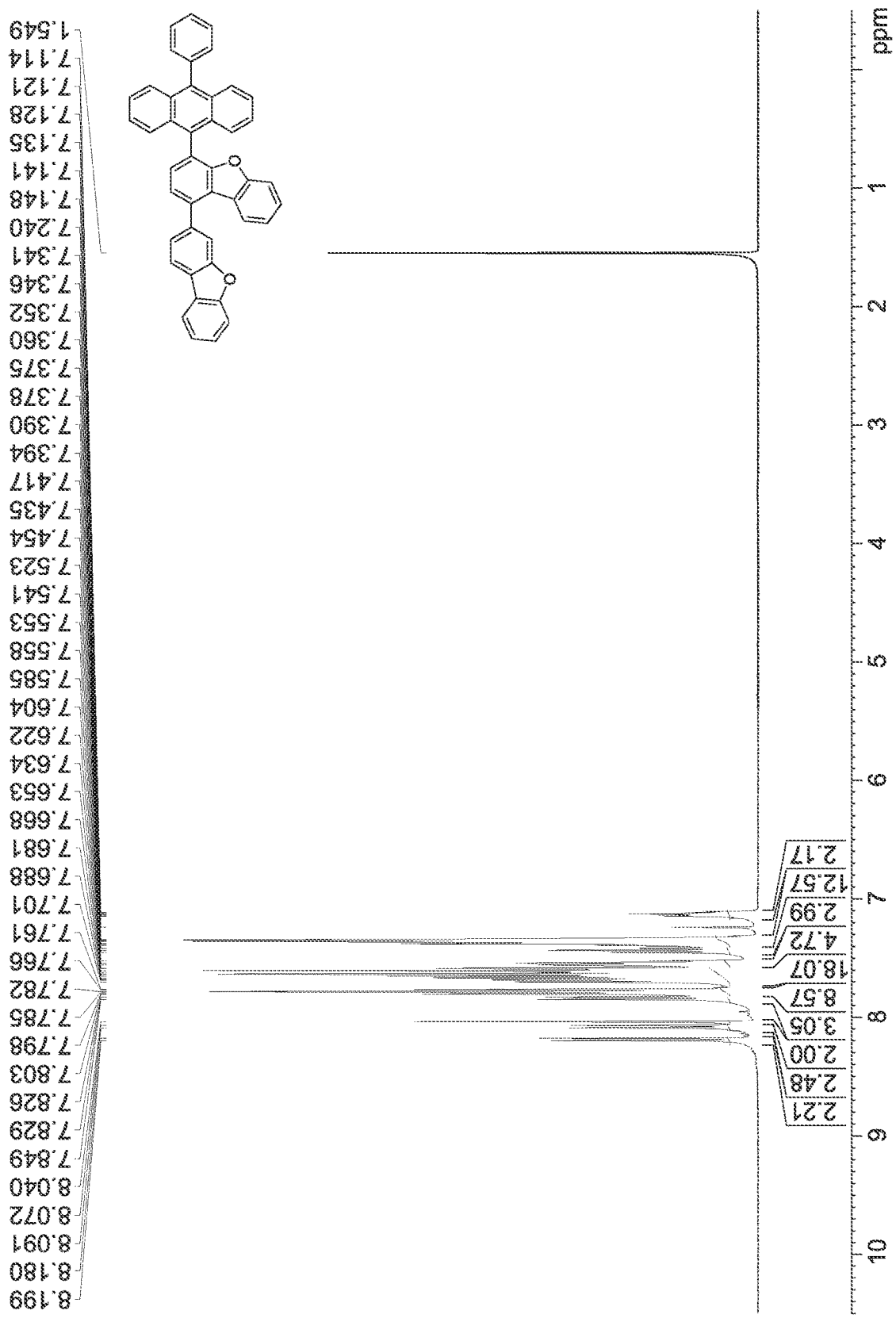
Figure 10:
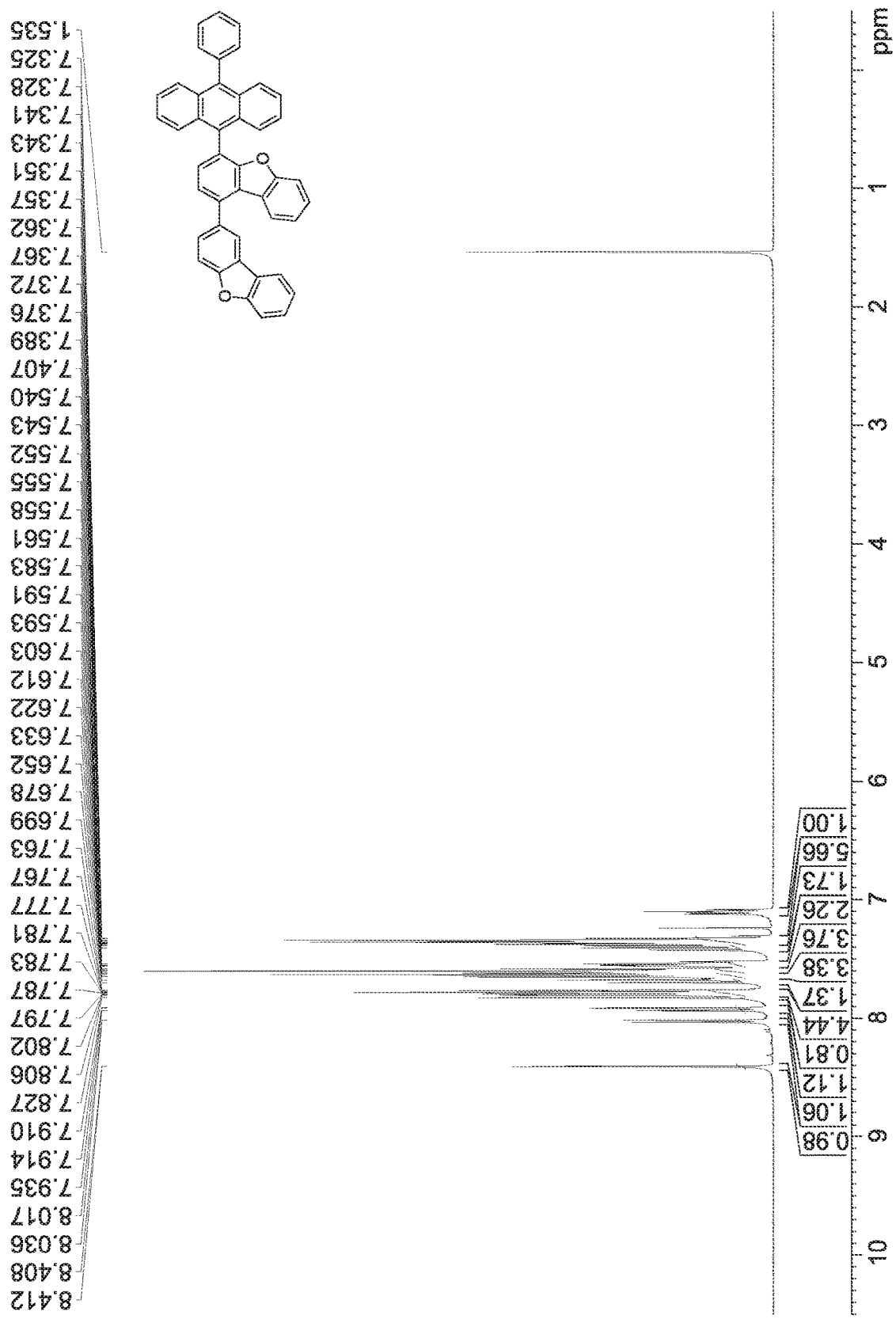
Figure 11:
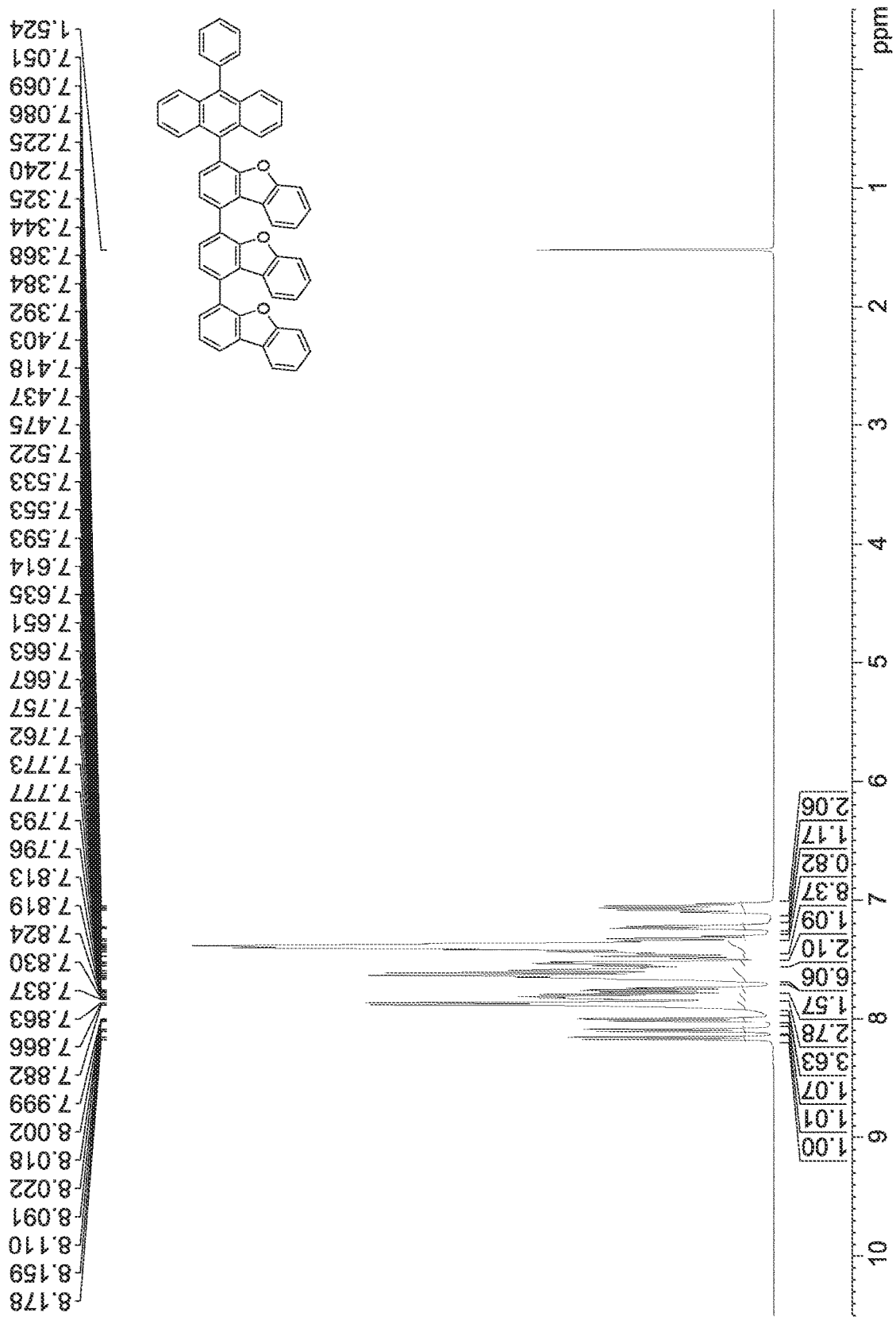
Figure 12:
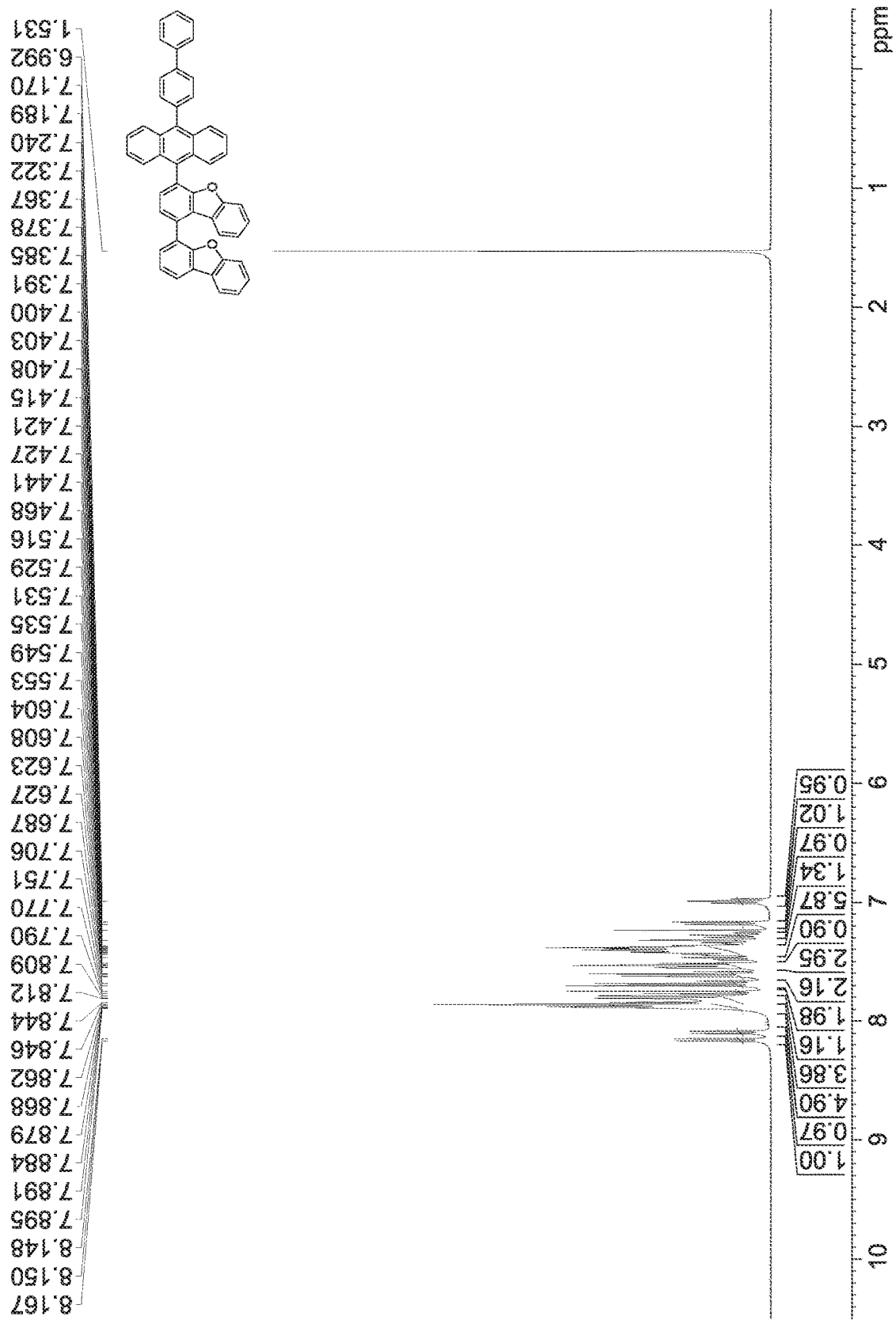
Figure 13:
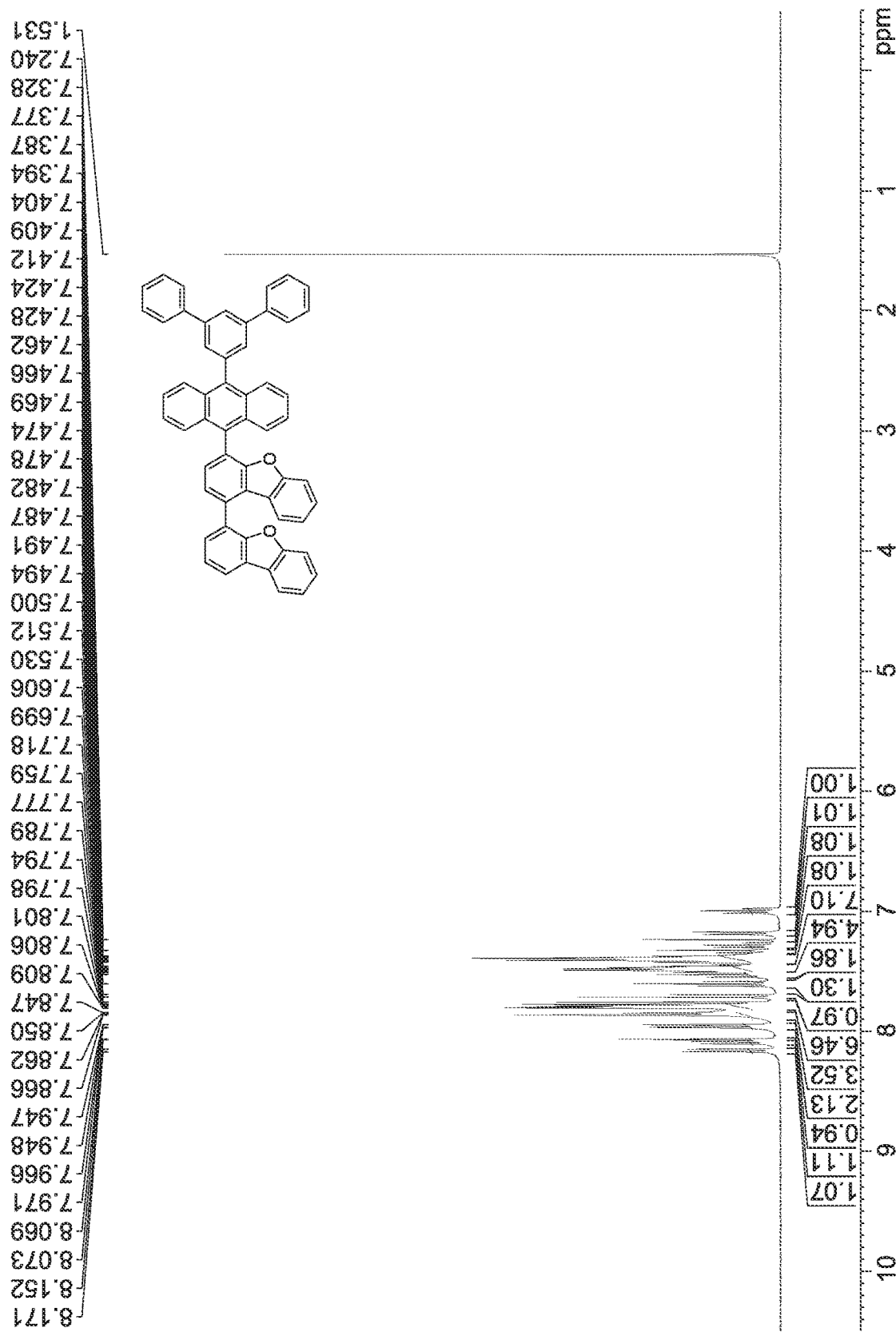
Figure 14:
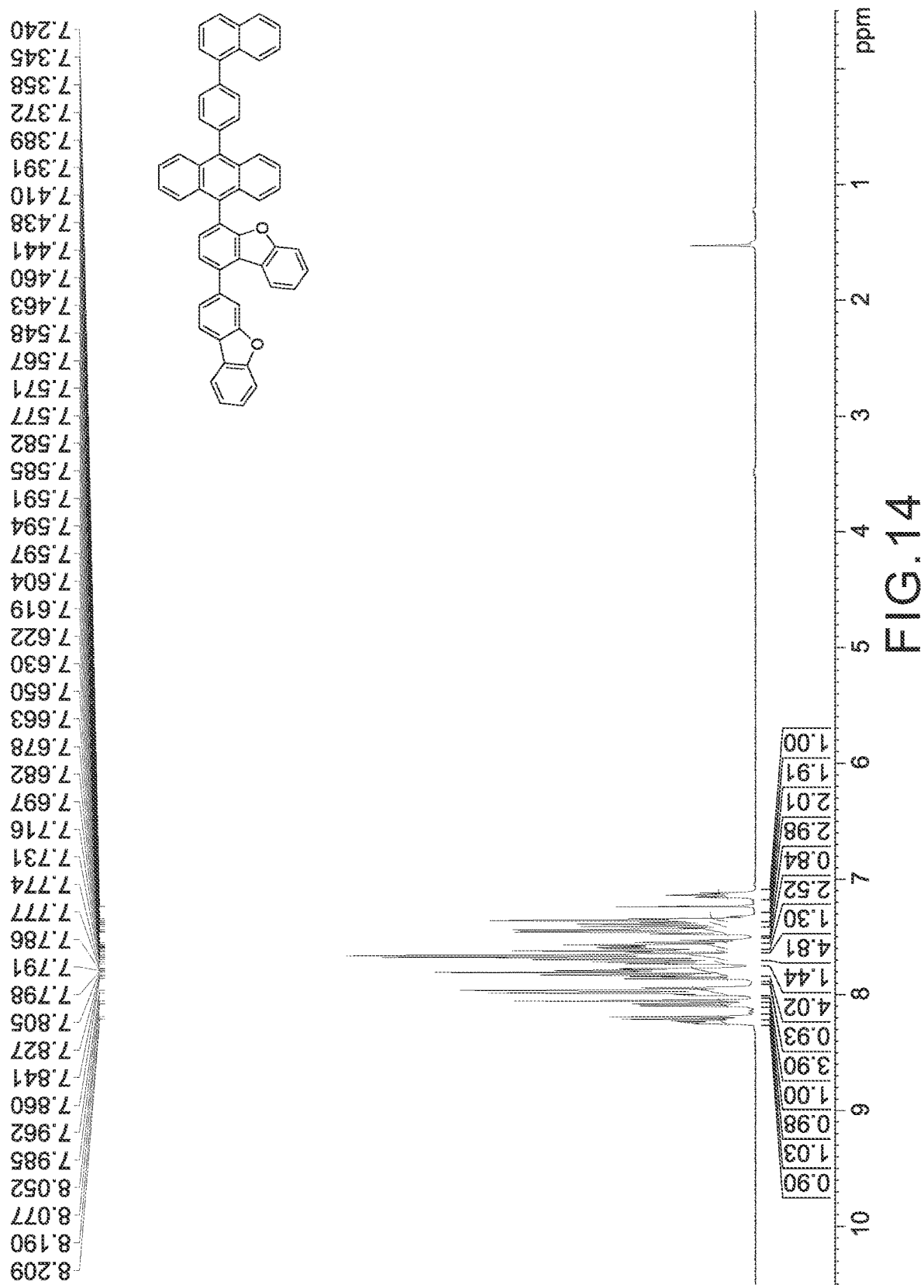
Figure 15:
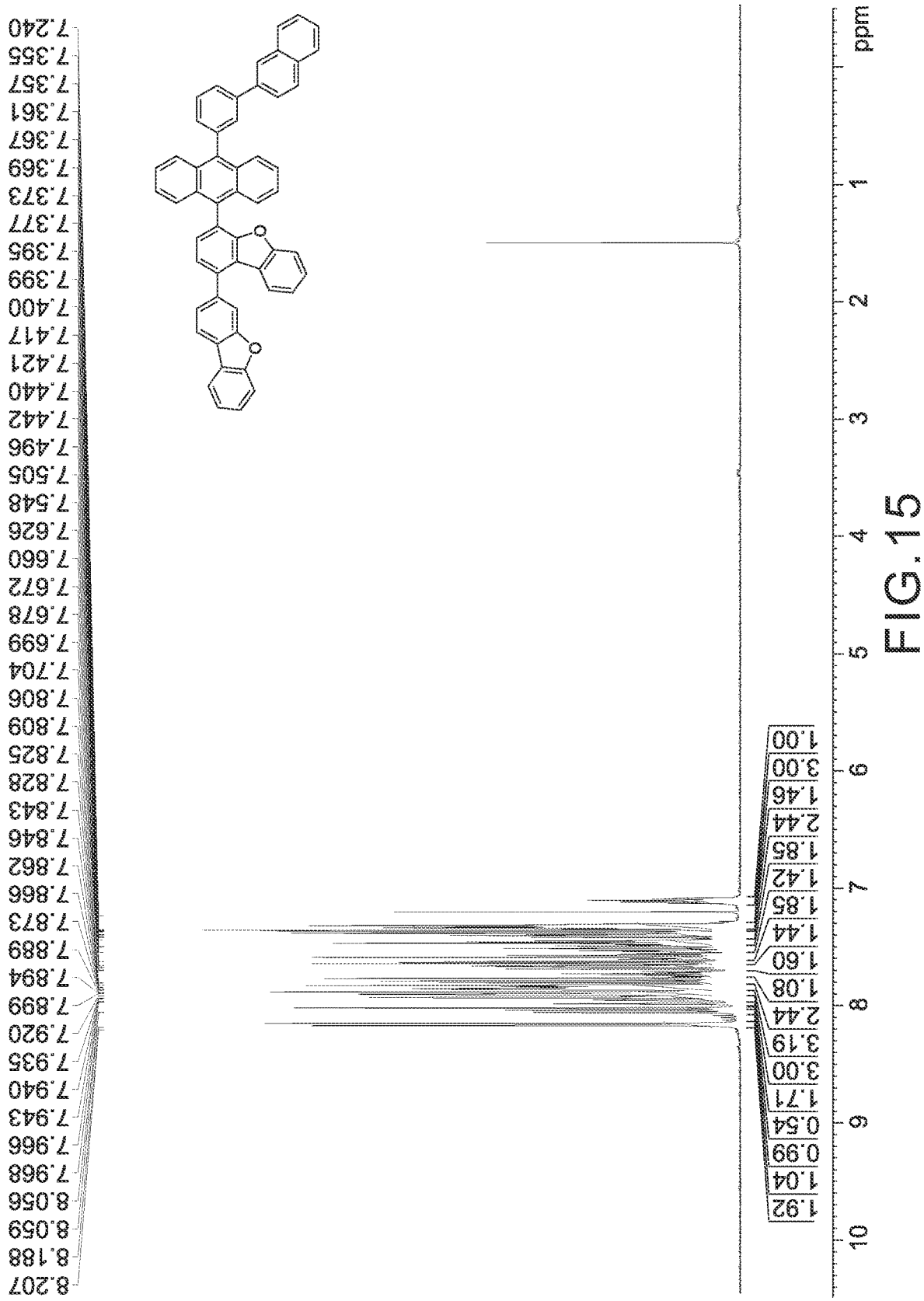
Figure 16:
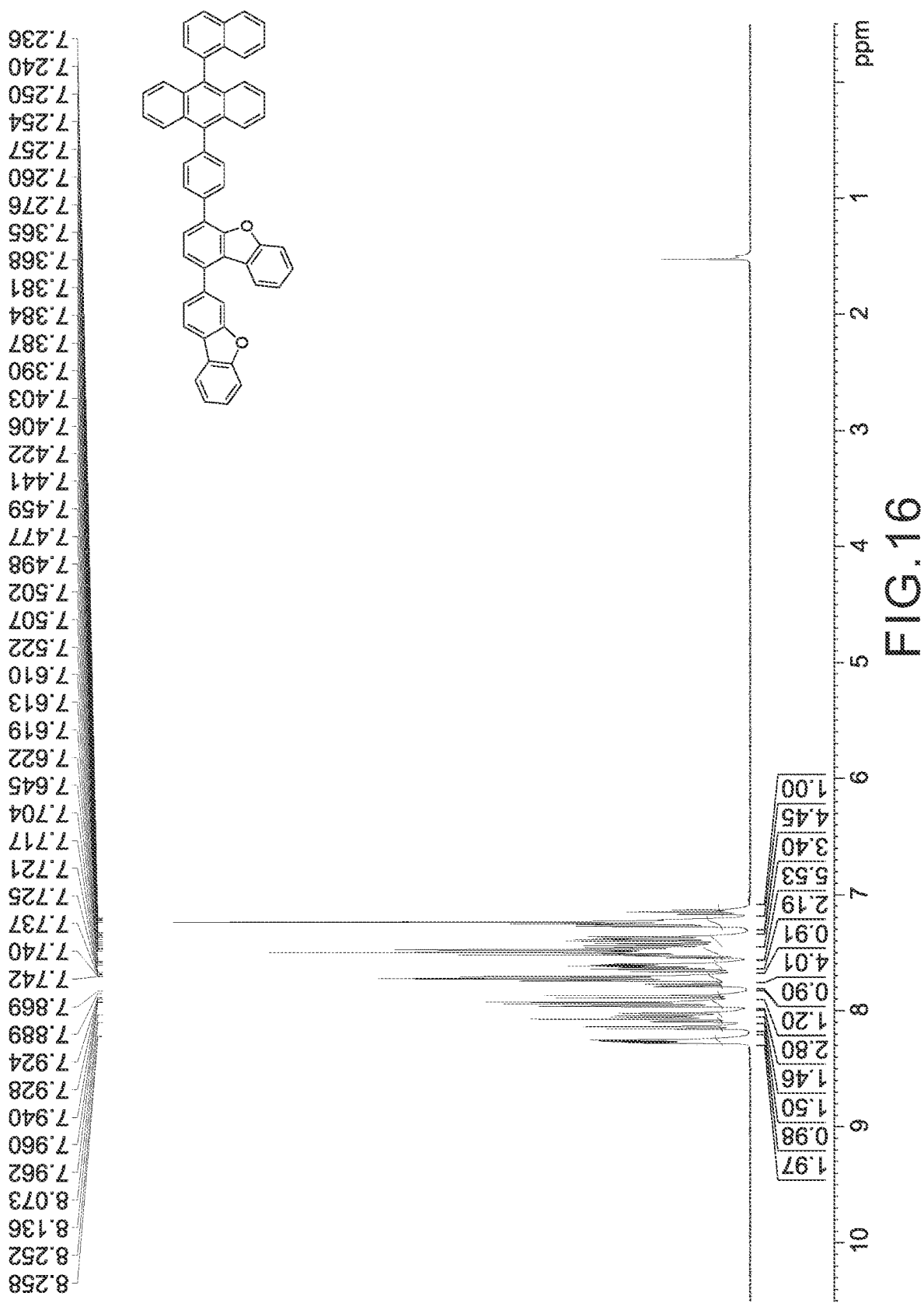
Figure 17:
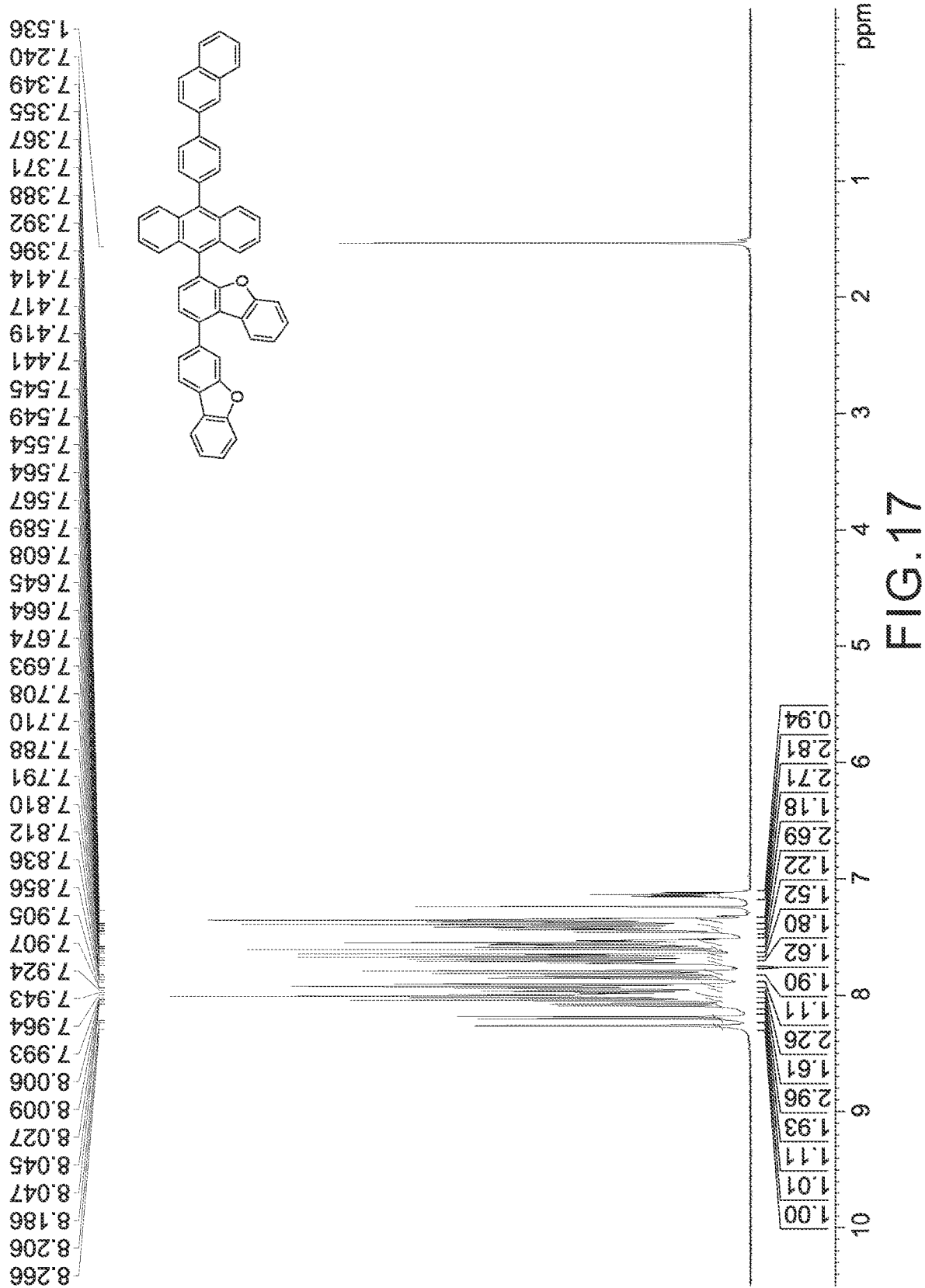
Figure 18:
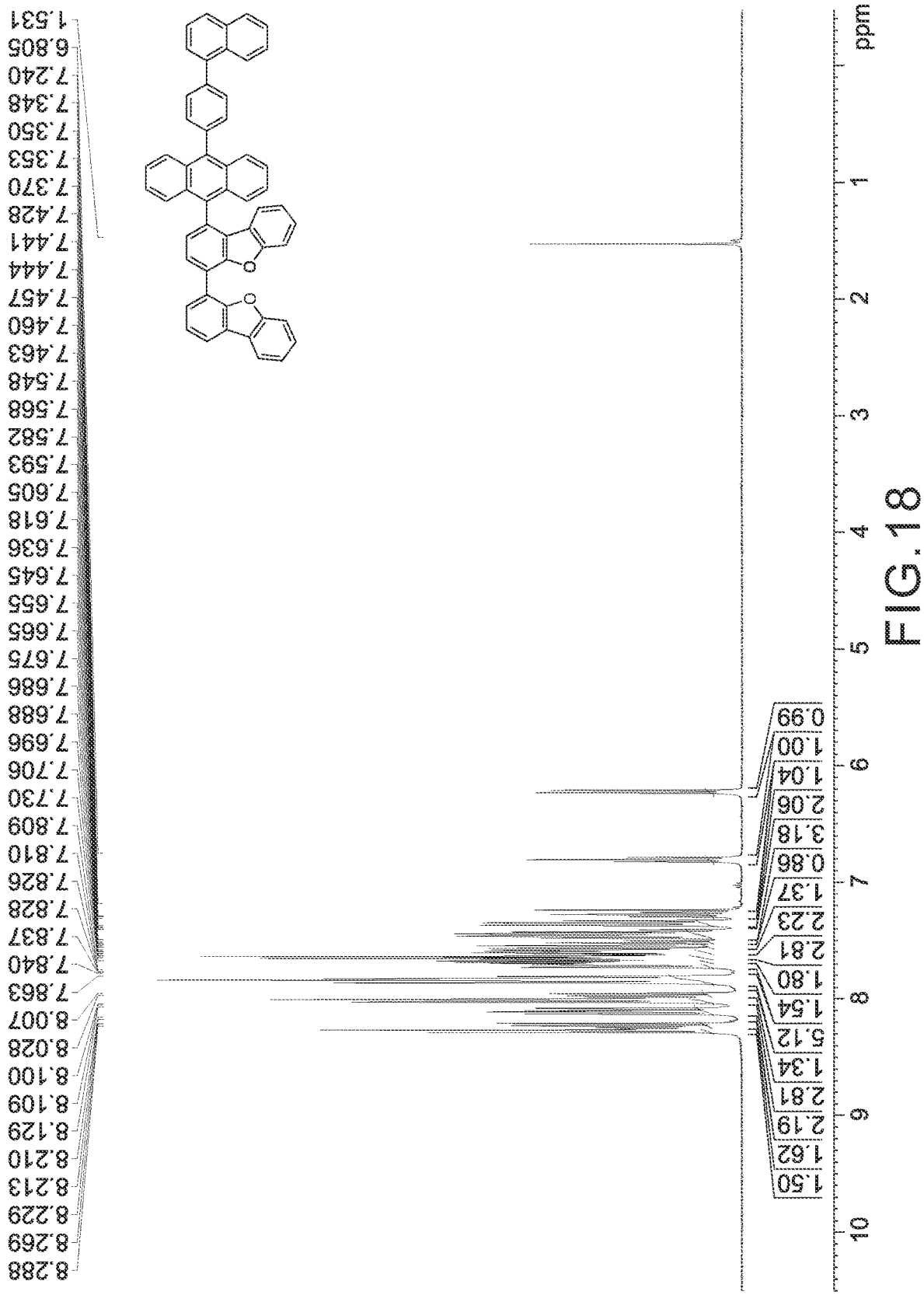
Figure 19:
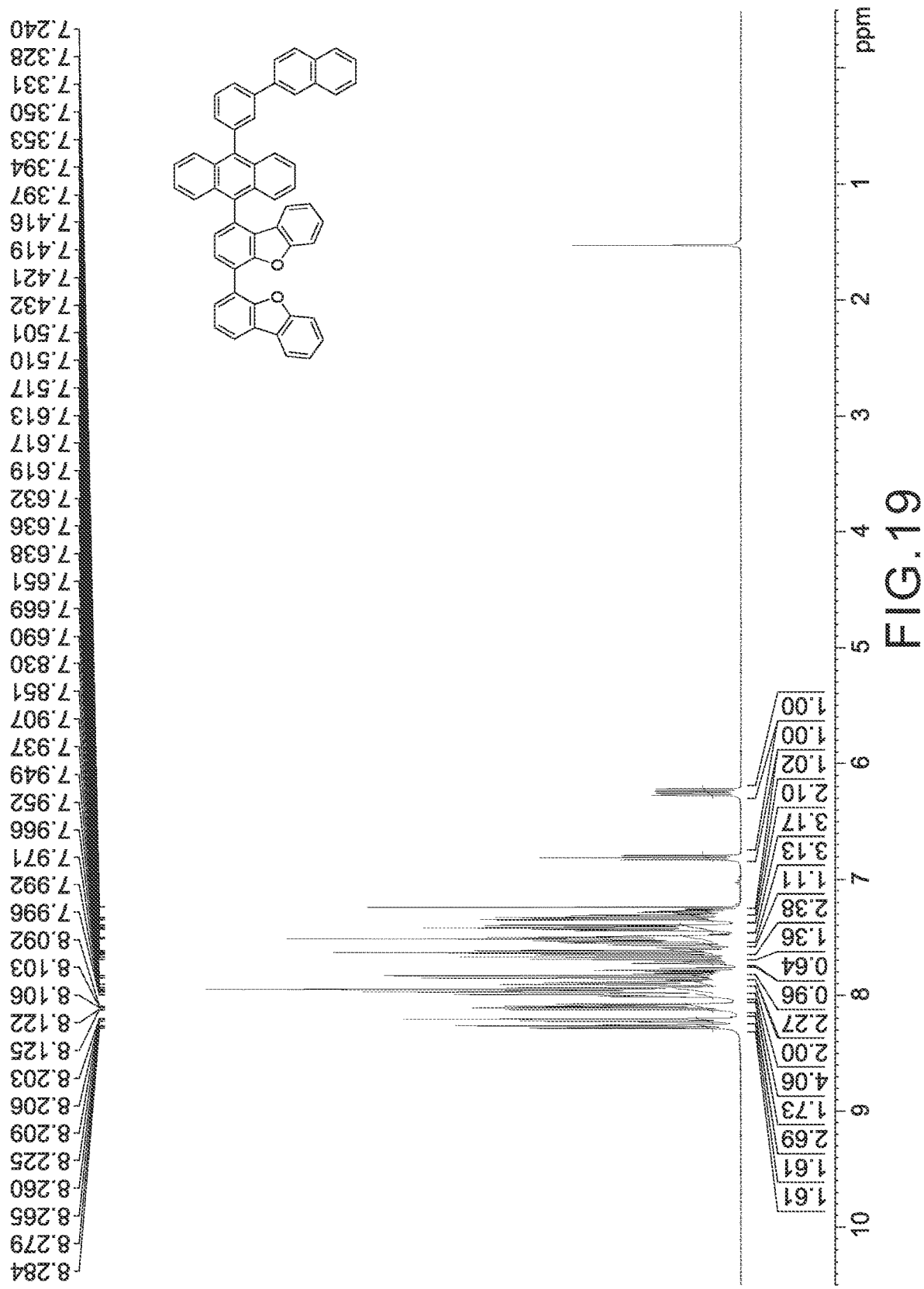
Figure 20:
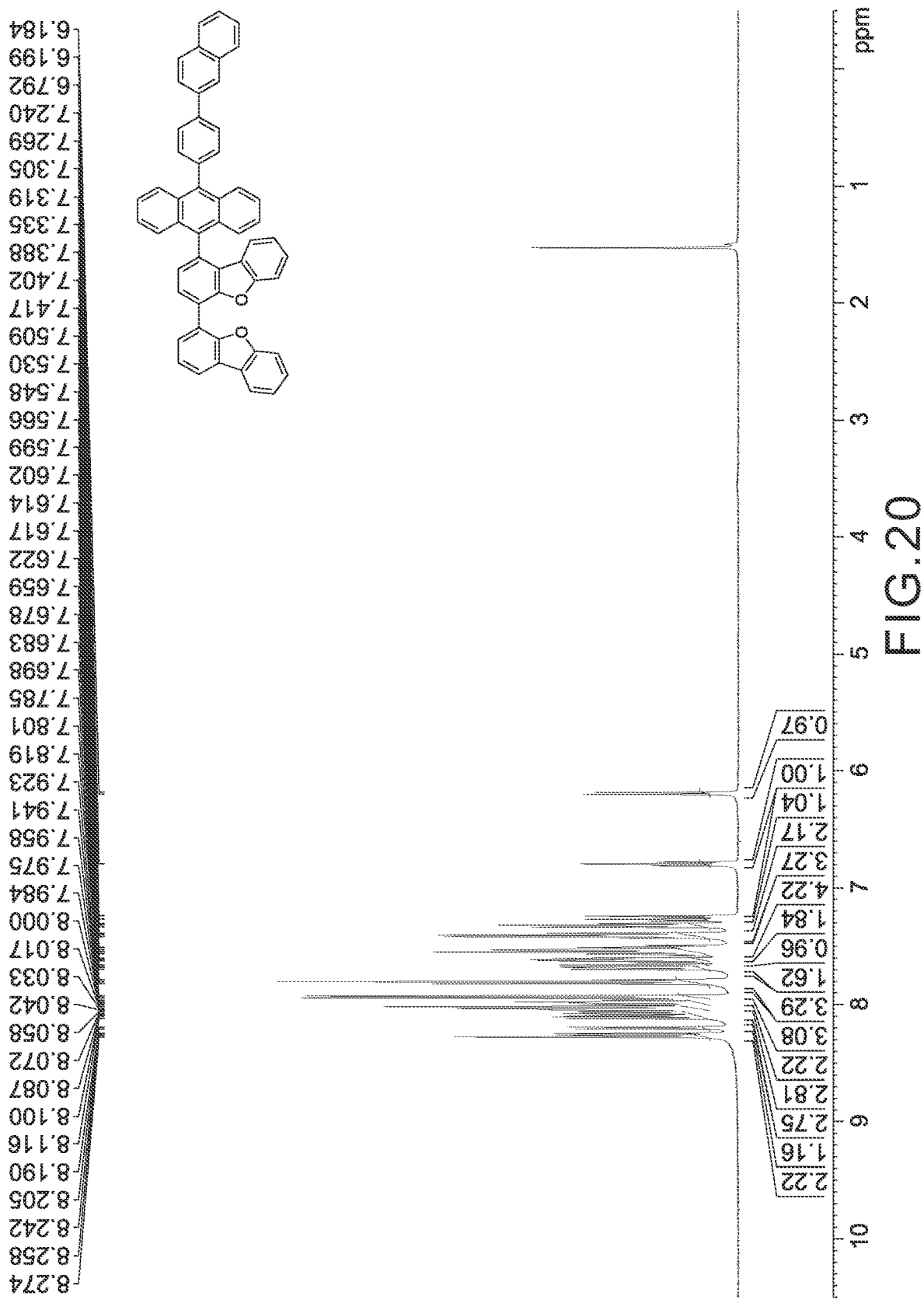
Figure 21:
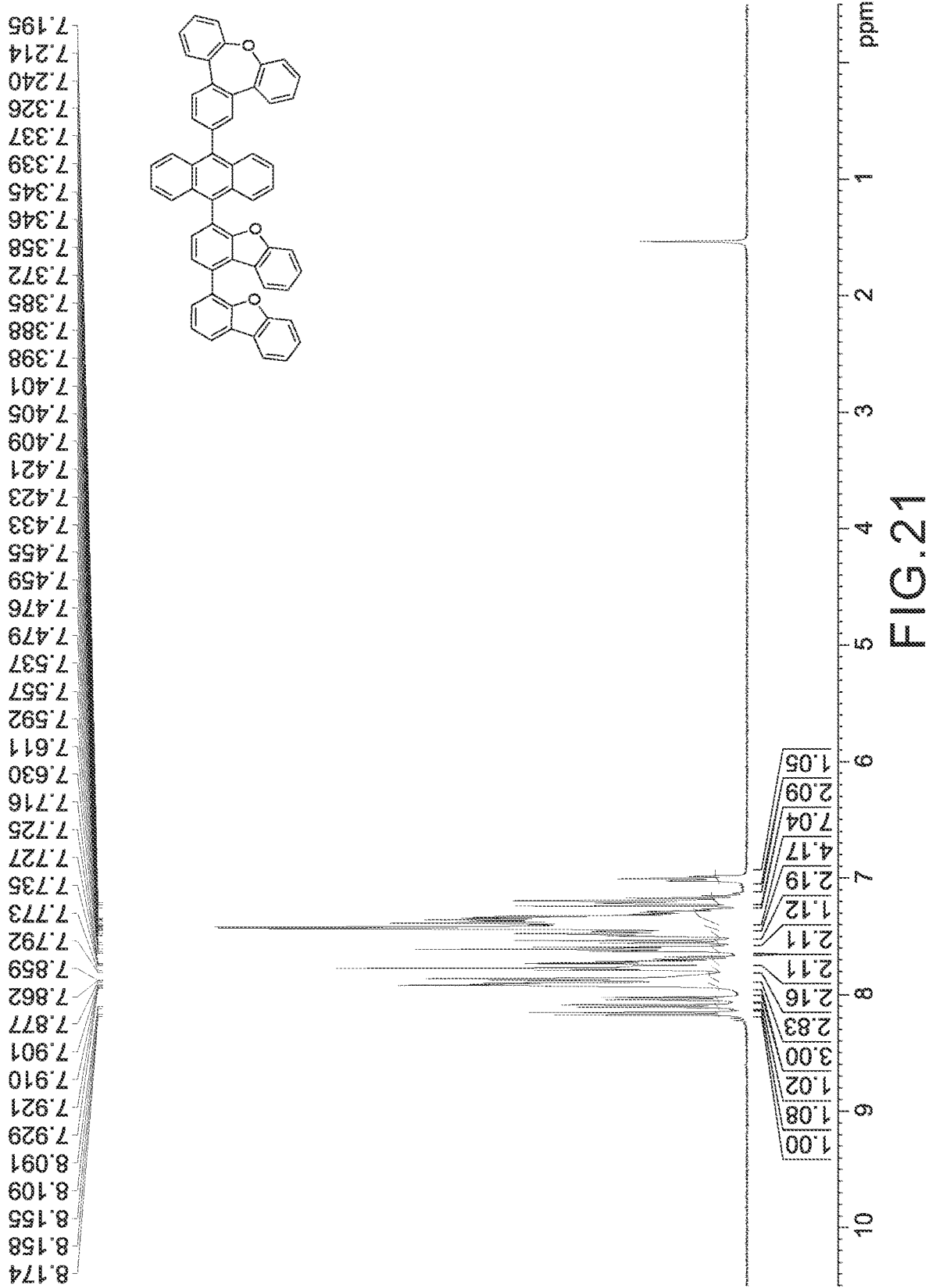
Figure 22:
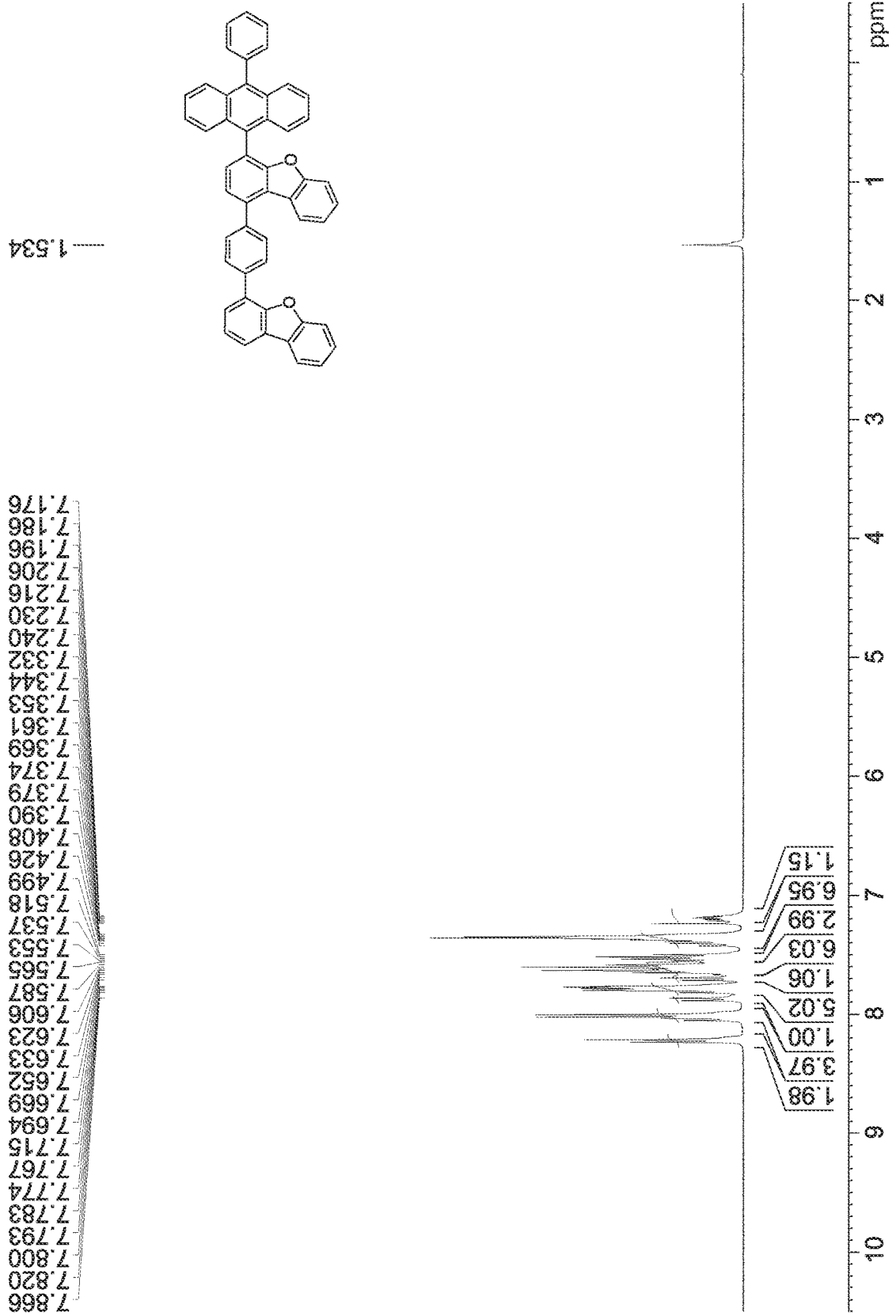

Compounds 1 to 23 were identified by $H^1$-NMR and FD-MS, and the chemical structure, yield, formula and mass of each of Compounds 1 to 23 were also listed in Table 8. According to FIGS. 2 to 22 and the results of $H^1$-NMR, the chemical structures of Compounds 1 to 21 were identified as follows.

TABLE 8 reactants and intermediates adopted to prepare Compounds 1 to 23 and their yields, formulae, and FD-MS data.

| Intermediate An/Reactant Bn No. | Reactant An No. | Chemical Structure of Claimed Compound | Yield (%) | Formula/ Mass (M⁺) |
|---|---|---|---|---|
| A1 | A1 | 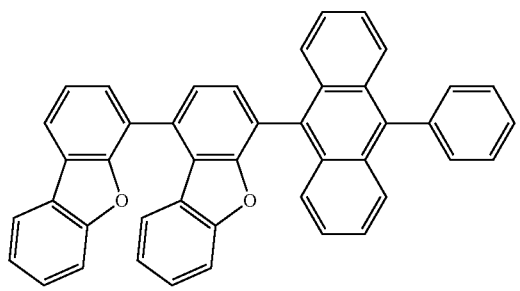 [SMILES: c1ccc(-c2c3ccccc3c(-c3ccc(-c4cccc5c4oc4ccccc45)c4c3oc3ccccc34)c3ccccc23)cc1] Compound 1 | 91.6 | $C_{44}H_{26}O_2$/ 586.68 |

TABLE 8-continued reactants and intermediates adopted to prepare Compounds 1 to 23 and their yields, formulae, and FD-MS data.

| Intermediate An/Reactant | | Claimed Compound | | |
|---|---|---|---|---|
| Bn No. | Reactant An No. | Chemical Structure of Claimed Compound | Yield (%) | Formula/ Mass (M⁺) |
| A2 | A1 | Compound 2 | 92.4 | $C_{44}H_{26}O_2$/ 586.68 |
| A8 | A1 | Compound 3 | 89.2 | $C_{44}H_{26}O_2$/ 586.68 |
| A7 | A1 | Compound 4 | 88.8 | $C_{44}H_{26}O_2$/ 586.68 |
| A1-L | A3 | Compound 5 | 92.9 | $C_{54}H_{32}O_2$/ 712.83 |

TABLE 8-continued reactants and intermediates adopted to prepare Compounds 1 to 23 and their yields, formulae, and FD-MS data.

| Intermediate An/Reactant | | Claimed Compound | | |
|---|---|---|---|---|
| Bn No. | Reactant An No. | Chemical Structure of Claimed Compound | Yield (%) | Formula/ Mass (M⁺) |
| A1 | A2 | Compound 6 | 88.6 | $C_{54}H_{32}O_2$/ 712.83 |
| A1 | A3 | Compound 7 | 88.1 | $C_{48}H_{28}O_2$/ 636.73 |
| A4 | A1 | Compound 8 | 90.0 | $C_{44}H_{26}O_2$/ 586.68 |
| A3 | A1 | Compound 9 | 91.5 | $C_{44}H_{26}O_2$/ 586.68 |

TABLE 8-continued
reactants and intermediates adopted to prepare Compounds 1
to 23 and their yields, formulae, and FD-MS data.
| Intermediate An/Reactant | | Claimed Compound | | |
|---|---|---|---|---|
| Bn No. | Reactant An No. | Chemical Structure of Claimed Compound | Yield (%) | Formula/ Mass (M+) |
| A6 | A1 | 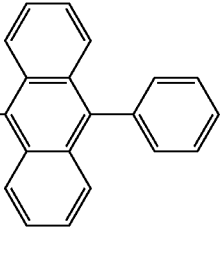 Compound 10 | 87.6 | $C_{56}H_{32}O_3$/ 752.85 |
| A1 | A4 | 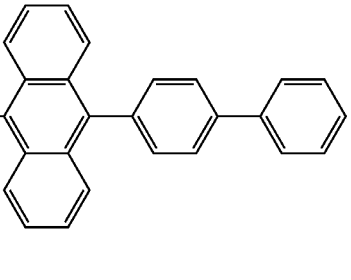 Compound 11 | 93.3 | $C_{50}H_{30}O_2$/ 662.77 |
| A1 | A5 | 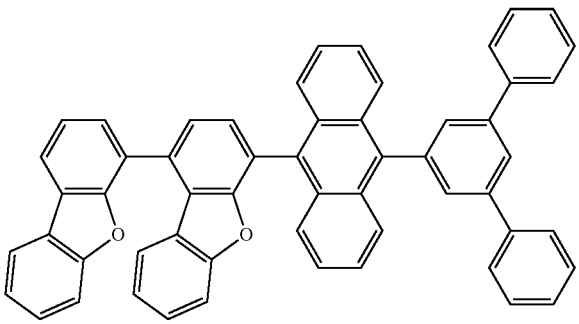 [SMILES: c1ccc(-c2cc(-c3ccccc3)cc(-c3c4ccccc4c(-c4ccc(-c5cccc6c5oc5ccccc56)c5c4oc4ccccc45)c4ccccc34)c2)cc1] Compound 12 | 92.2 | $C_{56}H_{34}O_2$/ 738.87 |
| A4 | A6 | 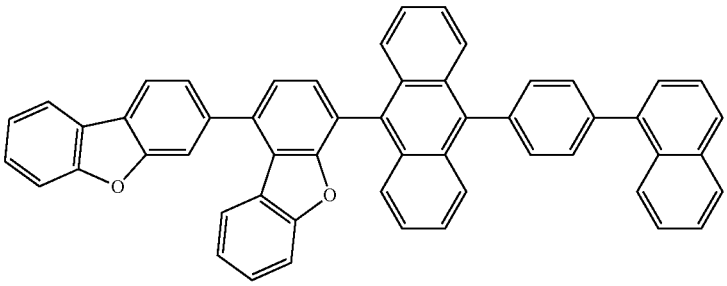 [SMILES: c1ccc2c(-c3ccc(-c4c5ccccc5c(-c5ccc(-c6ccc7c(c6)oc6ccccc67)c6c5oc5ccccc56)c5ccccc45)cc3)cccc2c1] Compound 13 | 88.9 | $C_{54}H_{32}O_2$/ 712.83 |

TABLE 8-continued
reactants and intermediates adopted to prepare Compounds 1 to 23 and their yields, formulae, and FD-MS data.
| Intermediate An/Reactant | | Claimed Compound | | |
|---|---|---|---|---|
| Bn No. | Reactant An No. | Chemical Structure of Claimed Compound | Yield (%) | Formula/ Mass (M+) |
| A4 | A7 | 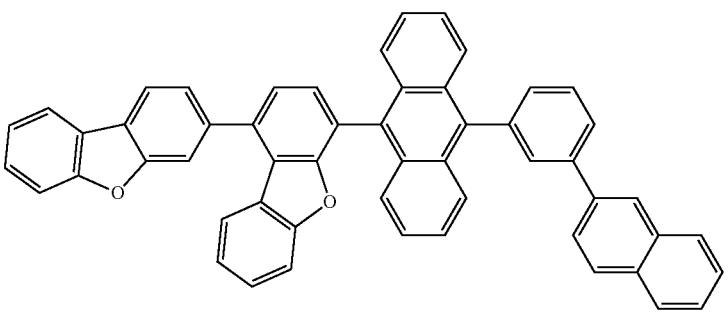<br>Compound 14 | 94.2 | $C_{54}H_{32}O_2$/ 712.83 |
| A4-L | A3 | 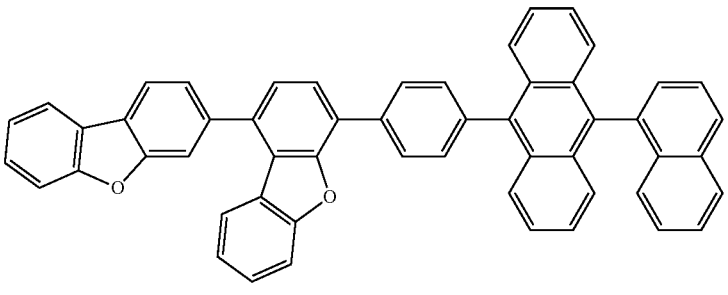 [SMILES: c1ccc2c(-c3c4ccccc4c(-c4ccc(-c5ccc(-c6ccc7c(c6)oc6ccccc67)c6c5oc5ccccc56)cc4)c4ccccc34)cccc2c1]<br>Compound 15 | 93.7 | $C_{54}H_{32}O_2$/ 712.83 |
| A4 | A8 | 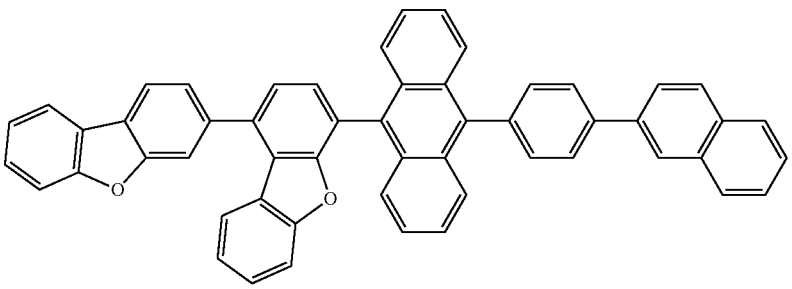 [SMILES: c1ccc2cc(-c3ccc(-c4c5ccccc5c(-c5ccc(-c6ccc7c(c6)oc6ccccc67)c6c5oc5ccccc56)c5ccccc45)cc3)ccc2c1]<br>Compound 16 | 90.7 | $C_{54}H_{32}O_2$/ 712.83 |
| A7 | A6 | 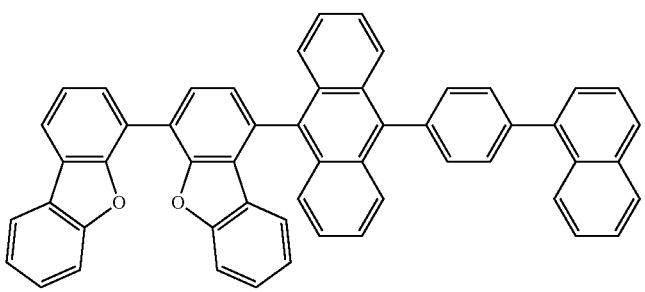 [SMILES: c1ccc2c(-c3ccc(-c4c5ccccc5c(-c5ccc(-c6cccc7c6oc6ccccc67)c6oc7ccccc7c56)c5ccccc45)cc3)cccc2c1]<br>Compound 17 | 91.1 | $C_{54}H_{32}O_2$/ 712.83 |

TABLE 8-continued reactants and intermediates adopted to prepare Compounds 1 to 23 and their yields, formulae, and FD-MS data.

| Intermediate An/Reactant | | Claimed Compound | | |
|---|---|---|---|---|
| Bn No. | Reactant An No. | Chemical Structure of Claimed Compound | Yield (%) | Formula/ Mass (M⁺) |
| A7 | A7 | Compound 18 | 93.6 | $C_{54}H_{32}O_2$/ 712.83 |
| A7 | A8 | Compound 19 | 93.4 | $C_{54}H_{32}O_2$/ 712.83 |
| A1 | A9 | Compound 20 | 91.1 | $C_{56}H_{32}O_3$/ 752.85 |
| A5 | A1 | Compound 21 | 89.5 | $C_{50}H_{30}O_2$/ 662.77 |

TABLE 8-continued reactants and intermediates adopted to prepare Compounds 1 to 23 and their yields, formulae, and FD-MS data.

| Intermediate An/Reactant Bn No. | Reactant An No. | Claimed Compound Chemical Structure of Claimed Compound | Yield (%) | Formula/ Mass (M+) |
|---|---|---|---|---|
| A1 | A10 | Compound 22 | 90.0 | $C_{62}H_{34}O_4$/ 842.93 |
| B1 | A10 | Compound 23 | 92.2 | $C_{50}H_{28}O_3$/ 676.76 |

Modifications of Compounds 1 to 22

In addition to Compounds 1 to 22, one person skilled in the art can react any Intermediate A, i.e., the foresaid Intermediate An or An-L, with any Reactant An through a reaction mechanism similar to Scheme I to synthesize other desired claimed novel compounds.

Modifications of Compound 23

In addition to Compound 23, one person skilled in the art can react any Reactant B, i.e., the foresaid Reactant Bn, with any Reactant An through a reaction mechanism similar to Scheme II to synthesize other desired claimed novel compounds.

Preparation of OLED Devices

A glass substrate coated with an ITO layer (abbreviated as ITO substrate) in a thickness of 1500 Å was placed in distilled water containing a detergent dissolved therein, and was ultrasonically washed. The detergent was a product manufactured by Fischer Co., and the distilled water was distilled water filtered twice through a filter (Millipore Co.). After the ITO layer had been washed for 30 minutes, it was ultrasonically washed twice with distilled water for 10 minutes. After the completion of washing, the glass substrate was ultrasonically washed with isopropyl alcohol, acetone and methanol solvents and then dried, after which it was transported to a plasma cleaner. Then the substrate was cleaned with oxygen plasma for 5 minutes, and then transferred to a vacuum evaporator.

After that, various organic materials and metal materials were sequentially deposited on the ITO substrate to obtain the OLED device of Examples 1 to 20 and Comparative Examples 1 to 4. The vacuum degree during the deposition was maintained at $1\times10^{-6}$ to $3\times10^{-7}$ torr. Herein, the ITO substrate was deposited with a first hole injection layer (HIL-1), a second hole injection layer (HIL-2), a first hole transporting layer (HTL-1), a second hole transporting layer (HTL-2), a blue emission layer (BEL), an electron transporting layer (ETL), an electron injection layer (EIL), and a cathode (Cthd).

To prepare a first blue OLED device and a second blue OLED device, multiple organic layers were respectively deposited on the ITO substrate according to the sequence as listed in Table 10 for the first blue OLED device (abbreviated as B1 device) and the second blue OLED device (abbreviated as B2 device).

Herein, HAT was a material for forming HIL-1 and HIL-2 of B1 device; HID was a material for forming HIL-1 of B2 device; HI-2 was a material for forming HIL-2 of B1 device and for forming HIL-1 and HIL-2 of B2 device; HT-1 and HT-2 were respectively materials for forming HTL-1 of B1 and B2 devices and HTL-2 of B1 and B2 devices; ET was a material for forming ETL of B1 and B2 devices; Liq was a material for forming ETL and EIL of B1 and B2 devices. In the novel compounds of the present invention, commercial host materials were host materials for forming BEL of B1 and B2 devices, and BD was a dopant for forming BEL of B1 and B2 devices. The main difference of the OLEDs between the Examples and Comparative Examples was that the BEL of the OLED in the following comparative examples was made of BH1 or BH2 but the BEL of OLED in the following examples was made of the novel compounds of the present invention listed in Table 8. The detailed chemical structures of foresaid commercial materials were listed in Table 9.

TABLE 9
chemical structures of commercial materials for OLED devices.
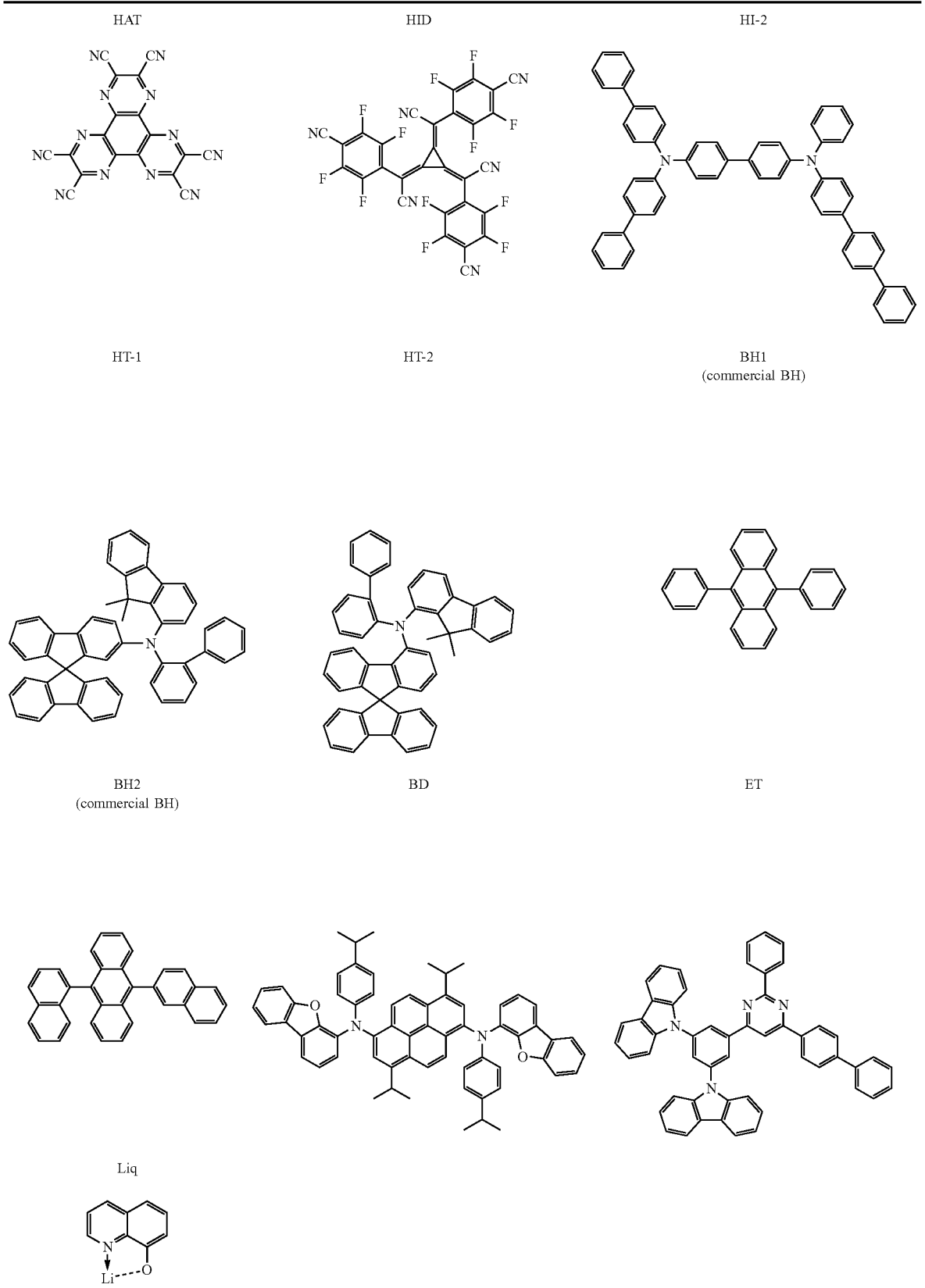

Preparation of Blue OLED Devices

The materials and the thicknesses of the organic layers in the blue OLED devices were also listed in Table 10. The difference between the first and the second blue OLED devices is the materials of HIL-1 and HIL-2 as listed in Table 10.

TABLE 10 coating sequence, materials and thickness of the layers in the blue OLED devices.

| Coating Sequence | Layer | First blue OLED device (B1) | Second blue OLED device (B2) | Thickness |
|---|---|---|---|---|
| 1 | HIL-1 | HAT | HI-2 doped with 3.0 wt % of HID | 100 Å |
| 2 | HIL-2 | HI-2 doped with 5.0 wt % of HAT | HI-2 | 750 Å |
| 3 | HTL-1 | HT-1 | HT-1 | 100 Å |
| 4 | HTL-2 | HT-2 | HT-2 | 100 Å |
| 5 | BEL | Commercial BH/ novel compounds doped with 3.5 wt % of BD | Commercial BH/ novel compounds doped with 3.5 wt % of BD | 300 Å |
| 6 | ETL | ET doped with 35.0 wt % of Liq | ET doped with 35.0 wt % of Liq | 350 Å |
| 7 | EIL | Liq | Liq | 15 Å |
| 8 | Cthd | Al | Al | 1500 Å |

Performance of OLED Devices

To evaluate the performance of OLED devices, the blue OLED devices were measured by PR650 as photometer and Keithley 2400 as power supply. Color coordinates (x,y) were determined according to the CIE chromaticity scale (Commission Internationale de L'Eclairage, 1931). The results were shown in Table 11. For the blue OLED devices, the data were collected at 1000 nits.

The materials of BH, and data of CIE, driving voltage, current efficiency, luminous efficacy, and external quantum efficiency of Examples 1 to 20 and Comparative Examples 1 to 4 were listed in Table 11. As listed in Table 11, Examples 1 to 7 and Comparative Examples 1 to 2 were the first blue OLED device, and Examples 8 to 20 and Comparative Examples 3 to 4 were the second blue OLED device.

TABLE 11 materials of BH, CIEs, voltages, and current efficiencies of OLED devices of Examples 1 to 20 and Comparative Examples 1 to 4.

| Example No. | Material of BH | CIE (x, y) | Voltage (V) | Current Efficiency (cd/A) | Luminous Efficacy (lm/W) | External Quantum Efficiency (%) |
|---|---|---|---|---|---|---|
| E1 | Compound 1 | (0.129, 0.158) | 4.60 | 11.40 | 7.45 | 7.90 |
| E2 | Compound 2 | (0.129, 0.153) | 4.61 | 10.60 | 7.12 | 7.40 |
| E3 | Compound 3 | (0.131, 0.148) | 3.99 | 9.28 | 7.31 | 6.40 |
| E4 | Compound 4 | (0.129, 0.157) | 4.46 | 10.90 | 7.65 | 7.53 |
| E5 | Compound 7 | (0.132, 0.142) | 4.43 | 11.10 | 7.82 | 7.37 |
| E6 | Compound 9 | (0.130, 0.151) | 4.45 | 10.20 | 7.22 | 7.12 |
| E7 | Compound 11 | (0.130, 0.152) | 4.45 | 10.60 | 7.47 | 6.93 |
| C1 | BH2 | (0.128, 0.154) | 4.62 | 9.03 | 6.13 | 5.77 |
| C2 | BH1 | (0.134, 0.152) | 5.08 | 3.98 | 2.46 | 3.04 |
| E8 | Compound 5 | (0.129, 0.157) | 4.41 | 9.99 | 7.14 | 6.65 |
| E9 | Compound 8 | (0.128, 0.156) | 4.33 | 10.80 | 7.86 | 7.72 |
| E10 | Compound 10 | (0.130, 0.160) | 4.50 | 10.60 | 7.33 | 7.08 |
| E11 | Compound 12 | (0.133, 0.161) | 4.35 | 9.61 | 6.94 | 6.34 |
| E12 | Compound 13 | (0.128, 0.176) | 4.19 | 11.50 | 8.62 | 7.61 |
| E13 | Compound 14 | (0.130, 0.171) | 4.13 | 11.10 | 8.43 | 6.94 |
| E14 | Compound 15 | (0.128, 0.172) | 4.29 | 11.50 | 8.45 | 7.29 |
| E15 | Compound 16 | (0.128, 0.179) | 4.12 | 11.20 | 8.55 | 7.34 |
| E16 | Compound 17 | (0.128, 0.172) | 4.16 | 10.80 | 8.16 | 7.01 |
| E17 | Compound 18 | (0.130, 0.147) | 4.03 | 9.20 | 6.61 | 6.28 |
| E18 | Compound 19 | (0.129, 0.175) | 4.08 | 11.20 | 8.62 | 6.78 |
| E19 | Compound 21 | (0.128, 0.165) | 4.45 | 11.20 | 7.92 | 7.88 |
| E20 | Compound 23 | (0.131, 0.162) | 4.04 | 11.40 | 8.83 | 7.24 |
| C3 | BH2 | (0.128, 0.158) | 4.52 | 9.16 | 6.36 | 6.23 |
| C4 | BH1 | (0.133, 0.157) | 4.63 | 4.04 | 2.74 | 3.09 |

Based on the results, in comparison with the commercial host materials for the blue emission layer, adopting Compounds 1 to 5, 7 to 19, 21, and 23 as the host material for the blue emission layer can reduced the driving voltage and improve the current efficiency, luminous efficacy, and external quantum efficiency of the blue OLEDs. It demonstrated that the novel compound of the present invention is suitable as a host material for any blue OLEDs, and allows the OLEDs using the same to have low driving voltage and improved current efficiency, luminous efficacy, and external quantum efficiency.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A compound for a host material of an emission layer represented by the following Formula (I'):

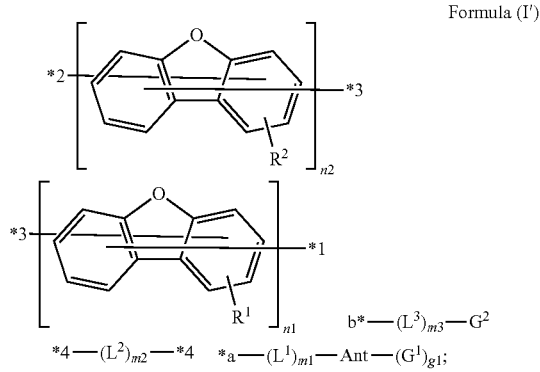

Formula (I')

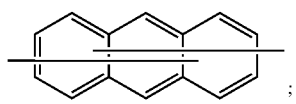

wherein *1 is bonded to *a, *2 is bonded to *b, and two *3s are bonded to two *4s, respectively;

wherein n1 is an integer from 1 to 3, n2 is an integer from 0 to 2, and the sum of n1 and n2 is 2 or 3;

m1 and m2 are each independently an integer 0 or 1, m1 and m2 are the same or different; and m3 is 0;

g1 is an integer from 0 to 9;

$R^1$ and $R^2$ are each independently selected from the group consisting of: a hydrogen atom, a deuterium atom, an alkyl group having 1 to 12 carbon atoms, and an aryl group having 6 to 30 ring carbon atoms, and $R^1$ and $R^2$ are the same or different;

$L^1$, $L^2$ and $L^3$ are each independently an arylene group having 6 to 60 ring carbon atoms, and $L^1$, $L^2$ and $L^3$ are the same or different;

Ant is

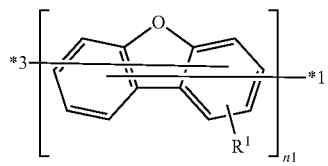

$G^1$ and $G^2$ are each independently selected from the group consisting of: a hydrogen atom, a deuterium atom, an alkyl group having 1 to 40 carbon atoms, an alkenyl group having 2 to 40 carbon atoms, an alkynyl group having 2 to 40 carbon atoms, a cycloalkyl group having 3 to 60 ring carbon atoms, a heterocycloalkyl group having 3 to 60 ring carbon atoms, an aryl group having 6 to 60 ring carbon atoms, and a heteroaryl group having 3 to 60 ring carbon atoms;

wherein the group of

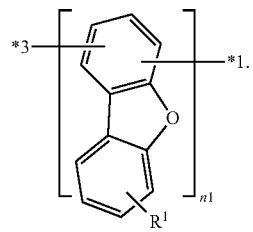

in Formula (I') is represented by

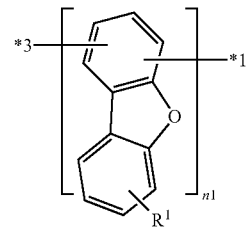

the group of

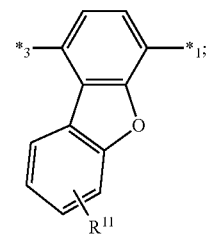

is represented by any one of the following formulae:

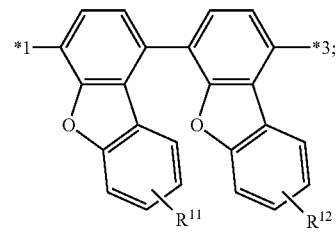

131
-continued
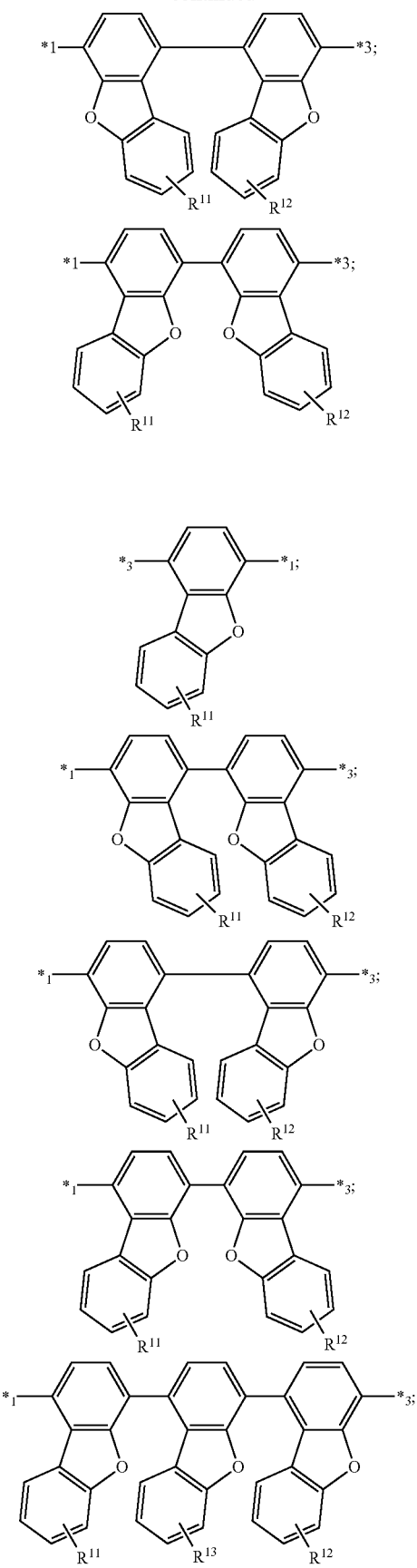
132
-continued
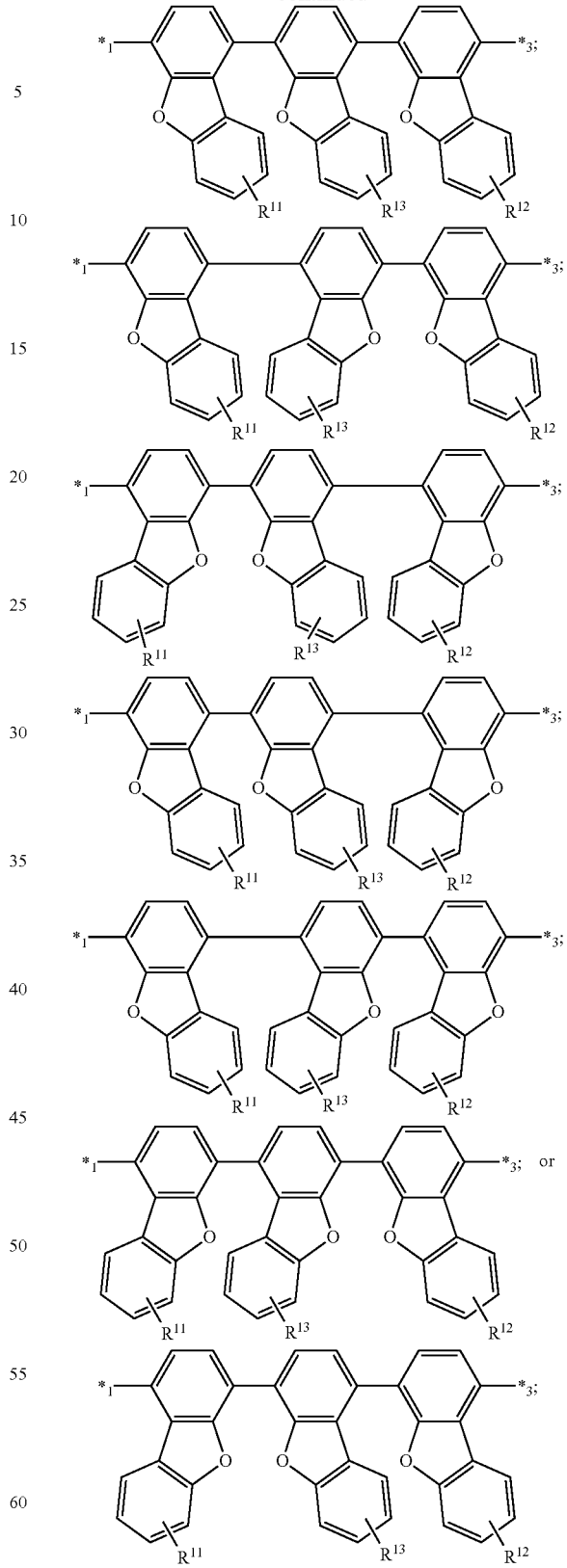
wherein $R^{11}$ to $R^{13}$ are each independently selected from the group consisting of: a hydrogen atom, a deuterium atom, an alkyl group having 1 to 12 carbon atoms, and an aryl group having 6 to 30 ring carbon atoms, and R¹¹ to R¹³ are the same or different: and
the group of
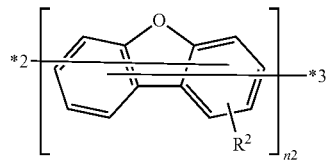
in Formula (I') is represented by
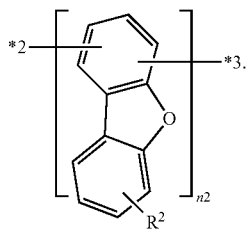
2. The compound for a host material of an emission layer as claimed in claim 1, wherein the group of
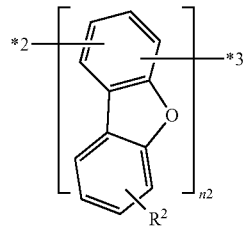
in Formula (I') is represented by any one of the following formulae:
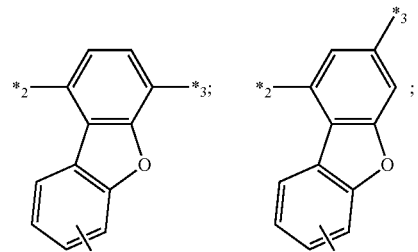
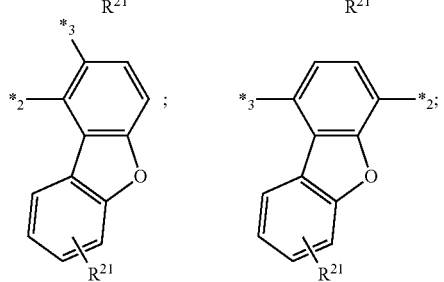
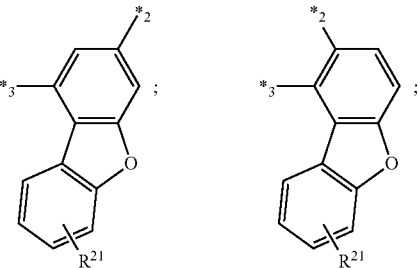
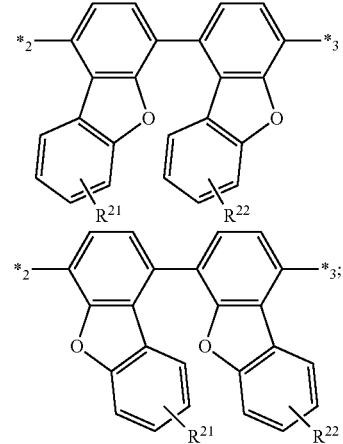
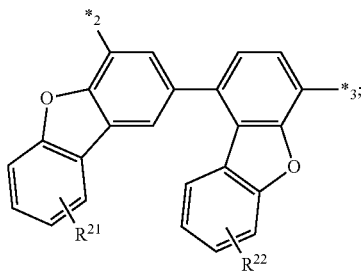
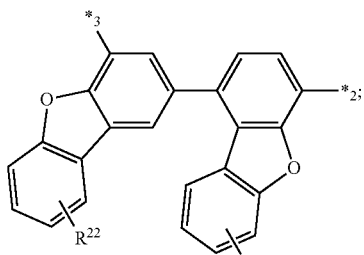
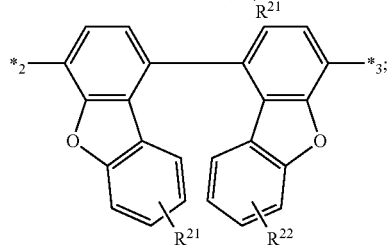
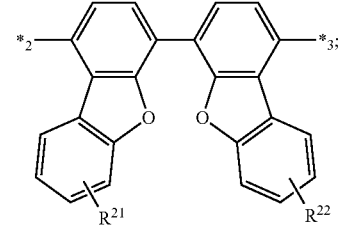

135
-continued

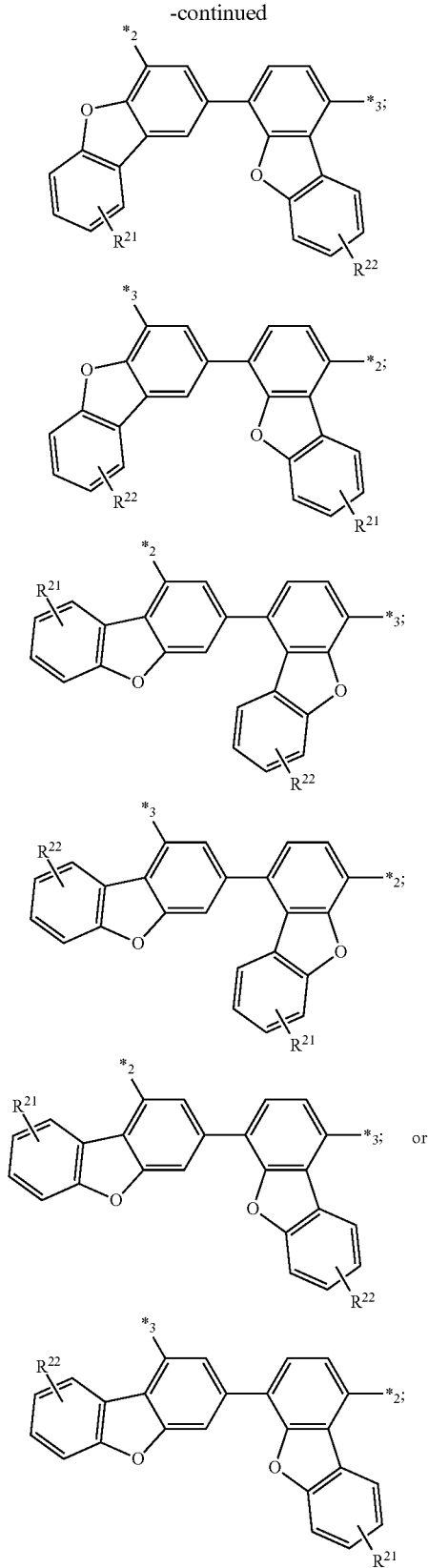

wherein R²¹ to R²³ are each independently selected from the group consisting of: a hydrogen atom, a deuterium atom, an alkyl group having 1 to 12 carbon atoms, and an aryl group having 6 to 30 ring carbon atoms, and R²¹ to R²³ are the same or different.

3. The compound for a host material of an emission layer as claimed in claim 1, wherein the heteroaryl group having 3 to 60 ring carbon atoms represented by G² is represented by any one of the following formulae:

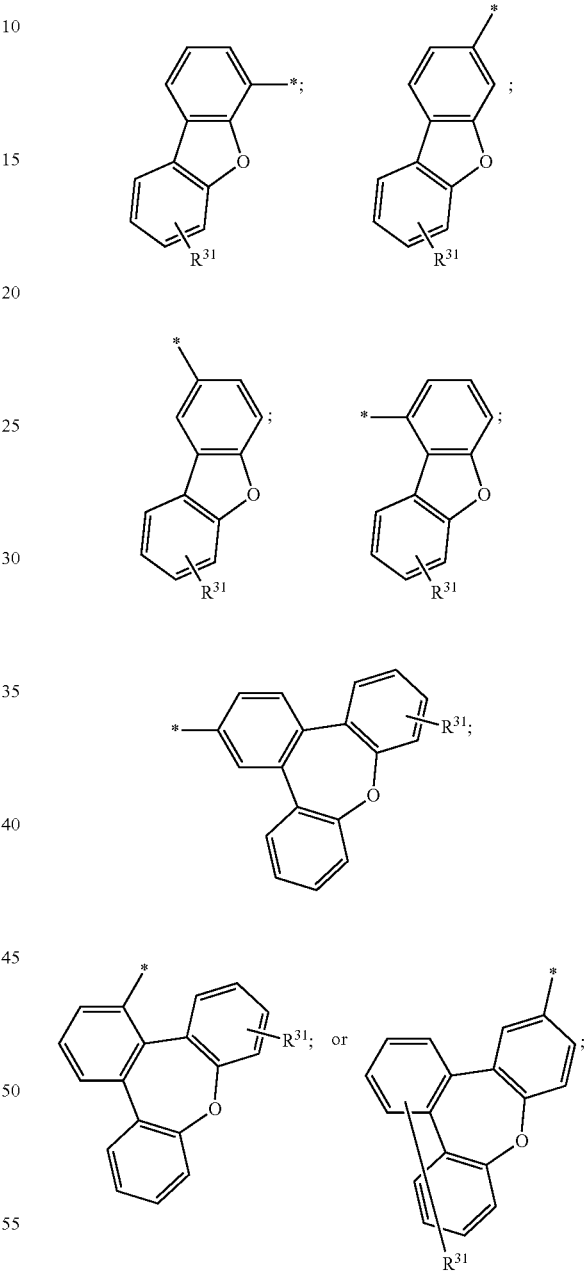

wherein R³¹ to R³³ are each independently selected from the group consisting of: a hydrogen atom, a deuterium atom, an alkyl group having 1 to 12 carbon atoms, and an aryl group having 6 to 30 ring carbon atoms, and R³¹ to R³³ are the same or different.

4. The compound for a host material of an emission layer as claimed in claim 1, wherein the compound is represented by the following Formula (I'''):

Formula (I''')

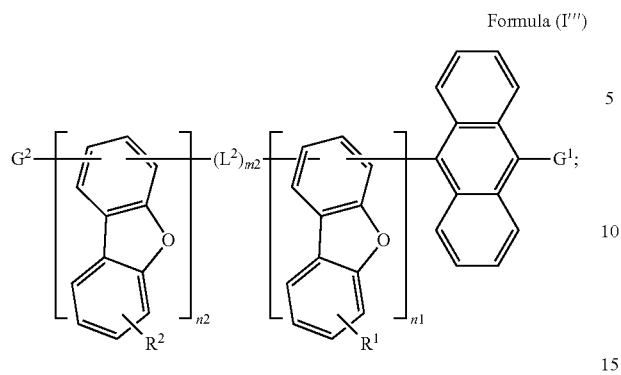

G¹ is selected from the group consisting of: the alkyl group having 1 to 40 carbon atoms, the alkenyl group having 2 to 40 carbon atoms, the alkynyl group having 2 to 40 carbon atoms, and the aryl group having 6 to 60 ring carbon atoms; and G² is selected from the group consisting of: the hydrogen atom, the deuterium atom, the alkyl group having 1 to 40 carbon atoms, the alkenyl group having 2 to 40 carbon atoms, the alkynyl group having 2 to 40 carbon atoms, and the aryl group having 6 to 60 ring carbon atoms.

5. The compound for a host material of an emission layer as claimed in claim 1, wherein the aryl groups having 6 to 60 ring carbon atoms represented by G¹ and G² are each independently selected from the group consisting of: a phenyl group, a biphenylyl group, a terphenylyl group, a quaterphenylyl group, a quinquephenylyl group, a naphthyl group, an acenaphthelenyl group, an anthryl group, a benzanthryl group, an aceanthryl group, a phenanthryl group, a benzophenanthryl group, a phenalenyl group, a fluorenyl group, a benzofluorenyl group, a dibenzofluorenyl group, a picenyl group, a pentacenyl group, a pyrenyl group, a benzopyrenyl group, a chrysenyl group, a benzochrysenyl group, a fluoranthenyl group, a benzofluoranthenyl group, a tetracenyl group, a perylenyl group, a coronyl group, a dibenzanthryl group, a naphthylphenyl group, an indacenyl group, a triphenylenyl group, a benzotriphenylenyl group, and any isomeric group thereof.

6. The compound for a host material of an emission layer as claimed in claim 1, wherein the aryl groups having 6 to 60 ring carbon atoms represented by G¹ and G² are each independently selected from the group consisting of:

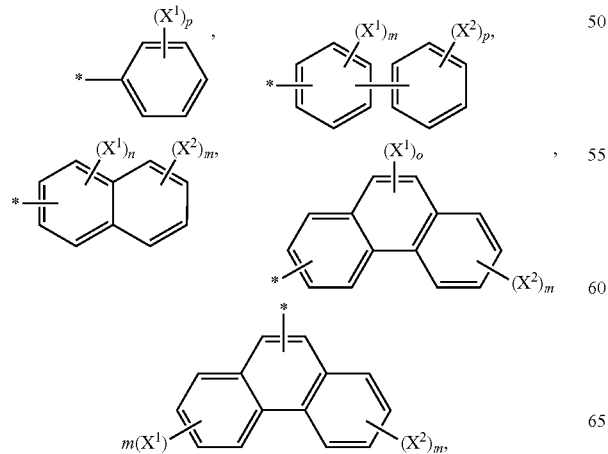

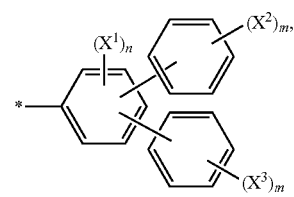

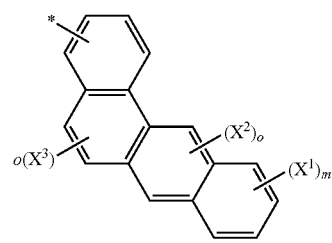

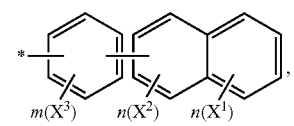

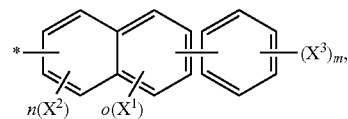

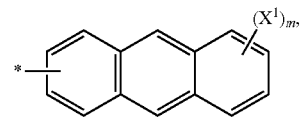

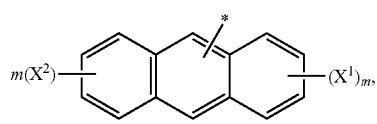

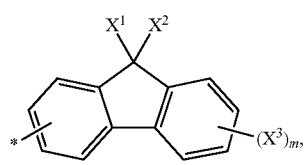

-continued

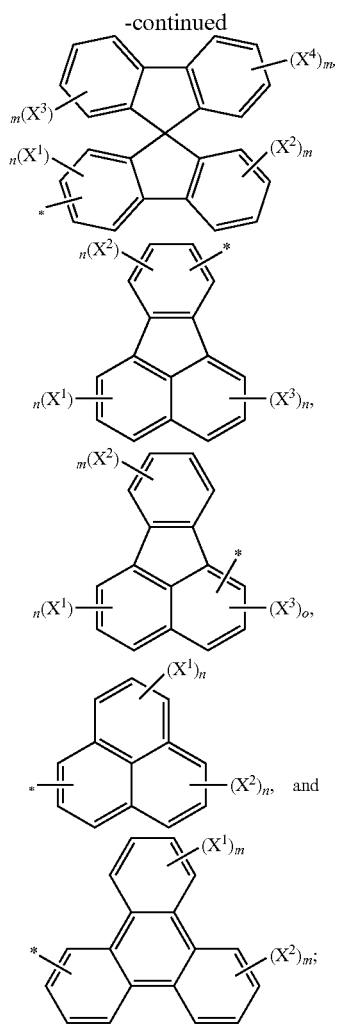

wherein m is an integer from 1 to 4, n is an integer from 1 to 3, o is an integer 1 or 2, and p is an integer from 1 to 5;

$X^1$ to $X^4$ are each independently selected from the group consisting of: a hydrogen atom, a deuterium atom, a halo group, a cyano group, a nitro group, an alkyl group having 1 to 12 carbon atoms, an alkenyl group having 2 to 12 carbon atoms, an alkynyl group having 2 to 12 carbon atoms, an alkoxy group having 1 to 12 carbon atoms, an aryl group having 6 to 30 ring carbon atoms, a heteroaryl group having 3 to 30 ring carbon atoms, and an aryloxy group having 6 to 30 ring carbon atoms.

7. The compound for a host material of an emission layer as claimed in claim 1, wherein the aryl group having 6 to 60 ring carbon atoms represented by $G^1$ is selected from the group consisting of:

-continued

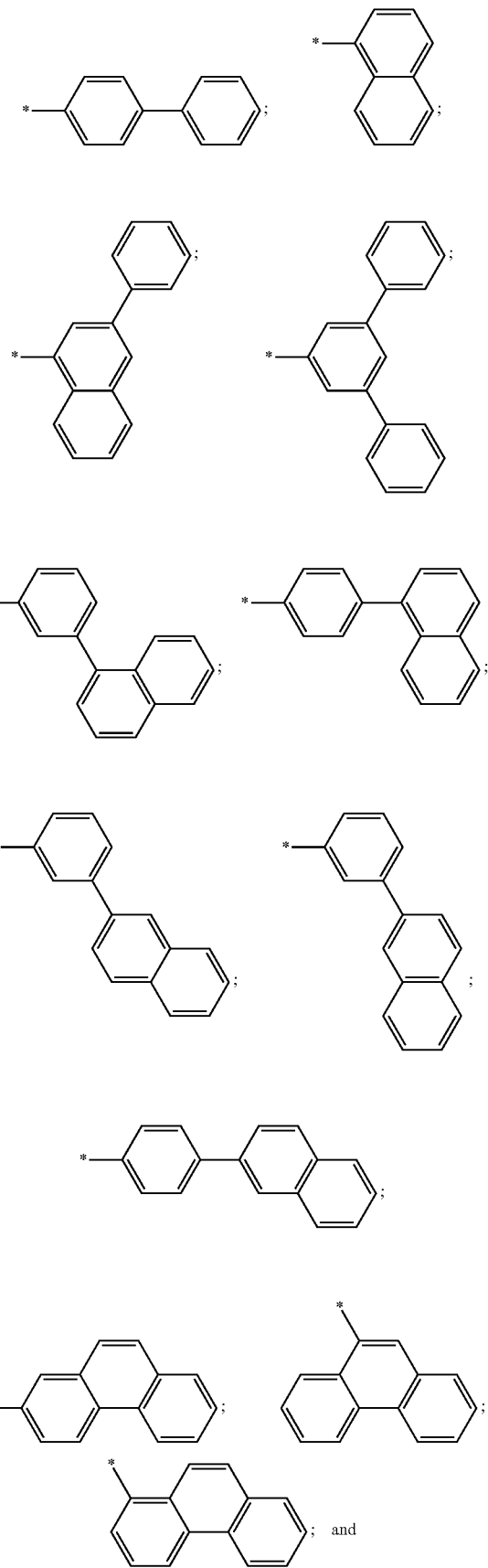

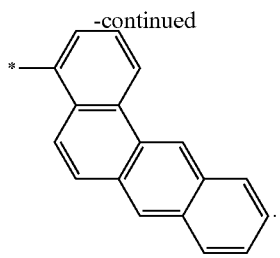

8. The compound for a host material of an emission layer as claimed in claim 1, wherein the arylene groups having 6 to 60 ring carbon atoms represented by L¹, L² and L³ are each independently selected from the group consisting of:

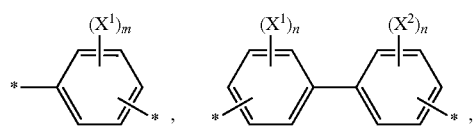

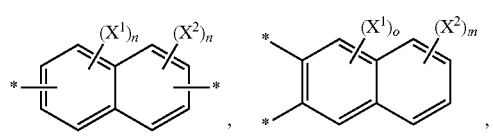

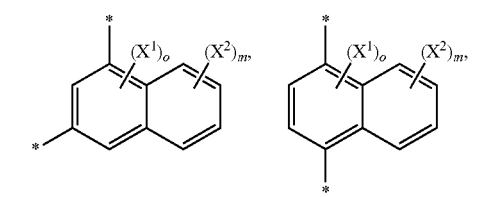

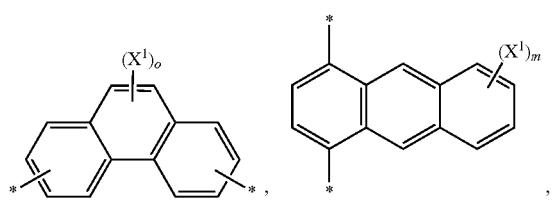

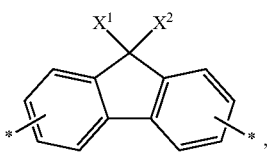

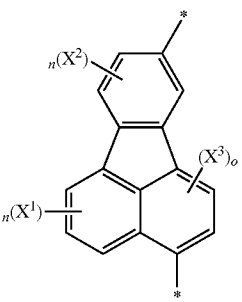

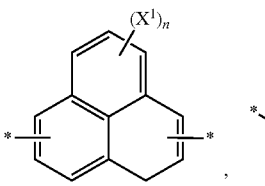

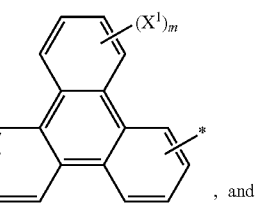

, and

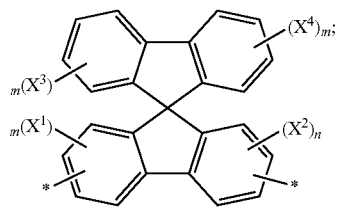

wherein m is an integer from 1 to 4, n is an integer from 1 to 3, and o is an integer 1 or 2;

X¹ to X⁴ are each independently selected from the group consisting of: a hydrogen atom, a deuterium atom, a halo group, a cyano group, a nitro group, an alkyl group having 1 to 12 carbon atoms, an alkenyl group having 2 to 12 carbon atoms, an alkynyl group having 2 to 12 carbon atoms, an alkoxy group having 1 to 12 carbon atoms, an aryl group having 6 to 30 ring carbon atoms, a heteroaryl group having 3 to 30 ring carbon atoms, and an aryloxy group having 6 to 30 ring carbon atoms.

9. The compound for a host material of an emission layer as claimed in claim 1, wherein g1 is an integer from 0 to 2.

10. The compound for a host material of an emission layer as claimed in claim 9, wherein g1 is 1, G¹ is represented by

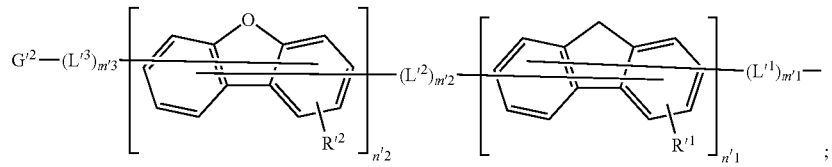

wherein n'1 and n'2 are each independently an integer from 0 to 3, and the sum of n'1 and n'2 is 2 or 3;

m'1, m'2 and m'3 are each independently an integer 0 or 1, and m'1, m'2 and m'3 are the same or different;

$R'^1$ and $R'^2$ are each independently selected from the group consisting of: a hydrogen atom, a deuterium atom, an alkyl group having 1 to 6 carbon atoms, and an aryl group having 6 to 18 ring carbon atoms, and $R'^1$ and $R'^2$ are the same or different;

$L'^1$, $L'^2$ and $L'^3$ are each independently an arylene group having 6 to 18 ring carbon atoms, $L'^1$, and $L'^2$ and $L'^3$ are the same or different;

$G'^2$ is selected from the group consisting of: a hydrogen atom, a deuterium atom, an alkyl group having 1 to 12 carbon atoms, an alkenyl group having 2 to 12 carbon atoms, an alkynyl group having 2 to 12 carbon atoms, a cycloalkyl group having 3 to 30 ring carbon atoms, a heterocycloalkyl group having 3 to 30 ring carbon atoms, an aryl group having 6 to 30 ring carbon atoms, and a heteroaryl group having 3 to 30 ring carbon atoms.

11. The compound for a host material of an emission layer as claimed in claim 1, wherein the compound is selected from the group consisting of:

Compound 1

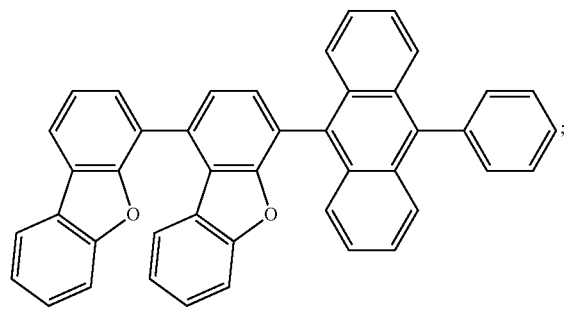

Compound 2

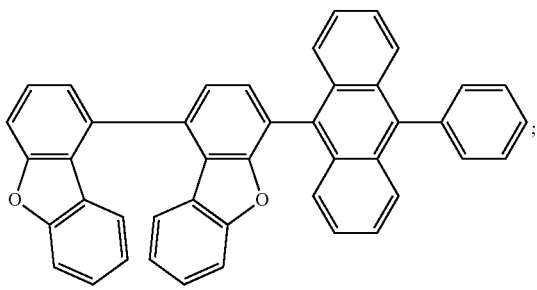

Compound 4

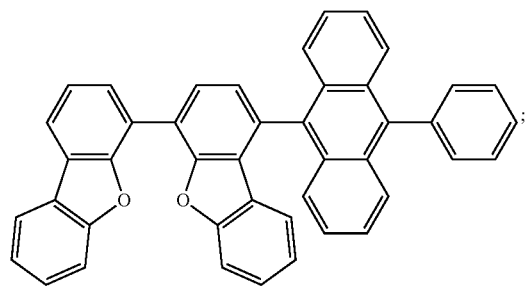

Compound 5

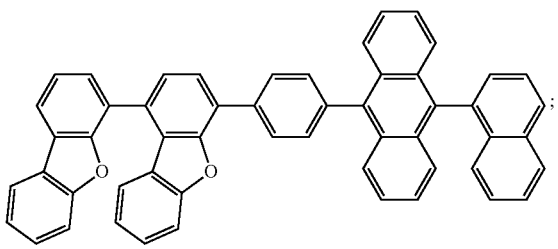

Compound 6

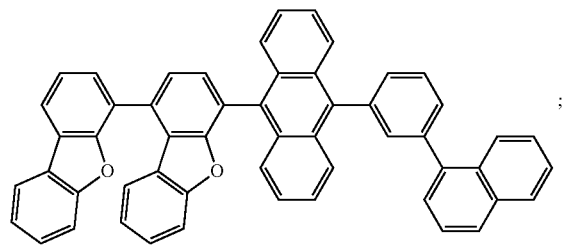

Compound 7

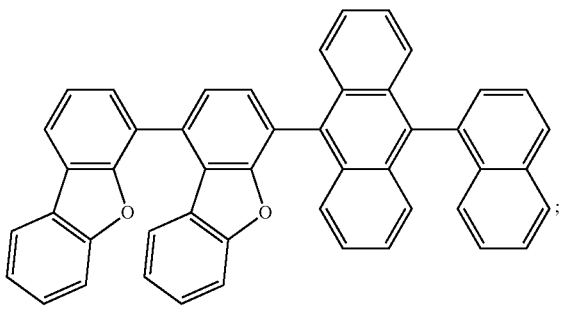

Compound 8

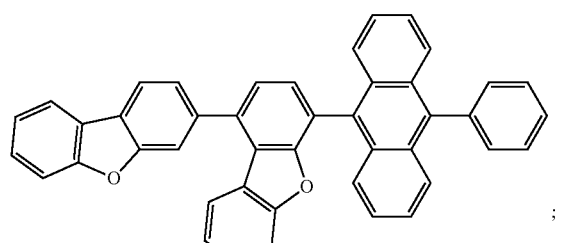

Compound 9

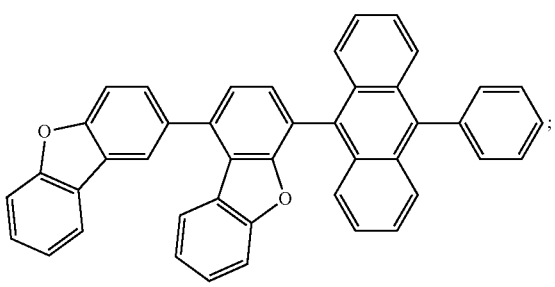

-continued
Compound 10
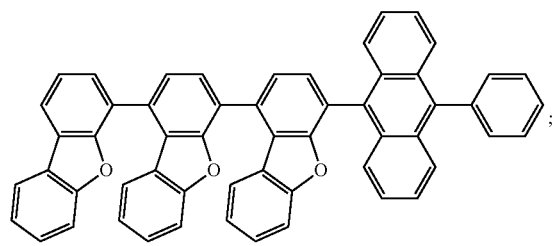
Compound 11
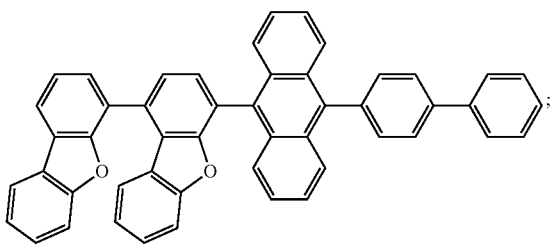
Compound 12
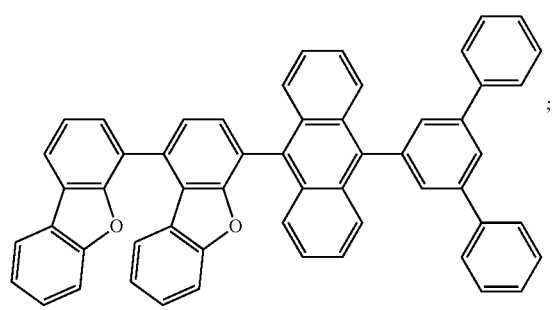
Compound 13
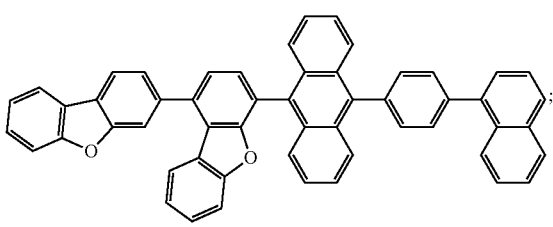
Compound 14
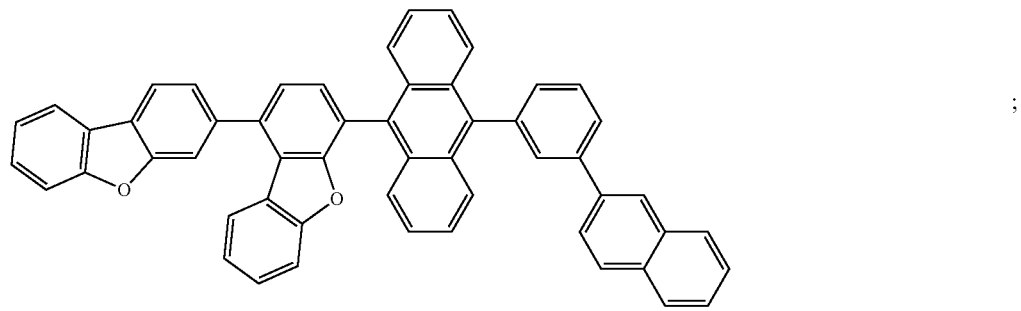
Compound 15
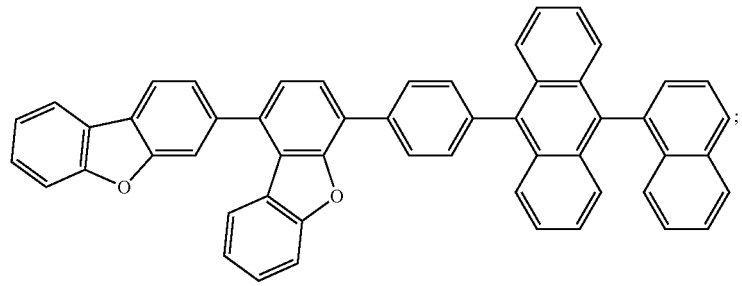
Compound 16
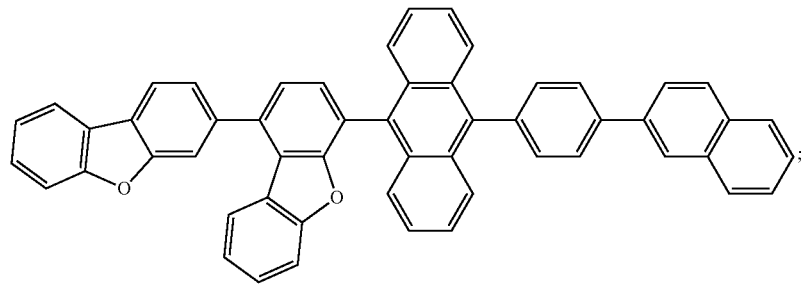

-continued
Compound 17
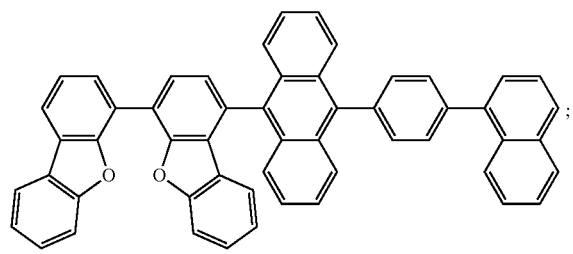
Compound 18
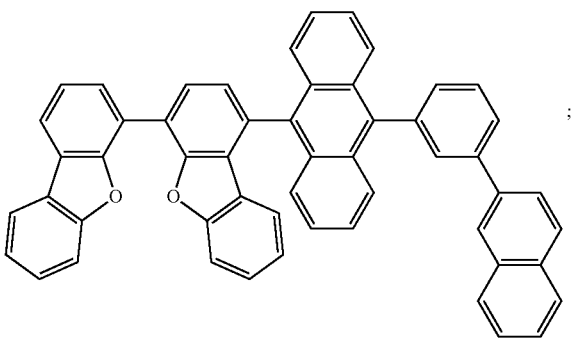
Compound 19
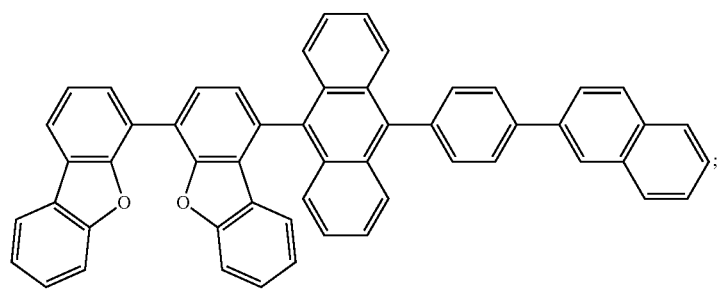
Compound 20
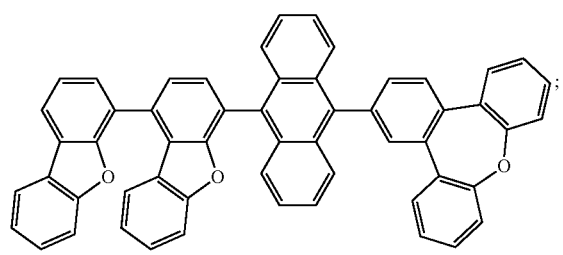
Compound 21
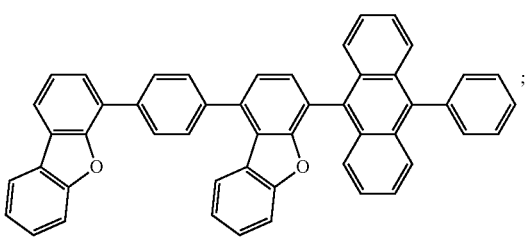
Compound 22
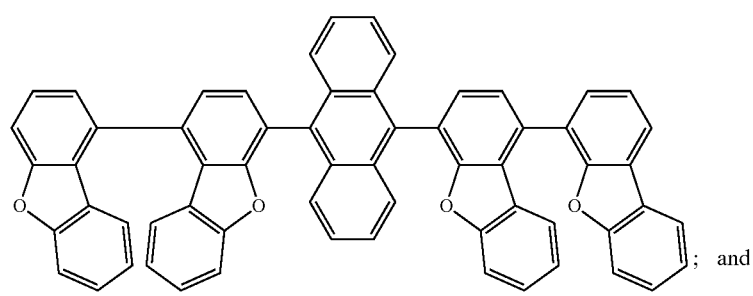; and
Compound 23
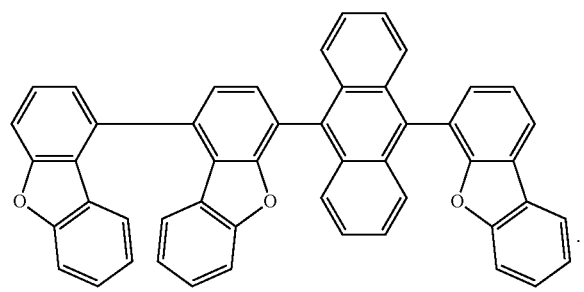.

12. An organic electronic device, comprising a first electrode, a second electrode, and an organic layer disposed between the first electrode and the second electrode, wherein the organic layer comprises the compound for a host material of an emission layer as claimed in claim 1.

13. The organic electronic device as claimed in claim 12, wherein the organic electronic device is an organic light emitting device.

14. The organic electronic device as claimed in claim 13, wherein the organic light emitting device comprises:
  a hole injection layer formed on the first electrode;
  a hole transport layer formed on the hole injection layer;
  an emission layer formed on the hole transport layer, wherein the emission layer comprises a dopant and a first host material, and the first host material is the compound for a host material of an emission layer as claimed in claim 1;
  an electron transport layer formed on the emission layer; and
  an electron injection layer formed between the electron transport layer and the second electrode.

15. The organic electronic device as claimed in claim 14, wherein the emission layer further comprises a second host material, the second host material is the compound for a host material of an emission layer as claimed in claim 1, and the second host material is different from the first host material.

16. The organic electronic device as claimed in claim 13, wherein the organic electronic device is a blue organic electronic device.

* * * * *